US009890210B2

(12) United States Patent
Zeller et al.

(10) Patent No.: US 9,890,210 B2
(45) Date of Patent: *Feb. 13, 2018

(54) ANTAGONIST ANTIBODIES DIRECTED AGAINST CALCITONIN GENE-RELATED PEPTIDE

(71) Applicant: Teva Pharmaceuticals International GmbH, Jona (CH)

(72) Inventors: Joerg Zeller, Ann Arbor, MI (US); Kristian T. Poulsen, San Francisco, CA (US); Yasmina Noubia Abdiche, Mountain View, CA (US); Jaume Pons, San Bruno, CA (US); Sierra Jones Collier, Menlo Park, CA (US); Arnon Rosenthal, Woodside, CA (US)

(73) Assignee: Teva Pharmaceuticals International GmbH, Jona (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/588,432

(22) Filed: May 5, 2017

(65) Prior Publication Data

US 2017/0240622 A1    Aug. 24, 2017

Related U.S. Application Data

(60) Continuation of application No. 15/147,265, filed on May 5, 2016, which is a continuation of application No. 15/044,552, filed on Feb. 16, 2016, now Pat. No. 9,365,648, which is a continuation of application No. 14/719,015, filed on May 21, 2015, now Pat. No. 9,328,168, which is a continuation of application No. 14/251,925, filed on Apr. 14, 2014, now Pat. No. 9,115,194, which is a continuation of application No. 14/086,816, filed on Nov. 21, 2013, now Pat. No. 8,734,802, which is a continuation of application No. 13/870,871, filed on Apr. 25, 2013, now Pat. No. 8,597,649, which is a continuation of application No. 13/179,846, filed on Jul. 11, 2011, now Pat. No. 8,586,045, which is a division of application No. 12/093,638, filed as application No. PCT/IB2006/003181 on Nov. 2, 2006, now Pat. No. 8,007,794.

(60) Provisional application No. 60/736,623, filed on Nov. 14, 2005.

(51) Int. Cl.
*A61K 39/395* (2006.01)
*C12P 21/08* (2006.01)
*C07K 16/18* (2006.01)
*A61K 39/00* (2006.01)

(52) U.S. Cl.
CPC ........ *C07K 16/18* (2013.01); *A61K 2039/505* (2013.01); *C07K 2317/21* (2013.01); *C07K 2317/24* (2013.01); *C07K 2317/33* (2013.01); *C07K 2317/34* (2013.01); *C07K 2317/52* (2013.01); *C07K 2317/55* (2013.01); *C07K 2317/565* (2013.01); *C07K 2317/567* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 4,814,567 A | 3/1989 | Cabilly et al. |
| 5,116,964 A | 5/1992 | Capon et al. |
| 5,500,362 A | 3/1996 | Robinson et al. |
| 5,545,806 A | 8/1996 | Longberg et al. |
| 5,545,807 A | 8/1996 | Surani et al. |
| 5,569,825 A | 10/1996 | Longberg et al. |
| 5,625,126 A | 4/1997 | Longberg et al. |
| 5,633,425 A | 5/1997 | Longberg et al. |
| 5,661,016 A | 8/1997 | Longberg et al. |
| 5,750,373 A | 5/1998 | Garrard et al. |
| 5,821,337 A | 10/1998 | Carter et al. |
| 5,851,556 A | 12/1998 | Breton et al. |
| 5,932,215 A | 8/1999 | De Lacharriere et al. |
| 5,938,586 A | 8/1999 | De Lacharriere et al. |
| 6,180,370 B1 | 1/2001 | Queen et al. |
| 6,168,809 B1 | 8/2001 | De Lacharriere et al. |
| 6,313,097 B1 | 11/2001 | Eberlein et al. |
| 6,344,438 B1 | 2/2002 | De Lacharriere et al. |
| 6,509,014 B1 | 1/2003 | De Lacharriere et al. |
| 6,521,609 B1 | 2/2003 | Doods et al. |
| 6,586,458 B1 | 7/2003 | Plachetka |
| 6,737,056 B1 | 5/2004 | Presta |
| 6,767,056 B2 | 5/2004 | Presta |
| 7,479,488 B2 | 1/2009 | Mueller et al. |

(Continued)

FOREIGN PATENT DOCUMENTS

| | | |
|---|---|---|
| CN | 1308676 | 5/2001 |
| CN | 1671711 | 9/2005 |

(Continued)

OTHER PUBLICATIONS

U.S. Appl. No. 13/621,981, filed Sep. 18, 2012, Poulsen et al.

(Continued)

*Primary Examiner* — Christine J Saoud
*Assistant Examiner* — Jon M Lockard
(74) *Attorney, Agent, or Firm* — Fish & Richardson P.C.

(57) ABSTRACT

The invention features methods for preventing or treating CGRP associated disorders such as vasomotor symptoms, including headaches (e.g., migraine, cluster headache, and tension headache) and hot flushes, by administering an anti-CGRP antagonist antibody. Antagonist antibody G1 and antibodies derived from G1 directed to CGRP are also described.

15 Claims, 16 Drawing Sheets

(56) References Cited

U.S. PATENT DOCUMENTS

| | | |
|---|---|---|
| 8,007,794 B2 | 8/2011 | Zeller et al. |
| 8,293,239 B2 | 10/2012 | Poulsen et al. |
| 8,298,536 B2 | 10/2012 | Poulsen et al. |
| 8,586,045 B2 | 11/2013 | Zeller et al. |
| 8,597,649 B2 | 12/2013 | Zeller et al. |
| 8,623,366 B2 | 1/2014 | Pios et al. |
| 8,734,802 B1 | 5/2014 | Zeller et al. |
| 9,115,194 B2 | 8/2015 | Zeller et al. |
| 9,266,951 B2 | 2/2016 | Zeller et al. |
| 9,328,168 B2 | 5/2016 | Zeller et al. |
| 9,340,614 B2 | 5/2016 | Zeller et al. |
| 9,346,881 B2 | 5/2016 | Zeller et al. |
| 9,365,648 B1 | 6/2016 | Zeller et al. |
| 2002/0162125 A1 | 10/2002 | Salmon et al. |
| 2003/0194404 A1 | 10/2003 | Greenfeder et al. |
| 2004/0110170 A1 | 6/2004 | Pisegna et al. |
| 2005/0234054 A1 | 10/2005 | Mueller et al. |
| 2006/0183700 A1 | 8/2006 | Vater et al. |
| 2009/0220489 A1 | 9/2009 | Zeller et al. |
| 2010/0172895 A1 | 7/2010 | Boone et al. |
| 2011/0054150 A1 | 3/2011 | Poulsen et al. |
| 2011/0257371 A1 | 10/2011 | Poulsen et al. |
| 2011/0305711 A1 | 10/2011 | Poulsen et al. |
| 2012/0009192 A1 | 1/2012 | Zeller et al. |
| 2012/0225075 A1 | 9/2012 | Pios et al. |
| 2012/0294797 A1 | 11/2012 | Kovacevich et al. |
| 2012/0294802 A1 | 11/2012 | Russo et al. |
| 2013/0216535 A1 | 8/2013 | Zeller et al. |
| 2013/0295087 A1 | 11/2013 | Poulsen et al. |
| 2013/0295088 A1 | 11/2013 | Poulsen et al. |
| 2014/0147438 A1 | 5/2014 | Zeller et al. |
| 2014/0308290 A1 | 10/2014 | Pios et al. |
| 2014/0314767 A1 | 10/2014 | Pios et al. |
| 2015/0050267 A1 | 2/2015 | Zeller et al. |
| 2015/0266948 A1 | 9/2015 | Bigal et al. |
| 2015/0302690 A1 | 10/2015 | Poulsen et al. |
| 2015/0307607 A1 | 11/2015 | Bigal et al. |
| 2015/0322142 A1 | 12/2015 | Zeller et al. |
| 2015/0361171 A1 | 12/2015 | Zeller et al. |
| 2015/0361172 A1 | 12/2015 | Zeller et al. |
| 2015/0361173 A1 | 12/2015 | Zeller et al. |
| 2016/0168244 A1 | 2/2016 | Zeller et al. |

FOREIGN PATENT DOCUMENTS

| | | |
|---|---|---|
| EP | 0 212 432 | 3/1987 |
| EP | 1031350 | 8/2000 |
| EP | 1556020 | 7/2005 |
| EP | 1770091 | 4/2007 |
| EP | 2380592 | 10/2011 |
| JP | 07-196700 | 8/1995 |
| JP | 08-268874 | 10/1996 |
| JP | 2007523870 | 8/2007 |
| JP | 2009515942 | 4/2009 |
| RU | 2329062 | 7/2008 |
| WO | WO 1991/000737 | 1/1991 |
| WO | WO 1994/021665 A1 | 9/1994 |
| WO | WO 1995/05468 A1 | 2/1995 |
| WO | WO 1996/004928 A1 | 2/1996 |
| WO | WO 1996/33735 A1 | 10/1996 |
| WO | WO 1997/009046 A1 | 3/1997 |
| WO | WO 1997/041223 A1 | 11/1997 |
| WO | WO 1998/003534 A1 | 1/1998 |
| WO | WO 1998/008630 | 3/1998 |
| WO | WO 1998/009630 A1 | 3/1998 |
| WO | WO 1998/011128 A1 | 3/1998 |
| WO | WO 1998/056779 A1 | 12/1998 |
| WO | WO 1999/058572 A1 | 11/1999 |
| WO | WO 2000/018764 A1 | 4/2000 |
| WO | WO 2003/093472 A2 | 11/2003 |
| WO | WO 2003/104236 A1 | 12/2003 |
| WO | WO 2004/003019 A2 | 1/2004 |
| WO | WO 2004/014351 A2 | 2/2004 |
| WO | WO 2004/050683 A2 | 6/2004 |
| WO | WO 2004/082602 A2 | 9/2004 |
| WO | WO 2004/082605 A2 | 9/2004 |
| WO | WO 2004/082678 A1 | 9/2004 |
| WO | WO 2004/083187 A1 | 9/2004 |
| WO | WO 2004/087649 A2 | 10/2004 |
| WO | WO 2004/091514 A2 | 10/2004 |
| WO | WO 2004/092166 A2 | 10/2004 |
| WO | WO 2004/092168 A1 | 10/2004 |
| WO | WO 2005/009962 A1 | 2/2005 |
| WO | WO 2005/100360 A1 | 10/2005 |
| WO | WO 2006/077212 A1 | 7/2006 |
| WO | WO 2007/025212 A2 | 3/2007 |
| WO | WO 2007/025286 A2 | 3/2007 |
| WO | WO 2007/035906 A2 | 3/2007 |
| WO | WO 2007/048026 A2 | 4/2007 |
| WO | WO 2007/054809 A2 | 5/2007 |
| WO | WO 2007/061676 A2 | 5/2007 |
| WO | WO 2007/076336 A1 | 7/2007 |
| WO | WO 2007 076336 A1 | 7/2007 |
| WO | WO 2008/011190 A1 | 1/2008 |
| WO | WO 2009/109908 A1 | 9/2009 |
| WO | WO 2009/109911 A1 | 9/2009 |
| WO | WO 2010/006168 A2 | 1/2010 |
| WO | WO 2010/075238 | 7/2010 |
| WO | WO 2011/024113 A1 | 3/2011 |
| WO | WO 2011/156324 A1 | 12/2011 |

OTHER PUBLICATIONS

U.S. Appl. No. 13/623,206, filed Sep. 20, 2012, Poulsen et al.
U.S. Appl. No. 13/835,394, filed Mar. 25, 2013, Zeller et al.
U.S. Appl. No. 13/892,121, filed May 10, 2013, Poulsen et al.
U.S. Appl. No. 13/892,130, filed May 10, 2013, Zeller et al.
U.S. Appl. No. 14/057,747, filed Oct. 18, 2013, Pios et al.
U.S. Appl. No. 14/295,583, filed Jun. 4, 2014, Pios et al.
U.S. Appl. No. 14/612,110, filed Feb. 2, 2015, Poulsen et al.
U.S. Appl. No. 14/612,117, filed Feb. 2, 2015, Zeller et al.
U.S. Appl. No. 14/664,715, filed Mar. 20, 2015, Bigal et al.
U.S. Appl. No. 14/711,705, filed May 13, 2015, Bigal et al.
U.S. Appl. No. 15/081,681, filed Mar. 25, 2016, Poulsen et al.
U.S. Appl. No. 15/147,265, filed May 5, 2016, Zeller et al.
U.S. Appl. No. 60/753,044, filed Dec. 22, 2005, Benschop et al.
Abstracts of the XII Congress of the International Headache Society, IHC 2005, Oct. 9-12, 2005, Cephalalgia 25:923, Oct. 9-12, 2005.
Adam et al., "Severity of mucosal inflammation as a predictor for alterations of visceral sensory function in a rat model," Pain 123(1-2):179-86, Jul. 2006.
Adwanikar et al., "Spinal CGRP1 receptors contribute to supraspinally organized pain behavior and pain-related sensitization of amygdala neurons," Pain 132(1-2):53-66, Nov. 2007.
Ahn and Goadsby, "Animal Models of Headache," The Headaches 213-219 2006, 2013.
Aiyar et al., "Pharmacology of SB-273779, a nonpeptide calcitonin gene-related peptide 1 receptor antagonist," J Pharmacolog Exp Therap 296(3):768-775, 2001.
Al-Lazikani et al., "Standard conformations for the canonical structures of immunoglobulins," J Mol Biol 273(4):927-948, Nov. 7, 1997.
Almagro and Strohl, "Antibody engineering: humanization, affinity maturation, and selection technique," Therapeutic Monoclonal Antibodies Chapter 13, pp. 311-334, 2009.
Amara et al., "Expression in brain of a messenger RNA encoding a novel neuropeptide homologous to calcitonin gene-related peptide," Science 229(4718):1094-1097, Sep. 13, 1985.
Ambalavanar et al., "Deep tissue inflammation upregulates neuropeptides and evokes nociceptive behaviors which are modulated by a neuropeptide antagonist," Pain 120(1-2):53-68, Jan. 2006.
American Academy of Neurology, "New Drugs Offer Hope for Migraine Prevention," Apr. 22, 2014.
American Headache Society, "Initial Results for LY2951742, A New Investigational Medicine for Migraine Prevention," 2014. Available at http://www.americanheadachesociety.org/initial_results_for_ly2951742_a_new_investigational_medicine_for_migraine_prevention. Accessed May 15, 2014.

(56) References Cited

OTHER PUBLICATIONS

A study of LY2951742 in Participants with Episodic Cluster Headache, Clinical Trials.gov, last verified Mar. 2016, 6 pages.
An, "Therapeutic Monoclonal Antibodies From Bench to Clinic," Wiley Chapter 31, pp. 711-762, 2009.
Andrew et al., "Monoclonal antibodies distinguishing alpha and beta forms of calcitonin gene-related peptide," J Immunol Methods 134(1):87-94, Nov. 6, 1990.
Armour et al., "Recombinant human IgG molecules lacking Fcγ receptor I binding and monocyte triggering activities," Eur J lmmunol 29(8):2613-2624, Aug. 1999.
Arulmani et al., "Calcitonin gene-related peptide and its role in migraine pathophysiology," Eur J Pharmacol 500(1-3):315-330, Oct. 1, 2004.
Arulmozhi et al., "Migraine: current concepts and emerging therapies," Vascul Pharmacol 43(3):176-187, Sep. 2005.
Asahina et al., "Specific induction of cAMP in Langerhans cells by calcitonin gene-related peptide: Relevance to functional effects," Proceed Nat Acad Sci USA 92(18):8323-8327, 1995.
Ashina et al., "Calcitonin gene-related peptide levels during nitric oxide-induced headache in patients with chronic tension-type headache," Eur J Neurol 8(2):173-178, Mar. 2001.
Ashina et al., "Evidence for increased plasma levels of calcitonin gene-related peptide in migraine outside of attacks," Pain 86(1-2):133-138, May 2000.
Ashina et al., "Plasma levels of calcitonin gene-related peptide in chronic tension-type headache," Neurology 55(9):1335-1340, Nov. 2000.
ATCC website search for PTA-6866 deposit, Jan. 22, 2010, 1 page.
ATCC website search for PTA-6867 deposit, Jan. 22, 2010, 1 page.
Aziz, "Visceral hypersensitivity: fact or fiction," Gastroenterology 131(2):661-664, Aug. 2006.
Balint and Larrick, "Antibody engineering by parsimonious mutagenesis," Gene 137(1):109-118, Dec. 1993.
Bard et al., "Peripherally administered antibodies against amyloid beta-peptide enter the central nervous system and reduce pathology in a mouse model of Alzheimer disease," Nat Med 6(8):916-919, Aug. 2000.
Bell, "Calcitonin Gene-Related Peptide Receptor Antagonists: New Therapeutic Agents for Migraine," J Med Chem 57(19):7838-7858, Jun. 24, 2014.
Bennett et al., "Alleviation of mechanical and thermal allodynia by CGRP(8-37) in a rodent model of chronic central pain," Pain 86(1-2):163-175, May 2000.
Benschop et al., "Development of a novel antibody to calcitonin gene-related peptide for the treatment of osteoarthritis-related pain," Osteoarthritis Cartilage 22(4):578-585, Apr. 2014.
Bigal et al., "Calcitonin gene-related peptide (CGRP) and migraine current understanding and state of development," Headache 53(8):1230-1244, Sep. 2013.
Bigal et al., "Cardiovascular and hemodynamic parameters in women following prolonged CGRP inhibition using LBR-101, a monoclonal antibody against CGRP," Cephalalgia 34(12):968-976, Oct. 2014.
Bigal et al., "Emerging drugs for Inigraine prophylaxis and treatment," MedGenMed 8(2): 31, 2006.
Bigal et al., "Migraine in the Triptan Era: Progresses achieved, lessons learned and future developments," Arquivos de Neuro-Psiquiatria 67(2-B):559-569, 2009.
Bigal et al., "New Migraine preventive options: an update with pathophysiological considerations," Rev Hosp Clin Fae Med Sao Paulo 57(6):293-298, Nov.-Dec. 2002.
Bigal et al., "Safety and tolerability of LBR-101, a humanized monoclonal antibody that blocks the binding of CGRP to its receptor: Results of the Phase 1 program," Cephalalgia 34(7):483-492, Dec. 23, 2013.
Bird et al., "Single-chain antigen-binding proteins," Science 242(4877):423-426, Oct. 21, 1988.

Boerner et al., "Production of antigen-specific human monoclonal antibodies from in vitro-primed human splenocytes," J Immunol 147(1):86-95, Jul. 1, 1991.
Botox Package Insert 2010, 25 pages.
Bowen et al., "Tumor necrosis factor-alpha stimulation of calcitonin gene-related peptide expression and secretion from rat trigeminal ganglion neurons," J Neurochem 96(1):65-77, Jan. 2006.
Brain and Edvinsson, "Calcitonin Gene-Related Peptide and Other Peptides," The Headaches, Third Edition, pp. 159-164, 2006.
Brain and Grant, "Vascular actions of calcitonin gene-related peptide and adrenomedullin," Physiol Rev 84(3):903-934, Jul. 2004.
Brain, "Calcitonin gene-related peptide (CGRP) antagonists: blockers of neuronal transmission in migraine," Brit J Pharmacol 142(7):1053-1054, Aug. 2004.
Brandes et al., "Topiramate for Migraine Prevention," J Am Med Assoc 291(8):965-973, Feb. 25, 2004.
Brorson et al., "Mutational analysis of avidity and fine specificity of anti-levan antibodies," J Immunol 163(12):6694-6701, Dec. 15, 1999.
Brummell et al., "Probing the combining site of an anti-carbohydrate antibody by saturation-mutagenesis: role of the heavy-chain CDR3 residues," Biochemistry, 32(4):1180-1187, Feb. 2, 1993.
Buckley et al., "The partial inhibition of inflammatory responses induced by capsaicin using the Fab fragment of a selective calcitonin gene-related peptide antiserum in rabbit skin," Neuroscience 48(4):963-968, Jun. 1992.
Buntinx et al., "Development of anti-migraine therapeutics using the capsaicin-induced dermal blood flow model," Brit J Clin Pharmacol 80(5):992-4000, Oct. 6, 2015.
Burks et al., "In vitro scanning saturation mutagenesis of an antibody binding pocket," Proc Natl Acad Sci USA 94(2):412-417, Jan. 21, 1997.
Burstein and Jakubowski, "Analgesic Triptan Action in an Animal Model of Intracranial Pain: A Race against the Development of Central Sensitization," Ann Neurol 55(1):27-36, Jan. 2004.
Burstein et al., "Defeating Migraine Paine with Triptans: A Race against the Development of Cutaneous Allodynia," Ann Neurol 55(1):19-26, Jan. 2004.
Capel et al., "Heterogeneity of human IgG Fc receptors," Immunomethods 4(1):25-34, Feb. 1994.
Caraceni et al., "Pain measurement tools and methods in clinical research in palliative care: recommendations of an Expert Working Group of the European Association of Palliative Care," J Pain Symptom Manage 23(3):239-255, Mar. 2002.
Carter, "Potent antibody therapeutics by design," Nature Reviews Immunology 6(5):343-57, May 2006.
Casset et al., "A peptide mimetic of an anti-CD4 monoclonal antibody by rational design," Biochem Biophys Res Commun 307(1):198-205, Jul. 18, 2003.
Cervero et al., "Visceral pain," Lancet 353(9170):2145-2148, Jun. 19, 1999.
Chen et al., "Generation and analysis of random point mutations in an antibody CDR2 sequence: many mutated antibodies lose their ability to bind antigen," J Exp Med 176(3):855-866, Sep. 1992.
Chen et al., "Selection and analysis of an optimized anti-VEGF antibody: crystal structure of an affinity-matured Fab in complex with antigen," J Mol Biol 293(4):865-881, Nov. 5, 1999.
Chothia et al., "Conformations of immunoglobulin hypervariable regions," Nature 342(6252):877-883, Dec. 21-28, 1989.
Clynes et al., "Fc receptors are required in passive and active immunity to melanoma," Proc Natl Acad Sci USA 95(2):652-656, Jan. 20, 1998.
Cole et al., "The EBV-hybridoma technique and its application to human lung cancer," Monoclonal Antibodies and Cancer Therapy 27:77-96, 1985.
Colman, "Effects of amino acid sequence changes on antibody-antigen interactions," Res Immunol 145(1):33-36, Jan. 1994.
Conner et al., "Interaction of calcitonin-gene-related peptide with its receptors," Biochem Soc Trans 30(4):451-455, Aug. 2002.
Correia, "Stability of IgG isotypes in serum," mAbs 2(3):221-232, May/Jun. 2010.

(56) References Cited

OTHER PUBLICATIONS

Covell et al., "Pharmacokinetics of monoclonal immunoglobulin G1, F(ab')2, and Fab' in mice," Cancer Res 46(8):3969-3978, Aug. 1986.
Davies and Riechmann, "Affinity improvement of single antibody VH domains: residues in all three hypervariable regions affect antigen binding," Immunotechnology 2(3):169-179, Sep. 1996.
Davletov et al., "Beyond BOTOX: advantages and lilnitations of individual botulinum neurotoxins," Trends Neurosci 28(8):446-452, Aug. 2005.
De Haas et al., "Fc gamma receptors of phagocytes," J Lab Clin Med 126(4):330-341, Oct. 1995.
De Pascalis et al., "Grafting of "abbreviated" complementarity-determining regions containing specificity-determining residues essential for ligand contact to engineer a less immunogenic humanized monoclonal antibody," J Immunol 169(6):3076-3084, Sep. 15, 2002.
Declaration Dr. Jes Olesen No. 2, dated Feb. 7, 2016, 15 pages.
Declaration Dr. Marcelo Bigal and Dr. Bigal's Cirruculum Vitae, dated Mar. 2, 2015, 41 pages.
Declaration of Dr. Jes Olesen regarding EP1957106, dated Jul. 11, 2014.
Declaration of Dr. Leonard Presta regarding EP1957106, dated Jul. 11, 2014.
Declaration of Dr. Robert Benschop regarding EP1957106, dated Jul. 16, 2014.
Delafoy et al., "Interactive involvement of brain derived neurotrophic factor, nerve growth factor, and calcitonin gene related peptide in colonic hypersensitivity in the rat" Gut 55(7):940-945, Jul. 2006.
Denekas et al. "Inhibition of stimulated meningeal blood flow by a calcitonin gene-related peptide binding mirror-image RNA oligonucleotide," Brit J Pharmacol 148(4):536-543, Jun. 2006.
Dockray et al., "Immunoneutralization studies with calcitonin gene-related peptide," Ann N Y Acad Sci 657:258-267, Jun. 30, 1992.
Dodick et al., "Safety and efficacy of ALD403, an antibody to calcitonin gene-related peptide, for the prevention of frequent episodic migraine: a randomised, double-blind, placebo-controlled, exploratory phase 2 trial," Lancet Neurol 13(11):1100-1107, Nov. 2014.
Dodick et al., "Safety and efficacy of LY2951742, a monoclonal antibody to calcitonin gene-related peptide, for the prevention of migraine: a phase 2, randomised, double-blind, placebo-controlled study," Lancet Neurol 13(9):885-892, Sep. 2014.
Dodick et al., Authors' reply re Site of effect of LY2951742 for migraine prophylaxis. Www.thelancet.com/neueology. vol. 14, 32-33, Jan. 2015.
Dolgin, "Antibody drugs set to revive flagging migraine target," Nat Rev Drug Discov 12(4):249-250, Apr. 2013.
Doods et al., "Pharmacological profile of BIBN4096BS, the first selective small molecule CGRP antagonist," Brit J Pharmacol 129(3):420-423, Feb. 2000.
Dressler et al., "Botulinum toxin: mechanisms of action," Eur Neurol 53(1):3-9, 2005.
Dufner et al., "Harnessing phage and ribosome display for antibody optimisation," Trends Biotechnol 24(11):523-529, Nov. 2006.
Durham et al., "CGRP-receptor antagonists—a fresh approach to migraine therapy?" N Eng J Med 350(11):1073-1075, Mar. 11, 2004.
Edvinsson and Hargreaves, "CGRP Involvement in Migraines," The HeadachesThird Edition, 289-299, 2006.
Edvinsson and Tfelt-Hansen, "The blood-brain barrier in migraine treatment," Cephalalgia 28(12):1245-1258, Dec. 2008.
Edvinsson and Uddman, "Neurobiology in primary headaches," Brain Res Rev 48(3):438-456, Jun. 2005.
Edvinsson et al., "Effect of the CGRP receptor antagonist BIBN4096BS in human cerebral., coronary and omental arteries and in SK-N-MC cells," Eur J Pharmacol 434(1-2):49-53, Jan. 2, 2002.

Edvinsson et al., "Inhibitory effect of BIBN4096BS, CGRP(8-37), a CGRP antibody and an RNA-Spiegelmer on CGRP induced vasodilatation in the perfused and non-perfused rat middle cerebral artery," Brit J Pharmacol 150(5):633-640, Mar. 2007.
Edvinsson et al., "Inhibitory effect of BIBN4096BS, CGRP8-37, a CGRPantibody and an RNA-Spiegelmer on CGRP induced vasodilatation in the perfused and non-perfused rat middle cerebral artery," Brit J Pharmacol 150(5):633-640, Mar. 2007.
Edvinsson, "Blockade of CGRP receptors in the intracranial vasculature: a new target in the treatment of headache," Cephalalgia 24:611-622, 2004.
Edvinsson, "CGRP blockers in migraine therapy: where do they act?" Brit J Pharmacol 155(7):967-969, Dec. 2008.
Edvinsson, "CGRP receptor antagonists and antibodies against CGRP and its receptor in migraine treatment," Brit J Clin Pharmacol 80(2):193-199, Aug. 2015.
Edvinsson, "Clinical Data on the CGRP Antagonist BIBN4096BS for Treatment of Migraine Attacks," CNS Drug Reviews 11(1):69-76, Mar. 2005.
Elshourbagy et al., "Molecular cloning and characterization of the porcine calcitonin gene-related peptide receptor," Endocrinology 139(4):1678-1683, Apr. 1998.
Escott and Brain, "Effect of a calcitonin gene-related peptide antagonist ($CGRP_{8-37}$) on skin vasodilatation and oedema induced by stimulation of the rat saphenous nerve," Brit J Pharmacol 110(2):772-776, Oct. 1993.
Escott et al., "Trigeminal ganglion stimulation increases facial skin blood flow in the rat: a major role for calcitonin gene-related peptide," Brain Res 669(1):93-99, Jan. 9, 1995.
European Notice of Opposition in European Patent No. 1957106, dated Jul. 11, 2014, 56 pages.
European Notice of Opposition in European Patent No. 1957106, dated Jul. 16, 2014, 51 pages.
European Office Action in Application No. 10754584, dated Dec. 16, 2013, 6 pages.
European Search Report in Application No. 11166787.9, dated May 8, 2012, 7 pages.
Evidence of Publication Date of Edvinsson, CNS Drug Reviews 11(1):69-76, 2005.
Extended European Search Report in Application No. 16154411.9, dated Jul. 18, 2016, 8 pages.
Extended European Search Report in Application No. 16154418.4, dated May 10, 2016, 8 pages.
Extended European Search Report in Application No. 17152503.3, dated May 3, 2017, 13 pages.
Fanciullacci et al., "Increase in plasma calcitonin gene-related peptide from the extracerebral circulation during nitroglycerin-induced cluster headache attack," Pain 60(2):119-123, Feb. 1995.
Felson et al., "The American College of Rheumatology preliminary core set of disease activity measures for rheumatoid arthritis clinical trials. The Committee on Outcome Measures in Rheumatoid Arthritis Clinical Trials," Arthritis Rheum 36(6):729-740, Jun. 1993.
Fischer et al., "The Nonpeptide Calcitonin Gene-Related Peptide Receptor Antagonist BIBN4096BS Lowers the Activity of Neurons with Meningeal Input in the Rat Spinal Trigeminal Nucleus," J Neurosci 25(25):5877-5883, Jun. 22, 2005.
Forster and Dockray, "The role of calcitonin gene-related peptide in gastric mucosal protection in the rat," Exp Physiol 76(4):623-626, Jul. 1991.
Francis et al., "The irritable bowel severity scoring system: a simple method of monitoring irritable bowel syndrome and its progress," Aliment Pharmacol Ther 11(2):395-402, Apr. 1997.
Fries et al., "The dimensions of health outcomes: the health assessment questionnaire, disability and pain scales," J Rheumatol 9(5):789-793, Sep.-Oct. 1982.
Frobert et al., "A sensitive sandwich enzyme immunoassay for calcitonin gene-related peptide (CGRP): characterization and application," Peptides 20(2):275-284, 1999.
Gallai et al., "Vasoactive peptide levels in the plasma of young migraine patients with and without aura assessed both interictally and ictally," Cephalalgia 15(5):384-390, Oct. 15, 1995.

(56) References Cited

OTHER PUBLICATIONS

Gay et al. "Interleukin-6 genetic ablation protects from trinitrobenzene sulfonic acid-induced colitis in mice," NeuroImmunoModulation 13(2):114-121, 2006.
Geppetti et al., "CGRP and migraine: neurogenic inflammation revisited," J Headache Pain 6(2):61-70, Apr. 2005.
Giamberadino and Marrtelletti, "Emerging drugs for migraine treatment," Expert Opininon 20(1):137-147, 2015.
Giffin et al., "Effect of the adenosine A 1 receptor agonist GR79236 on trigeminal nociception with blink reflex recordings in healthy human subjects," Cephalalgia 23(4):287-292, May 2003.
Goadsby et al., "Migraine—Current Understanding and Treatment," N Eng J Med 346(4):257-270, Jan. 24, 2002.
Goadsby et al., "Vasoactive peptide release in the extracerebral circulation of humans during migraine headache," Ann Neurol 28(2):183-187, Aug. 1990.
Goadsby, "Calcitonin Gene-Related Peptide Antagonists as Treatments of Migraine and Other Primary Headaches," Drugs 65(18):2557-2567, Dec. 2005.
Goadsby, "Can we Develop Neurally Acting Drugs for the Treatment of Migraine?" Nat Rev Drug Discov 4:741-750, Sep. 2005.
Goadsby, "Incredible progress for an era of better migraine care," Nat Rev Neurol 11(11):621-622, Nov. 2015.
Goadsby, "New targets in the acute treatment of headache," Curr Opin Neurol 18(3):283-288, Jun. 2005.
Goadsby, "Pathophysiology of cluster headache: a trigeminal autonomic cephalgia," Lancet Neurology 1:251-257, 2002.
Goadsby, "Therapeutic Prospects for Migraine: Can Paradise Be Regained?" Ann Neurol 74:423-434, Sep. 2013.
Grennan et al., Textbook of Pain, pp. 397-407, 1994.
Gupta et al. "Improvement of the closed cranial window model in rats by intracarotid infusion of signalling molecules implicated in migraine," Cephalalgia 30(1):27-36, Apr. 28, 2009.
Guyer et al., "Immunoglobulin binding by mouse intestinal epithelial cell receptors," J Immunol 117(2):587-593, Aug. 1976.
Hakala et al., "Modelling constrained calcitonin gene-related peptide analogues," Protein Eng 9(2):143-148, Feb. 1996.
Hay et al., "A comparison of the actions of BIBN4096BS and $CGRP_{8-37}$ on CGRP and adrenomedullin receptors expressed on SK-N-MC, L6, col. 29 and Rat 2 cells," Brit J Pharmacol 137(1):80-86, Sep. 2002.
Hay et al., "Determinants of 1-Piperidinecarboxamide, N-[2-[[5-Amino-1[[4-(4-pyridinyl)-1-piperazinyl]carbonyl]pentyl]amino]-1-[(3,5-dibromo-4-hydroxyphenyl)methyl]-2-oxoethyl]-4-(1,4-dihydro-2-oxo-3(2H)-quinazolinyl) (BIBN4096BS) Affinity for Calcitonin Gene-Related Peptide and Amylin Receptors—The Role of Receptor Activity Modifying Protein 1," Mol Pharmacol 70(6):1984-1991, Dec. 2006.
Hay et al., "Pharmacological Discrimination of Calcitonin Receptor: Receptor Activity-Modifying Protein Complexes," Mol Pharmacol 67(5):1655-1665, May 2005.
Ho et al., "CGRP and its receptors provide new insights into migraine pathophysiology," Nat Rev Neurol 6:573-582, Oct. 2010.
Hogue et al., "Pathophysiology and first-line treatment of osteoarthritis," Ann Pharmacother 36(4):679-686, Apr. 2002.
Holm et al., "Functional mapping and single chain construction of the anti-cytokeratin 8 monoclonal antibody TS1," Mol Immunol 44(6):1075-1084, Feb. 2007.
Holman et al., "Human alpha- and beta-CGRP and rat alpha-CGRP are coronary vasodilators in the rat," Peptides 7(2):231-235, Mar.-Apr. 1986.
Holt et al., "Domain antibodies: proteins for therapy," Trends Biotechnol 21(11):484-490, Nov. 2003.
Hong et al., "Pharmacological coupling and functional role for CGRP receptors in the vasodilation of rat pial arterioles," Am J Phsyiol 270(1):H317-H323, Jan. 1, 1996.
Hong et al., "Pharmacological evidence that calcitonin gene-related peptide is implicated in cerebral autoregulation," Am J Physiology—Heart Circ Physiol 266(1):H11-H16, 1994.

Hoogenboom and Winter, "By-passing immunisation. Human antibodies from synthetic repertoires of germline VH gene segments rearranged in vitro," J Mol Biol 227(2):381-388, Sep. 20, 1992.
Hostetler et al., "In Vivo Quantification of Calcitonin Gene-Related Peptide Receptor Occupancy by Telcagepant in Rhesus Monkey and Human Brain Using the Positron Emission Tomography Tracer [11C]MK-4232," J Pharmacol Experim Therapeut 347(2):478-486, Nov. 1, 2013.
Hruby, "Designing Peptide Receptor Agonists and Antagonists," Nat Rev Drug Discov 1:835-858, Nov. 2002.
Hurley, "CGRP Drug Improves Wellness on Headache-Free Days, Study Finds," Neurology Today, p. 31, Jul. 7, 2016.
Huston et al., "Protein engineering of antibody binding sites: recovery of specific activity in an anti-digoxin single-chain Fv analogue produced in *Escherichia coli*," Proc Natl Acad Sci USA 85(16):5879-5883, Aug. 1988.
International Preliminary Report on Patentability in Application No. PCT/IB2006/003181, dated May 14, 2008, 9 pages.
International Search Report and Written Opinion in Application No. PCT/IB2006/003181, dated May 9, 2007.
International Search Report and Written Opinion in Application No. PCT/IB2009/050849, dated Jul. 31, 2009, 6 pages.
International Search Report and Written Opinion in Application No. PCT/IB2009/050852, dated Jul. 29, 2009, 12 pages.
International Search Report and Written Opinion in Application No. PCT/IB2010/053787, dated Nov. 11, 2010, 12 pages.
International Search Report and Written Opinion in Application No. PCT/US2015/021887, dated Jul. 8, 2015, 12 pages.
Janeway and Travers, Immunobiology: The Immune System in Health and Disease, Garland Publishing. p. G-2, 1994.
Jang et al., "The structural basis for DNA binding by an anti-DNA autoantibody," Mol Immunol 35(18):1207-1217, Dec. 1998.
Jansen-Olesen, "Animal Migraine Models for Drug Development: Status and Future Perspectives," CNS Drugs 27(12):1049-1068, Dec. 2013.
Jefferis, "Glycosylation of recombinant antibody therapeutics," Biotechnology Progress, American Institute of Chemical Engineers, 21(1):11-16, Jan. 1, 2005.
Juhasz et al., "NO-induced migraine attack: strong increase in plasma calcitonin gene-related peptide (CGRP) concentration and negative correlation with platelet serotonin release," Pain 106(3):461-470, Dec. 2003.
Juhl et al., "Effect of two novel CGRP-binding compounds in a closed cranial window rat model," Europ J Pharmacol 657(1-2):117-124, Jul. 12, 2007.
Julia and Bueno, "Tachykininergic mediation of viscerosensitive responses to acute inflammation in rats: role of CGRP," Am J Physiol 272(1 Pt 1):G141-G146, Jan. 1997.
Kar et al., "Increased calcitonin gene-related peptide (CGRP), substance P, and EYKephalin immunoreactivities in dorsal spinal cord and loss of CGRP-immunoreactive motoneurons in arthritic rats depend on intact peripheral nerve supply," J Mol Neurosci 3(1):7-18, 1991.
Katz et al., "Measurement of pain," Surg Clin North Am 79(2):231-252, Apr. 1999.
Kawamura et al., "Antinociceptive effect of intrathecally administered antiserum against calcitonin gene-related peptide on thermal and mechanical noxious stimuli in experimental hyperalgesic rats," Brain Res 497(1):199-203, Sep. 11, 1989.
Kipryanov, "Generation of antibody molecules through antibody engineering," Methods Mol Biol 207:3-25, 2003.
Kobayashi et al., "Tryptophan H33 plays an important role in pyrimidine (6-4) pyrimidone photoproduct binding by a high-affinity antibody," Protein Eng 12(10):879-884, Oct. 1999.
Kohler and Milstein, "Continuous cultures of fused cells secreting antibody of predefined specificity," Nature 256(5517):495-497, Aug. 7, 1975.
Kruuse et al., "Plasma levels of cAMP, cGMP and CGRP in sildenafil-induced headache," Cephalalgia 24(7):547-553, Jul. 2004.
Kumar et al., "Molecular cloning and expression of the Fabs of human autoantibodies in *Escherichia coli*. Determination of the

(56) References Cited

OTHER PUBLICATIONS heavy or light chain contribution to the anti-DNA/-cardiolipin activity of the Fab," J Biol Chem 275(45):35129-35136, Nov. 10, 2000.
Kuraishi et al., "Antinociception induced in rats by intrathecal administration of antiserum against calcitonin gene-related peptide," Neurosci Lett 92(3):325-329, Oct. 17, 1988.
Lassen et al., "CGRP may play a causative role in migraine," Cephalalgia 22(1):54-61, Feb. 2002.
Lassen et al., "Comorbidity," Poster Presentations, Cephalagia 23:581-762, 2003.
Lassen et al., "Involvement of calcitonin gene-related peptide in migraine: regional cerebral blood flow and blood flow velocity in migraine patients," J Headache Pain 9(3):151-157, Jun. 2008.
Letter from Patentee's representative dated Feb. 12, 2013.
Levy et al., "Calcitonin Gene-Related Peptide Does Not Excite or Sensitize Meningeal Nociceptors: Implications for the Pathophysiology of Migraine," Annal Neurol 58(5):698-705, Nov. 2005.
Levy et al., "Disruption of communication between peripheral and central trigeminovascular neurons mediates the antimigraine action of 5HT1B/1D receptor agonists," PNAS 101(12):4274-4279, Mar. 23, 2004.
Little et al., "Of mice and men: hybridoma and recombinant antibodies," Immunology Today 21(8):364-370, 2000.
Longstreth et al., "Functional bowel disorders," Gastroenterology 130(5):1480-1491, Apr. 2006.
Louis et al., "Antibodies to calcitonin-gene related peptide reduce inflammation induced by topical mustard oil but not that due to carrageenin in the rat," Neurosci Lett 102(2-3):257-260, Jul. 31, 1989.
Louis et al., "The role of substance P and calcitonin gene-related peptide in neurogenic plasma extravasation and vasodilatation in the rat," Neuroscience 32(3):581-586, 1989.
MacCallum et al., "Antibody-antigen interactions: contact analysis and binding site topography," J Mol Biol 262(5):732-745, Oct. 11, 1996.
Mallee et al., "Receptor activity-modifying protein 1 determines the species selectivity of non-peptide CGRP receptor antagonists," J Biol Chem 277(16):14294-14298, Apr. 19, 2002.
Marks et al., "By-passing immunization. Human antibodies from V-gene libraries displayed on phage," J Mol Biol 222(3):581-597, Dec. 5, 1991.
Marks et al., "By-passing immunization: building high affinity human antibodies by chain shuffling," Biotechnol 10(7):779-783, Jul. 1992.
Marquez de Prado and Russo, "CGRP receptor antagonists: A new frontier of anti-migraine medications," Drug Discov Today Ther Strateg 3(4):593-597, 2006.
Marshall et al., "Human and rat alpha-CGRP but not calcitonin cause mesenteric vasodilatation in rats," Eur J Pharmacol 123(2):217-222, Apr. 16, 1986.
May, "Cluster headache: pathogenesis, diagnosis, and management," Lancet 366:843-855, 2005.
McCafferty et al., "Phage antibodies: filamentous phage displaying antibody variable domains," Nature 348(6301):552-554, Dec. 6, 1990.
McLatchie et al., "RAMPs regulate the transport and ligand specificity of the calcitoninreceptor-like receptor," Nature 393(6683):333-339, May 28, 1998.
Medhurst et al., "A rat model of bone cancer pain," Pain 96(1-2):129-140, Mar. 2002.
Meenan et al., "The arthritis impact measurement scales. Further investigations of a health status measure," Arthritis Rheum 25(9):1048-1053, Sep. 1982.
Mense, "Pathophysiology of low back pain and the transition to the chronic state—experimental data and new concepts," Schmerz 15(6):413-417, Dec. 2001, Article in German.
Merck manual., Pain, 17th Ed. p. 1367, #167. (in Japanese with Engish translation), 1999.

Moore and Salvatore, "Targeting a family B GPCR/RAMP receptor complex: CGRP receptor antagonists and migraine," Brit J Pharmacol 166(1):66-78, Apr. 10, 2012.
Morell et al., "Metabolic properties of IgG subclasses in man," J Clin Invest 49(4):673-680, Apr. 1970.
Mulderry et al., "Differential expression of alpha-CGRP and beta-CGRP by primary sensory neurons and enteric autonomic neurons of the rat," Neuroscience 25(1):195-205, Apr. 1988.
Mullins et al., "Characterization of a calcitonin gene-related peptide (CGRP) receptor on mouse bone marrow cells," Regal Pept 49(1):65-72, Nov. 19, 1993 (Abstract only).
Nakamura-Craig and Gill, "Effect of neurokinin A, substance P and calcitonin gene related peptide in peripheral hyperalgesia in the rat paw," Neurosci Lett 124(1):49-51, Mar. 11, 1991.
Notice from the European Patent Office dated Oct. 2, 2015, concerning the staying of proceedings due to referral G 1/15, 2 pages.
Olesen and Ashina, "Emerging migraine treatments and drug targets," Trends Pharmacol Sci 32(6):352-359, Jun. 2011.
Olesen and Hargreaves, "CGRP Involvement in Migraines," The Headaches, Lippincott Williams & Wilkins, Chapter 31, pp. 289-299, Oct. 1, 2005.
Olesen et al., "Calcitonin gene-related peptide receptor antagonist BIBN 4096 BS for the acute treatment of migraine," N Eng J Med 350(11):1104-1110, Mar. 11, 2004.
Olesen et al., "Origin of pain in migraine: evidence for peripheral sensitisation," Lancet Neruol 8(7):679-690, Jul. 2009.
Olesen, "The treatment of acute migraine," Rev Neurol (Paris) 161(6-7):679-680, Jul. 2005.
Papadopoulos et al., "Binding and neutralization of vascular endothelial growth factor (VEGF) and related ligands by VEGF Trap, ranibizumab and bevacizumab," Angiogenesis 15(2):171-185, Jun. 2012.
Paulus et al., "Analysis of improvement in individual rheumatoid arthritis patients treated with disease-modifying antirheumatic drugs, based on the findings in patients treated with placebo. The Cooperative Systematic Studies of Rheumatic Diseases Group," Arthritis Rheum 33(4):477-484, Apr. 1990.
Peroutka, "Neurogenic Inflammation and Migraine: Implications for Therapeutics," Mol Interv 5(5):304-311, Oct. 2005.
Peskar et al., "A monoclonal antibody to calcitonin gene-related peptide abolishes capsaicin-induced gastroprotection," Eur J Pharmacol 250(1):201-203, Nov. 30, 1993.
Petersen et al., "BIBN4096BS Antagonizes Human α-calcitonin Gene Related Peptide-induced Headache and Extracerebral Artery Dilatation," Clin Pharmacol Ther 77(3):202-213, Mar. 7, 2005.
Petersen et al., "Inhibitory effect of BIBN4096BS on cephalic vasodilatation induced by CGRP or transcranial electrical stimulation in the rat," Brit J Pharmacol 143(6):697-704, Nov. 2004.
Petersen et al., "Presence and function of the calcitonin gene-related peptide receptor on rat pial arteries investigated in vitro and in vivo," Cephalalgia 25(6):424-432, Jun. 2005.
Petersen et al., "The CGRP-antagonist, BIBN4096BS does not affect cerebral or systemic haemodynamics in healthy volunteers," Cephalalgia 25(2):139-147, Feb. 2005.
Petersen et al., "The effect of the nonpeptide CGRP-antagonist, BIBN4096BS on human-alpha CGRP induced headache and hemodynamics in healthy volunteers," Cephalagia 23:725, 2003.
Plessas et al., "Migraine-like episodic pain behavior in a dog: can dogs suffer from migraines?" J Vet Intern Med 27(5):1034-1040, Sep.-Oct. 2013.
Plourde et al., "Calcitonin gene-related peptide in viscerosensitive response to colorectal distension in rats," Am J Physiol 273(1 Pt 1):G191-G196, Jul. 1997.
Plourde et al., "CGRP antagonists and capsaicin on celiac ganglia partly prevent postoperative gastric ileus," Peptides 14(6):1225-1229, Nov.-Dec. 1993.
Poyner et al., "Structural determinants for binding to CGRP receptors expressed by human SK-N-MC and col. 29 cells: studies with chimeric and other peptides," Brit J Pharmacol 124(8):1659-1666, Aug. 1998.
Prewett et al., "The biologic effects of C225, a chimeric monoclonal antibody to the EGFR, on human prostate carcinoma," J Immunother Emphasis Tumor Immunol 19(6):419-427, Nov. 1996.

(56) References Cited

OTHER PUBLICATIONS

Ravetch et al., "Fc receptors," Annu Rev Immunol 9:457-492, 1991.
Reinshagen et al., "Calcitonin gene-related peptide mediates the protective effect of sensory nerves in a model of colonic injury," J Pharmacol Exp Ther 286(2):657-661, Aug. 1998.
Reuter et al., "Experimental models of migraine," Funct Neurol 15(S3):9-18, 2000.
Roon et al., "No Acute Antimigraine Efficacy of CP-122,288, a Highly Potent Inhibitor of Neurogenic Inflammation: Results of Two Randomized, Double-Blind, Placebo-Controlled Clinical Trials," Ann Neurol 47(2):238-241, Feb. 2000.
Rovero et al., "CGRP Antagonist Activity of Short C-Terminal Fragments of Human aCGRP, CGRP(23-37) and CGRP(19-37)," Peptides 13(5):1025-1027, Sep.-Oct. 1992.
Rozen, "Cluster headache: diagnosis and treatment," Curr Pain Headache Rep 2005;9:135-40.
Rudikoff et al., "Single amino acid substitution altering antigen-binding specificity," Proc Natl Acad Sci USA 79(6):1979-1983, Mar. 1982.
Russell et al., "Calcitonin Gene-related paptide: physiology and pathophysiology," Physiolog Rev 94(4):1099-1142, Oct. 1, 2014.
Saleh et al., "Phase I trial of the chimeric anti-GD2 monoclonal antibody ch14.18 in patients with malignant melanoma," Hum Antibodies Hybridomas 3(1):19-24, Jan. 1992.
Schaible et al., "Mechanisms of pain in arthritis," Ann N Y Acad Sci 966:343-354, Jun. 2002.
Seong et al., "Radiation-induced alteration of pain-related signals in an animal model with bone invasion from cancer," Ann N Y Acad Sci 1030:179-186, Dec. 2004.
Shaw et al., "The effect of monoclonal antibodies to calcitonin gene-related peptide (CGRP) on CGRP-induced vasodilatation in pig coronary artery rings," Brit J Pharmacol 106:196-198, 1992.
Sheets et al., "Efficient construction of a large nonimmune phage antibody library: the production of high-affinity human single-chain antibodies to protein antigens," Proc Natl Acad Sci USA 95(11):6157-6162, May 26, 1998.
Silberstein, "Emerging target-based paradigms to prevent and treat migraine," Clin Pharmacol Ther 93(1):78-85, Jan. 2013.
Smith et al., "Reversal of advanced digoxin intoxication with Fab fragments of digoxin-specific antibodies," N Eng J Med 294(15):797-800, Apr. 8, 1976.
Smith-Gill et al., "Contributions of immunoglobulin heavy and light chains to antibody specificity for lysozyme and two haptens," J Immunol 139(12):4135-4144, Dec. 15, 1987.
Song et al., "Light chain of natural antibody plays a dominant role in protein antigen binding," Biochem Biophys Res Commun 268(2):390-394, Feb. 16, 2000.
Storer et al., "Calcitonin gene-related peptide (CGRP) modulates nociceptive trigeminovascular transmission in the cat," Brit J Pharmacol 142(7):1171-1181, Aug. 2004.
Szabat et al., "Production and characterization of monoclonal antibody against human calcitonin gene-related peptide (CGRP) and its immunohistochemical application to salivary glands," Histochemical Journal 26:317-326, 1994.
Takhshid et al., "Characterization and effects on cAMP accumulation of adrenomedullin and calcitonin gene-related peptide (CGRP) receptors in dissociated rat spinal cord cell culture," Brit J Pharmacol 148(4):459-468, Jun. 2006.
Tamura et al., "Structural correlates of an anti carcinoma antibody: identification of specificity-determining residues (SD Rs) and development of a minimally immunogenic antibody variant by retention ofSDRs only," J Immunol 164(3):1432-1441, Feb. 1, 2000.
Tan et al., "Calcitonin gene-related peptide as an endogenous vasodilator: immunoblockade studies in vivo with an anti-calcitonin gene-related peptide monoclonal antibody and it's Fab' fragment," Clinical Science 89(6):565-573, Dec. 1, 1995.
Tan et al., "Demonstration of the neurotransmitter role of calcitonin gene-related peptides (CGRP) by immunoblockade with anti-CGRP monoclonal antibodies," Brit J Pharmacol 111(3):703-710, Mar. 1994.
Tepper et al., "Botulinum neurotoxin type A in the preventive treatment of refractory headache: a review of 100 consecutive cases," Headache 44(8):794-800, Sep. 2004.
Teva Press Release, "Teva to Aquire Labrys Biologies, Inc.: Novel Migraine Prophylaxis Treatment Adds Significant New Dimension to Teva's growing Pain Care Franchise," RSS Content 2014, 4 pages.
Textbook of Pain Levine et al., Textbook of Pain pp. 45-56, 1994.
Textbook of Pain McCarthy et al., Textbook of Pain pp. 387-395, 1994.
Tfelt-Hansen and Olesen, "Possible site of action of CGRP antagonists in migraine," Cephalalgia 31(6):748-750, Apr. 2011.
Tfelt-Hansen, "Site of effect of LY2951742 for migraine prophylaxis," Lancet Neurol 14(1):31-32, Jan. 2015.
Tfelt-Hansen, "Site of effect of LY2951742 for migraine prophylaxis," The Lancet 14:31-33, Jan. 2015, (includes Authors' reply).
Tvedskov et al., "CGRP receptor antagonist olcegepant (BIBN4096BS) does not prevent glyceryl trinitrate-induced migraine," Cephalalgia 30(11):1346-1353, Nov. 2010.
Tvedskov et al., "No increase of calcitonin gene-related peptide in jugular blood during migraine," Ann Neurol 58(4):561-568, Oct. 2005.
Tvedskov et al., "The prophylactic effect of valproate on glyceryltrinitrate induced migraine," Cephalalgia 24(7):576-585, Jul. 2004.
Tzabazis et al., "Antihyperalgesic effect of a recombinant herpes virus encoding antisense for calcitonin gene-related peptide," Anesthesiology 106(6):1196-4203, Jun. 2007.
Vajdos et al., "Comprehensive functional maps of the antigen-binding site of an anti-ErbB2 antibody obtained with shotgun scanning mutagenesis," J Mol Biol 320(2):415-428, Jul. 5, 2002.
Vater and Klussmann, "Toward third-generation aptamers: Spieglemers and their therapeutic prospects," Curr Opin Drug Discov & Devel 6(2):253-261, Mar. 2003.
Vater et al., "Short bioactive Spiegelmers to migraine-associated calcitonin gene-related peptide rapidly identified by a novel approach: tailored-SELEX," Nucleic Acids Res 31(21):e130, Nov. 1, 2003.
Vaughan et al., "Human antibodies with sub-nanomolar affinities isolated from a large non-immunized phage display library," Nat Biotechnol 14(3):309-314, Mar. 1996.
Vecsei et al. "CGRP antagonists and antibodies for the treatment of migraine," Expert opinion on investigational drugs 24(1):31-41, Jan. 2, 2015.
Vincent et al., "Molecular targets for autoimmune and genetic disorders of neuromuscular transmission," Eur J Biochem 267(23):6717-6728, Dec. 2000.
Vollbracht et al., "The pipeline in headache therapy," CNS Drugs 27(9):717-729, Sep. 2013.
Wacnik et al., "Tumor-induced mechanical hyperalgesia involves CGRP receptors and altered innervation and vascularization of DsRed2 fluorescent hindpaw tumors," Pain 115(1-2):95-106, May 2005.
Waeber et al., "Migraine as an inflammatory disorder," Neurology 64:S9-S15, 2005.
Walter et al., "Evaluation of cardiovascular parameters in cynomolgus monkeys following IV administration of LBR-101, a monoclonal antibody against calcitonin gene-related peptide," MAbs 6(4):871-878, Jul.-Aug. 2014.
Walter et al., "TEV-48125: a review of a monoclonal CGRP antibody in development for the preventive treatment of migraine," Curr Pain Headache Rep 19(3):6, Mar. 2015.
Ward et al., "Binding activities of a repertoire of single immunoglobulin variable domains secreted from *Escherichia coli*," Nature 341(6242):544-546, Oct. 12, 1989.
Wick et al., "Transient receptor potential vanilloid 1, calcitonin gene-related peptide, and substance P. mediate nociception in acute pancreatitis," Am J Physiol Gastrointest Liver Physiol 290(5):G959-G969, May 2006.

(56) References Cited

OTHER PUBLICATIONS

Williamson et al., "Intravital microscope studies on the effects of neurokinin agonists and calcitonin gene-related peptide on dural vessel diameter in the anaesthetized rat," Cephalalgia 17(4):518-524, Jun. 1997.
Williamson et al., "Sumatriptan inhibits neurogenic vasodilation of dural blood vessels in the anaesthetized rat—intravital microscope studies," Cephalalgia 17(4):525-531, Jun. 1997.
Winkler et al., "Changing the antigen binding specificity by single point mutations of an anti-p24 (HIV-1) antibody," J Immunol 165(8):4505-4514, Oct. 15, 2000.
Witte, "The madness of migraine," Scientific American Mind 39-43, Dec. 2006-Jan. 2007.
Wong et al., "Monoclonal antibody to rat alpha-CGRP: production, characterization, and in vivo immunoneutralization activity," Hybridoma 12(1):93-106, Feb. 1993.
Wong et al., "Preparation of a monoclonal antibody to rat alpha-CGRP for in vivo immunoneutralization of peptides," Ann N Y Acad Sci 657:525-527, Jun. 30, 1992.
Wu et al., "Development and potential of non-peptide antagonists for calcitonin-gene-related peptide (CGRP) receptors: evidence for CGRP receptor heterogeneity," Biochem Soc Trans 30(4):468-473, Aug. 2002.
Wu et al., "Humanization of a murine monoclonal antibody by simultaneous optimization of framework and CDR residues," J Mol Biol 294(1):151-162, Nov. 19, 1999.
Xu, "Study on the Mechanism of SP and CGRP in the Chronic Pain and Knee Joint," Master Thesis. Guangxi Medical University. May 2005. (In Chinese with Engish abstract).
Zeller et al., "CGRP function-blocking antibodies inhibit neurogenic vasodilatation without affecting heart rate or arterial blood pressure in the rat," Brit J Pharmacol 155(7):1093-1103, Dec. 2008.
Zhang et al., "Rheumatoid factor specificity of a VH3-encoded antibody is dependent on the heavy chain CDR3 region and is independent of protein A binding," J Immunol 161(5):2284-2289, Sep. 1, 1998.
Zhang et al., "Sensitization of calcitonin gene-related peptide receptors by receptor activity-modifying protein-1 in the trigeminal ganglion," J Neurosci 27(10):2693-2703, Mar. 7, 2003.
Zittel et al. "Role of spinal afferents and calcitonin gene-related peptide in the postoperative gastric ileus in anesthetized rats," Ann Surg 219(1):79-87, Jan. 1994.
Brody et al., "Aptamers as therapeutic and diagnostic agents," Reviews in Molecular Biotechnology 74(1):5-13, Mar. 2000.
Declaration of Dr. Jes Olesen No. 3 regarding EP1957106, dated Jun. 12, 2017.
Declaration of Dr. Leonard Presta No. 2, regarding EP1957106, dated Jun. 12, 2017.
Hershey et al., "Investigation of the species selectivity of a nonpeptide CGRP receptor antagonist using a novel pharmacodynamic assay," Regulatory Peptides 127(1):71-77 Apr. 2005.
Van Wijngaarden et al, "Inhibitors of Ocular Neovascularization: Promises and Potential Problems," JAMA, American Medical Association 293(12):1509-1513, Mar. 2005.
Ashina, "Calcitonin Gene-Related Peptide in Tension-Type Headache," The Scientific World 2:1527-1531, 2002.
Boyce and Hill, "Substance P (NK1) Receptor Antagonists—Analgesics or Not?" Handbook of Experimental Pharmacology Stress, Immunology and Behaviour.
Brown and Morice, "Clinical Pharmacology of Vasodilator Peptides," Jornal of Cardiovascular Pharmacology 10(Suppl. 12):S82-S87, 1987.
Cumberbatch et al., "Dural vasodilation causes a sensitization of rat caudal trigeminal neurones in vivo that is blocked by a 5-HT1B/1D agonist," British Journal of Pharmacology 126:1478-1486, 1999.
Dennis et al., "Structure-Activity Profile of Calcitonin Gene-Related Peptide in Peripheral and Brain Tissues. Evidence for Receptor Multiplicity," The Journal of Pharmacology and Experimental Therapeutics 251(2):718-725, 1989.
Di Angelantonio et al., "A Novel Class of Peptides with Facilitating Action on Neuronal Nicotinic Receptors of Rat Chromaffin Cells in Vitro: Functional and Molecular Dynamic Studies," Molecular Pharmacology 61(1):43-54, 2002.
Edvinsson et al. "Characterisation of the effects of a non-peptide CGRP receptor antagonist in SK-N-MC cells and isolated human cerebral arteries," European Journal of Pharmacology 415:39-44, 2001.
Ferro et al., "A comparison of the contractile effects of 5-hydroxytryptamine, sumatriptan and MK-462 on human coronary artery in vitro," Br J Clin Pharmacol 40:245-251, 1995.
Gardiner et al., "Haemodynamic effects of human $\alpha$-calcitonin gene-related peptide following administration of endothelin-1- or NG-nitro-L-arginine methyl ester in conscious rats," Br J Pharmacol 103:1256-1262, 1991.
Gardiner et al., "Regional haemodynamic effects of human $\alpha$- and $\beta$-calcitonin gene-related peptide in conscious Wistar rats," Br J Pharmacol 98:1225-1232, 1989.
Gardiner et al., "Regional hemodynamic effects of calcitonin gene-related peptide," Am J Physiol 256(25):R332-R338, 1989.
Hay et al., "CGRP modulation by RAMPS," Pharmacology and Therapeutics 109:173-197, 2006.
Hay et al., "International Union of Pharmacology. LXIX. Status of the Calcitonin Gene-Related Peptide Subtype 2 Receptor," Pharmacological Reviews 60(2):143-145, 2008.
Haydon and Carmignoto, "Astrocyte Control of Synaptic Transmission and Neurovascular Coupling," Physiol Rev 86:1009-1031, 2006.
Hill, "NK1 (substance P) receptor antagonists—why are they not analgesic in humans?," TiPS 21:244-246, Jul. 2000.
Hoare, "Mechanisms of peptide and nonpeptide ligand binding to Class B G-protein-coupled receptors," Drug Discovery Today 10(6):417-427, Mar. 2005.
Hoelig et al., "A novel CGRP-neutralizing Spiegelmer attenauates neurogenic plasma protein extravasation," British Journal of Pharmacology 172:3086-3098, 2015.
Lipton et al., "The role of headache-related disability in migraine management," Neurology 56(Supp 1):S35-S42, 2001.
Longmore et al., "5-HT1D receptor agonists and human coronary artery reactivity in vitro" crossover comparisons of 5-HT and sumatriptan with rizatriptan and L-741,519, Br J Clin Pharmacol 42:431-441, 1996.
Longmore et al., "Comparison of the vasoconstrictor effects of the selective 5-HT1D-receptor agonist L-775,606 with mixed 5-HT1B/1D-receptor agonist sumatritan and 5-HT in human isolated coronary artery," J Clin Pharmacol 49:126-131, 2000.
McCulloch et al., "Calcitonin gene-related peptide: Functional role in cerebrovascular regulation," Proc Natl Acad Sci USA 83:5731-5735, Aug. 1986.
Morara et al., "Calcitonin Gene-Related Peptide Receptor Expression in the Neurons and Glia of Developing Rat Cerebellum: An Autoradiographic and Immunohistochemical Analysis," Neuroscience 100(2):381-391, 2000.
O'Connell et al., "On the role of the C-terminus of $\alpha$-calcitonin-gene-related peptide (aCGRP) The Structure of des-phenylalaninamide$^{37}$-$\alpha$CGRP and its interaction with the CGRP receptor," Biochem J 291:205-210, 1993.
Poyner et al., "Calcitonin gene-related peptide: multiple actions, multiple receptors," Pharmac Ther 56:23-51, 1992.
Ramadan and Buchanan, "New and future migraine therapy," Pharmacology and Therapeutics 112:199-212, 2006.
Reuter, "Anti-CGRP antibodies: a new approach to migraine prevention," The Lancet 13(9):857-859, Sep. 2014.
Sandor, "Nervous control of the cerebrovascular system: doubt and facts," Neurochemistry International 35:237-259, 1999.
Schueren et al., "Reproducibility of the capsaicin-induced dermal blood flow response as assessed by laser Doppler perfusion imaging," Br J Clin Pharmacol 64(5):580-590, 2007.
Seon et al., "Isolation, Structure, Synthesis, and Activity of a New Member of the Calcitonin Gene-related Peptide Family from Frog

(56) References Cited

OTHER PUBLICATIONS

Skin and Molecular Cloning of Its Precursor," The Journal of Biological Chemistry 275(8):5934-5940, 2000.

Shawket et al., "Prolonged effect of CGRP in Raynaud's patients: a double-blind randomised comparison with prostacyclin," Br J Clin Pharmac 32:209-213, 1991.

Shawket et al., "Selective Suprasensitivity to Calcitonin-Gene-Related Peptide in the Hands in Raynaud's Phenomenon," The Lancet 1354-1385, Dec. 9, 1989.

Smith et al., "An immunocytochemical investigation of human trigeminal nucleus caudalis: CGRP, substance P and 5-HT1D-receptor immunoreactivities are expressed by trigeminal sensory fibres," Cephalalgia 22:242-432, 2002.

Sternini, "Enteric and Visceral Afferent CGRP Neurons, Targets of Innervation and Differential Expression Patterns," Annals New York Academy of Sciences 170-185, 1992.

Struthers et al., "Human calcitonin gene related peptide: a potent endogenous vasodilator in man," Clinical Science 70:389-393, 1986.

Swillens, "Interpretation of Binding Curves Obtained with High Receptor Concentrations: Practical Aid for Computer Analysis," Molecular Pharmacology 47:1197-1203, 1995.

Troltzsch et al., "The calcitonin gene-related peptide (CGRP) receptor antagonist BIBN4096BS reduces neurogenic increases in dural blood flow," European Journal of Pharmacology 562:103-110, 2007.

Wimalawansa et al., "Isolation, Purification, and Characterization of Calcitonin Gene-Related Peptide Receptor," Peptides 14:691-699, 1993.

Wimalawansa, "Cacitonin Gene-Related Peptide and Its Receptors: Molecular Genetics, Physiology, Pathophysiology, and Therapeutic Potentials," Endocrine Reviews 17(5):553-585, Oct. 1996.

Wisskitchen et al., "Bioactive β-bend structures for the antagonist hα CGRP $_{8-37}$ at the CGRP$_1$ receptor of the rat pulmonary artery," British Journal of Pharmacology 129:1049-1055, 2000.

Figure 1

| Fab | $K_D$ (nM) 1-37 (WT) | $K_D$ (nM) 19-37[a] | $K_D$ (nM) 25-37[a] | F27A | V28A | P29A | T30A | N31A | V32A | G33A | S34A | K35A | F37A |
|---|---|---|---|---|---|---|---|---|---|---|---|---|---|
| 7E9 | 1.0 | 1.1±0.8 | 0.14±0.05 | 1.0 | 1.0 | 26 | 7 | 9 | 41 | 1256 | 69 | 4 | 3598 |
| 8B6 | 1.1 | 1.5±1.2 | 0.45±0.08 | 1.0 | 1.0 | 9 | 2.2 | 3 | 5 | 496 | 26 | 3 | 2527 |
| 10A8 | 2.1 | 2.4±1.4 | 1.0±0.2 | 1.0 | 1.0 | 9 | 4 | 4 | 11 | 36 | 82 | 13 | 2152 |
| 7D11 | 4.4 | 10±7 | 3.4±0.4 | 1.1 | 1.0 | 7 | 4 | 5 | 5 | 86 | 18 | 1.4 | 420 |
| 6H2 | 9.3 | 7.8±0.2 | 8.5±0.5 | 0.9 | 1.0 | 1.0 | 0.8 | 4 | 11 | 14 | 0.5 | 1.0 | |
| 4901 | 60.5 | 52±12 | 296±115 | 0.8 | 0.8 | 0.2 | 0.2 | 0.3 | 0.9 | 1.3 | 0.8 | 0.3 | |
| 14E10 | 79.7 | 91±3 | 117.4±0.7 | 0.8 | 0.8 | 11 | 3 | 18 | 2 | 1 | 3 | 0.4[b] | |
| 9B8 | 84.7 | 76±20 | 96±28 | 0.8 | 0.7 | 0.6 | 0.6 | 0.7 | 0.6 | 1.3 | 4 | 0.4[b] | |
| 13C2 | 94.4 | 86±13 | 137±5 | 0.7 | 0.7 | 0.5 | 0.4 | 0.6 | 0.2 | 0.9 | 1.1 | 0.4[b] | |
| 14A9 | 148.4 | 219±114 | 246±20 | 0.8 | 0.7 | 0.7 | 0.5 | 0.8 | 0.7 | 1.6 | 1.3 | 6 | |
| 6D5 | 209.9 | 207±26 | 378±22 | 0.8 | 0.7 | 0.5 | 0.4 | 0.6 | 0.5 | 3 | 1.1 | 5 | |
| 1C5 | 296.4 | 223±51 | 430±173 | 0.8 | 0.8 | 0.6 | 0.4 | 0.6 | 0.6 | 1.1 | 1.1 | 5 | |

$K_D$ (mutant/parent)

Figure 5

Bold=Kabat CDR
Underline=Chothia CDR

G1 Heavy chain

```
                                                              H1
1         5         10        15        20        25            30
E V Q L V E S G G G L V Q P G G S L R L S C A A S G F T F S
                                                      H2
31        35        40        45        50        55          60
N Y W I S W V R Q A P G K G L E W V A E I R S E S D A S A T 61        65        70        75        80        85          90
H Y A E A V K G R F T I S R D N A K N S L Y L Q M N S L R A
                                    H3
91        95        100       105       110       115         120
E D T A V Y Y C L A Y F D Y G L A I Q N Y W G Q G T L V T V 121 122
S S
```

G1 Light chain

```
                                                              L1
1         5         10        15        20        25            30
E I V L T Q S P A T L S L S P G E R A T L S C K A S K R V T
                                              L2
31        35        40        45        50        55          60
T Y V S W Y Q Q K P G Q A P R L L I Y G A S N R Y L G I P A 61        65        70        75        80        85          90
R F S G S G S G T D F T L T I S S L E P E D F A V Y Y C S Q
      L3
91        95        100       105       107
S Y N Y P Y T F G Q G T K L E I K
```

ANTAGONIST ANTIBODIES DIRECTED AGAINST CALCITONIN GENE-RELATED PEPTIDE

CROSS REFERENCE TO RELATED APPLICATIONS

This application is a continuation of U.S. patent application Ser. No. 15/147,265, filed May 5, 2016, which is a continuation of U.S. patent application Ser. No. 15/044,552 (now U.S. Pat. No. 9,365,648), filed Feb. 16, 2016, which is a continuation of U.S. patent application Ser. No. 14/719,015 (now U.S. Pat. No. 9,328,168), filed May 21, 2015, which is a continuation of U.S. patent application Ser. No. 14/251,925 (now U.S. Pat. No. 9,115,194), filed Apr. 14, 2014, which is a continuation of U.S. patent application Ser. No. 14/086,816 (now U.S. Pat. No. 8,734,802), filed Nov. 21, 2013, which is a continuation of U.S. patent application Ser. No. 13/870,871 (now U.S. Pat. No. 8,597,649), filed Apr. 25, 2013, which is a continuation of U.S. patent application Ser. No. 13/179,846 (now U.S. Pat. No. 8,586,045), filed Jul. 11, 2011, which is a divisional of U.S. patent application Ser. No. 12/093,638 (now U.S. Pat. No. 8,007,794), filed Nov. 10, 2008, which is a national stage entry of PCT International Application No. PCT/IB2006/003181 filed Nov. 2, 2006, which claim priority to U.S. Provisional Patent Application No. 60/736,623, filed Nov. 14, 2005, all of which are incorporated herein in their entireties by reference.

FIELD OF THE INVENTION

The present invention relates to the use of anti-CGRP antagonist antibodies for the prevention, amelioration, or treatment of vasomotor symptoms, such as CGRP related headaches (e.g., migraine) and hot flushes.

BACKGROUND OF THE INVENTION

CGRP (calcitonin gene-related peptide) is a 37 amino acid neuropeptide, which belongs to a family of peptides that includes calcitonin, adrenomedullin and amylin. In humans, two forms of CGRP ($\alpha$-CGRP and $\beta$-CGRP) exist and have similar activities. They vary by three amino acids and exhibit differential distribution. At least two CGRP receptor subtypes may also account for differential activities. CGRP is a neurotransmitter in the central nervous system, and has been shown to be a potent vasodilator in the periphery, where CGRP-containing neurons are closely associated with blood vessels. CGRP-mediated vasodilatation is also associated with neurogenic inflammation, as part of a cascade of events that results in extravasation of plasma and vasodilation of the microvasculature and is present in migraine.

CGRP has been noted for its possible connection to vasomotor symptoms (Wyon et al. Scand. J. Urol. Nephrol. 35: 92-96 (2001); Wyon et al. Menopause 7(1):25-30 (2000)). Vasomotor symptoms (VMS), such as hot flushes and night sweats, are the most common symptoms associated with menopause, occurring in 60% to 80% of all women following natural or surgically-induced menopause. Hot flushes are likely to be an adaptive response of the central nervous system (CNS) to declining sex steroids (Freedman Am. J. Human Biol. 13:453-464 (2001)). To date, the most effective therapies for flushes are hormone-based treatments, including estrogens and/or some progestins. Hormonal treatments can be effective for alleviating flushes, but are not appropriate for all women. Psychological and emotional symptoms observed, such as nervousness, fatigue, irritability, insomnia, depression, memory loss, headache, anxiety, nervousness or inability to concentrate are considered to be caused by the sleep deprivation following hot flush and night sweats (Kramer et al., In: Murphy et al., 3.sup.rd Int'l Symposium on Recent Advances in Urological Cancer Diagnosis and Treatment-Proceedings, Paris, France: SCI: 3-7 (1992)).

Men also experience hot flushes following steroid hormone (androgen) withdrawal. This is true in cases of age-associated androgen decline (Katovich, et al., Proceedings of the Society for Experimental Biology & Medicine, 1990, 193(2): 129-35) as well as in extreme cases of hormone deprivation associated with treatments for prostate cancer (Berendsen, et al., European Journal of Pharmacology, 2001, 419(1): 47-54). As many as one-third of these patients will experience persistent and frequent symptoms severe enough to cause significant discomfort and inconvenience.

CGRP is a potent vasodilator that has been implicated in the pathology of other vasomotor symptoms, such as all forms of vascular headache, including migraines (with or without aura) and cluster headache. Durham, N. Engl. J. Med. 350:1073-1075, 2004. The serum levels of CGRP in the external jugular vein are elevated in patients during migraine headache. Goadsby et al., Ann. Neurol. 28:183-7, 1990. Intravenous administration of human $\alpha$-CGRP induced headache and migraine in patients suffering from migraine without aura, suggesting that CGRP has a causative role in migraine. Lassen et al., Cephalalgia 22:54-61, 2002.

Possible CGRP involvement in migraine has been the basis for the development and testing of a number of compounds that inhibit release of CGRP (e.g., sumatriptan), antagonize at the CGRP receptor (e.g., dipeptide derivative BIBN4096BS (Boerhringer Ingelheim); CGRP(8-37)), or interact with one or more of receptor-associated proteins, such as, receptor activity membrane protein (RAMP) or receptor component protein (RCP), both of which affect binding of CGRP to its receptors. Brain, S. et al., Trends in Pharmacological Sciences 23:51-53, 2002. Alpha-2 adrenoceptor subtypes and adenosine A1 receptors also control (inhibit) CGRP release and trigeminal activation (Goadsby et al., Brain 125:1392-401, 2002). The adenosine A1 receptor agonist GR79236 (metrafadil), which has been shown to inhibit neurogenic vasodilation and trigeminal nociception in humans, may also have anti-migraine activity (Arulmani et al., Cephalalgia 25:1082-1090, 2005; Giffin et al., Cephalalgia 23:287-292, 2003.)

Confounding this theory is the observation that treatment with compounds that exclusively inhibit neurogenic inflammation (e.g., tachykinin NK1 receptor antagonists) or trigeminal activation (e.g., $5HT_{1D}$ receptor agonists) have been shown to be relatively ineffective as acute treatments for migraine, leading some investigators to question whether inhibiting release of CGRP is the primary mechanism of action of effective anti-migraine treatments. Arulmani et al., Eur. J. Pharmacol. 500:315-330, 2004.

Migraine is a complex, common neurological condition that is characterized by severe, episodic attacks of headache and associated features, which may include nausea, vomiting, sensitivity to light, sound or movement. In some patients, the headache is preceded or accompanied by an aura. The headache pain may be severe and may also be unilateral in certain patients.

Migraine attacks are disruptive to daily life. In US and Western Europe, the overall prevalence of migraine sufferers is 11% of the general population (6% males; 15-18% females). Furthermore, the median frequency of attacks in an individual is 1.5/month. While there are a number of treatments available to alleviate or reduce symptoms, preventive therapy is recommended for those patients having more than 3-4 attacks of migraine per month. Goadsby et al. New Engl. J. Med. 346(4): 257-275, 2002.

The variety of pharmacologic interventions that have been used to treat migraine and the variability in responses among patients are a testament to the diverse nature of this disorder. Thus, such relatively non-selective drugs as ergot alkaloids (e.g., ergotamine, dihydroergotamine, methysergide), which exhibit serotonergic, as well as adrenergic, noradrenergic and dopaminergic activity, have been used for over eighty years to treat migraine. Other treatments include opiates (e.g., oxycodone) and β-adrenergic antagonists (e.g., propranolol). Some patients, usually those with milder symptoms, are able to control their symptoms with non-prescription remedies such as one or more non-steroidal anti-inflammatory agents (NSAIDs), such as a combination of aspirin, acetaminophen and caffeine (e.g., Excedrin® Migraine).

More recently, some migraine patients have been treated with topiramate, an anticonvulsant that blocks voltage-dependent sodium channels and certain glutamate receptors (AMPA-kainate), potentiates GABA-A receptor activity, and blocks carbonic anhydrase. The relatively recent success of serotonin 5HT-1B/1D and/or 5HT-1a receptor agonists, such as sumatriptan, in some patients has led researchers to propose a serotonergic etiology of the disorder. Unfortunately, while some patients respond well to this treatment, others are relatively resistant to its effects.

It has been postulated that a dysfunction of an ion channel in the aminergic brainstem nuclei underlies the disorder, however, the precise pathophysiology of migraine is not yet well understood. One form of migraine, familial hemiplagic migraine, has been shown to associated with missense mutations in the α1 subunit of the voltage-gated P/Q-type calcium channel, and it is thought likely that other ion-channel mutations will also be found in other populations of patients. While dilation of blood vessels is associated with and exacerbates the pain symptoms of migraine, such neurovascular events are now thought to be a result of, rather than causative of, the condition. Overall, dysfunction of brainstem pathways modulating sensory input is considered to be a unifying feature of migraine. Goadsby, P. J. et al., New Engl. J. Med. 346(4): 257-275, 2002.

Throughout this application various publications (including patents and patent applications) are referenced. The disclosures of these publications in their entireties are hereby incorporated by reference.

BRIEF SUMMARY OF THE INVENTION

The invention disclosed herein concerns anti-CGRP antagonist antibodies and methods of using anti-CGRP antagonist antibodies for treating or preventing vasomotor symptoms, such as headaches, such as migraine with or without aura, hemiplegic migraine, cluster headaches, migrainous neuralgia, chronic headaches, tension headaches, and headaches resulting from other medical conditions (such as infection or increased pressure in the skull due to a tumor). Other vasomotor symptoms include hot flushes.

In one aspect, the present invention provides a method for treating or preventing at least one vasomotor symptom in an individual comprising administering to the individual an effective amount of an anti-CGRP antagonist antibody.

In one aspect, the present invention provides a method for treating or preventing headache (e.g., migraine and cluster headache) in an individual comprising administering to the individual an effective amount of an anti-CGRP antagonist antibody.

In another aspect, the invention provides a method for ameliorating, controlling, reducing incidence of, or delaying the development or progression of headache (e.g., migraine and cluster headache) in an individual comprising administering to the individual an effective amount of an anti-CGRP antagonist antibody.

In a further embodiment, the invention provides methods for ameliorating, controlling, reducing incidence of, or delaying the development or progression of headache (e.g., migraine and cluster headache) in an individual comprising administering to the individual an effective amount of an anti-CGRP antagonist antibody in combination with at least one additional agent useful for treating headache. Such additional agents include 5-HT1-like agonists (and agonists acting at other 5-HT1 sites), and non-steroidal anti-inflammatory drugs (NSAIDs).

Examples of 5-HT1 agonists that can be used on combination with an anti-CGRP antibody include a class of compounds known as triptans, such as sumatriptan, zolmitriptan, naratriptan, rizatriptan, eletriptan, almotriptan, and frovatriptan. Ergot alkaloids and related compounds are also known to have 5-HT agonist activity and have been used to treat headache such as migraine. Included among these compounds are ergotamine tartrate, ergonovine maleate, and ergoloid mesylates (e.g., dihydroergocornine, dihydroergocristine, dihydroergocryptine, and dihydroergotamine mesylate (DHE 45)).

Examples of NSAIDs that can be used in combination with an anti-CGRP antibody include naproxen, flurbiprofen, ketoprofen, oxaprozin, etodolac, indomethacin, ketorolac, nabumetone, mefanamic acid, and piroxican. Additional NSAIDs include cyclooxygenase-2 (COX-2) inhibitors. Members of this group include: celecoxib; rofecoxib; meloxicam; JTE-522; L-745,337; NS398; and pharmaceutically acceptable salts thereof.

In another aspect, the invention provides a method for ameliorating, controlling, reducing incidence of, or delaying the development or progression of hot flushes in an individual comprising administering to the individual an effective amount of an anti-CGRP antagonist antibody.

In another aspect, the invention provides methods for ameliorating, controlling, reducing incidence of, or delaying the development or progression of hot flushes in an individual comprising administering to the individual an effective amount of an anti-CGRP antagonist antibody in combination with at least one additional agent useful for treating hot flushes. Such additional agents include, but are not limited to, hormone-based treatments, including estrogens and/or progestins.

In one embodiment, the anti-CGRP antagonist antibody used in any of the methods described above is any of the antibodies as described herein.

In some embodiments, the anti-CGRP antagonist antibody recognizes a human CGRP. In some embodiments, the anti-CGRP antagonist antibody binds to both human α-CGRP and β-CGRP. In some embodiments, the anti-CGRP antagonist antibody binds human and rat CGRP. In some embodiments, the anti-CGRP antagonist antibody binds the C-terminal fragment having amino acids 25-37 of CGRP. In some embodiments, the anti-CGRP antagonist antibody binds a C-terminal epitope within amino acids 25-37 of CGRP.

In some embodiments, the anti-CGRP antagonist antibody is a monoclonal antibody. In some embodiments, the anti-CGRP antagonist antibody is humanized. In some embodiments, the antibody is human. In some embodiments, the anti-CGRP antagonist antibody is antibody G1 (as described herein). In some embodiments, the anti-CGRP antagonist antibody comprises one or more CDR(s) (such as one, two, three, four, five, or, in some embodiments, all six CDRs) of antibody G1 or variants of G1 shown in Table 6.

In still other embodiments, the anti-CGRP antagonist antibody comprises the amino acid sequence of the heavy chain variable region shown in FIG. 5 (SEQ ID NO: 1) and the amino acid sequence of the light chain variable region shown in FIG. 5 (SEQ ID NO: 2).

In some embodiments, the antibody comprises a modified constant region, such as a constant region that is immunologically inert (including partially immunologically inert), e.g., does not trigger complement mediated lysis, does not stimulate antibody-dependent cell mediated cytotoxicity (ADCC), does not activate microglia, or having reduced one or more of these activities. In some embodiments, the constant region is modified as described in Eur. J. Immunol. (1999) 29:2613-2624; PCT Application No. PCT/GB99/01441; and/or UK Patent Application No. 9809951.8. In other embodiments, the antibody comprises a human heavy chain IgG2 constant region comprising the following mutations: A330P331 to S330S331 (amino acid numbering with reference to the wildtype IgG2 sequence). Eur. J. Immunol. (1999) 29:2613-2624. In some embodiments, the heavy chain constant region of the antibody is a human heavy chain IgG1 with any of the following mutations: 1) A327A330P331 to G327S330S331; 2) E233L234L235G236 (SEQ ID NO: 48) to P233V234A235 with G236 deleted; 3) E233L234L235 to P233V234A235; 4) E233L234L235G236A327A330P331 (SEQ ID NO: 49) to P233V234A235G327S330S331 (SEQ ID NO: 50) with G236 deleted; 5) E233L234L235A327A330P331 (SEQ ID NO: 51) to P233V234A235G327S330S331 (SEQ ID NO: 50); and 6) N297 to A297 or any other amino acid except N. In some embodiments, the heavy chain constant region of the antibody is a human heavy chain IgG4 with any of the following mutations: E233F234L235G236 (SEQ ID NO: 52) to P233V234A235 with G236 deleted; E233F234L235 to P233V234A235; and S228L235 to P228E235.

In still other embodiments, the constant region is aglycosylated for N-linked glycosylation. In some embodiments, the constant region is aglycosylated for N-linked glycosylation by mutating the oligosaccharide attachment residue (such as Asn297) and/or flanking residues that are part of the N-glycosylation recognition sequence in the constant region. In some embodiments, the constant region is aglycosylated for N-linked glycosylation. The constant region may be aglycosylated for N-linked glycosylation enzymatically or by expression in a glycosylation deficient host cell.

The binding affinity ($K_D$) of an anti-CGRP antagonist antibody to CGRP (such as human α-CGRP as measured by surface plasmon resonance at an appropriate temperature, such as 25 or 37° C.) can be about 0.02 to about 200 nM. In some embodiments, the binding affinity is any of about 200 nM, about 100 nM, about 50 nM, about 10 nM, about 1 nM, about 500 pM, about 100 pM, about 60 pM, about 50 pM, about 20 pM, about 15 pM, about 10 pM, about 5 pM, or about 2 pM. In some embodiments, the binding affinity is less than any of about 250 nM, about 200 nM, about 100 nM, about 50 nM, about 10 nM, about 1 nM, about 500 pM, about 100 pM, or about 50 pM.

The anti-CGRP antagonist antibody may be administered prior to, during and/or after headache. In some embodiments, the anti-CGRP antagonist antibody is administered prior to the attack of headache (e.g., migraine and cluster headache). Administration of an anti-CGRP antagonist antibody can be by any means known in the art, including: orally, intravenously, subcutaneously, intraarterially, intramuscularly, intracardially, intraspinally, intrathoracically, intraperitoneally, intraventricularly, sublingually, transdermally, and/or via inhalation. Administration may be systemic, e.g. intravenously, or localized.

In some embodiments, the anti-CGRP antagonist antibody may be administered in conjunction with an another agent, such as another agent for treating headache.

In another aspect, the invention provides use of an anti-CGRP antagonist antibody for the manufacture of a medicament for use in any of the methods described herein, for example, for treating or preventing headache.

In another aspect, the invention provides a pharmaceutical composition for preventing or treating headache (e.g., migraine and cluster headache) comprising an effective amount of an anti-CGRP antagonist antibody, in combination with one or more pharmaceutically acceptable excipients.

In another aspect, the invention provides a kit for use in any of the methods described herein. In some embodiments, the kit comprises a container, a composition comprising an anti-CGRP antagonist antibody described herein, in combination with a pharmaceutically acceptable carrier, and instructions for using the composition in any of the methods described herein.

The present invention also provides anti-CGRP antagonist antibodies and polypeptides derived from antibody G1 or its variants shown in Table 6. Accordingly, in one aspect, the invention is an antibody G1 (interchangeably termed "G1") that is produced by expression vectors having ATCC Accession Nos. PTA-6866 and PTA-6867. For example, in one embodiment is an antibody comprising a heavy chain produced by the expression vector with ATCC Accession No. PTA-6867. In a further embodiment is an antibody comprising a light chain produced by the expression vector with ATCC Accession No. PTA-6866. The amino acid sequences of the heavy chain and light chain variable regions of G1 are shown in FIG. 5. The complementarity determining region (CDR) portions of antibody G1 (including Chothia and Kabat CDRs) are also shown in FIG. 5. It is understood that reference to any part of or entire region of G1 encompasses sequences produced by the expression vectors having ATCC Accession Nos. PTA-6866 and PTA-6867, and/or the sequences depicted in FIG. 5. The invention also provides antibody variants of G1 with amino acid sequences depicted in Table 6.

In one aspect, the invention is an antibody comprising a $V_H$ domain that is at least 85%, at least 86%, at least 87%, at least 88%, at least 89%, at least 90%, at least 91%, at least 92%, at least 93%, at least 94%, at least 95%, at least 96%, at least 97% at least 98%, at least 99% or 100% identical in amino acid sequence to SEQ ID NO: 1.

In another aspect, the invention is an antibody comprising a $V_L$ domain that is at least 85%, at least 86%, at least 87%, at least 88%, at least 89%, at least 90%, at least 91%, at least 92%, at least 93%, at least 94%, at least 95%, at least 96%, at least 97% at least 98%, at least 99% or 100% identical in amino acid sequence to SEQ ID NO: 2.

In another aspect, the invention is an antibody comprising a fragment or a region of the antibody G1 or its variants shown in Table 6. In one embodiment, the fragment is a light chain of the antibody G1. In another embodiment, the fragment is a heavy chain of the antibody G1. In yet another embodiment, the fragment contains one or more variable regions from a light chain and/or a heavy chain of the antibody G1. In yet another embodiment, the fragment contains one or more variable regions from a light chain and/or a heavy chain shown in FIG. 5. In yet another embodiment, the fragment contains one or more CDRs from a light chain and/or a heavy chain of the antibody G1.

In another aspect, the invention provides polypeptides (which may or may not be an antibody) comprising a $V_H$ CDR3 as set forth in SEQ ID NO: 5, or a sequence that differs from SEQ ID NO: 5 by 1, 2, 3, 4, or 5 amino acid substitutions. In a particular embodiment, such amino acid substitutions are conservative substitutions.

In another aspect, the invention provides polypeptides (which may or may not be an antibody) comprising a $V_L$ CDR3 as set forth in SEQ ID NO: 8, or a sequence that differs from SEQ ID NO: 8 by 1, 2, 3, 4, or 5 amino acid substitutions. In a particular embodiment, such amino acid substitutions are conservative substitutions.

In another aspect, the invention provides polypeptides (which may or may not be an antibody) comprising any one or more of the following: a) one or more CDR(s) of antibody G1 or its variants shown in Table 6; b) CDR H3 from the heavy chain of antibody G1 or its variants shown in Table 6; c) CDR L3 from the light chain of antibody G1 or its variants shown in Table 6; d) three CDRs from the light chain of antibody G1 or its variants shown in Table 6; e) three CDRs from the heavy chain of antibody G1 or its variants shown in Table 6; f) three CDRs from the light chain and three CDRs from the heavy chain of antibody G1 or its variants shown in Table 6. The invention further provides polypeptides (which may or may not be an antibody) comprising any one or more of the following: a) one or more (one, two, three, four, five, or six) CDR(s) derived from antibody G1 or its variants shown in Table 6; b) a CDR derived from CDR H3 from the heavy chain of antibody G1; and/or c) a CDR derived from CDR L3 from the light chain of antibody G1. In some embodiments, the CDR is a CDR shown in FIG. 5. In some embodiments, the one or more CDRs derived from antibody G1 or its variants shown in Table 6 are at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to at least one, at least two, at least three, at least four, at least five, or at least six CDRs of G1 or its variants.

In some embodiments, the CDR is a Kabat CDR. In other embodiments, the CDR is a Chothia CDR. In other embodiments, the CDR is a combination of a Kabat and a Chothia CDR (also termed "combined CDR" or "extended CDR"). In other words, for any given embodiment containing more than one CDR, the CDRs may be any of Kabat, Chothia, and/or combined.

In some embodiments, the polypeptide (such as an antibody) comprises the amino acid sequence of KASKXaaVXaaTYVS (SEQ ID NO: 53), wherein Xaa at position 5 is R, W, G, L, or N; and wherein Xaa at position 7 is T, A, D, G, R, S, W, or V. In some embodiments, the amino acid sequence of KASKXaaVXaaTYVS (SEQ ID NO: 53) is CDR1 of an antibody light chain.

In some embodiments, the polypeptide (such as an antibody) comprises the amino acid sequence of XaaXaaSNRYXaa (SEQ ID NO: 54), wherein Xaa at position 1 is G or A; wherein Xaa at position 2 is A or H; and wherein Xaa at position 7 is L, T, I, or S. In some embodiments, the amino acid sequence of XaaXaaSNRYXaa (SEQ ID NO: 54) is CDR2 of an antibody light chain.

In some embodiments, the polypeptide (such as an antibody) comprises the amino acid sequence of EIRSXaaSDXaaXaaATXaaYAXaaAVKG (SEQ ID NO: 55), wherein Xaa at position 5 is E, R, K, Q, or N; wherein Xaa at position 8 is A, G, N, E, H, S, L, R, C, F, Y, V, D, or P; wherein Xaa at position 9 is S, G, T, Y, C, E, L, A, P, I, N, R, V, D, or M; wherein Xaa at position 12 is H or F; wherein Xaa at position 15 is E or D. In some embodiments, the amino acid sequence of EIRSXaaSDXaaXaaATXaaYAXaaAVKG (SEQ ID NO: 55) is CDR2 of an antibody heavy chain.

In some embodiments, the polypeptide (such as an antibody) comprises the amino acid sequence of SEQ ID NO:1, wherein amino acid residue at position 99 of SEQ ID NO:1 is L or is substituted by A, N, S, T, V, or R; and wherein amino acid residues at position 100 of SEQ ID NO:1 is A or is substituted by L, R, S, V, Y, C, G, T, K, or P.

In some embodiments, the antibody of the invention is a human antibody. In other embodiments, the antibody of the invention is a humanized antibody. In some embodiments, the antibody is monoclonal. In some embodiments, the antibody (or polypeptide) is isolated. In some embodiments, the antibody (or polypeptide) is substantially pure.

The heavy chain constant region of the antibodies may be from any types of constant region, such as IgG, IgM, IgD, IgA, and IgE; and any isotypes, such as IgG1, IgG2, IgG3, and IgG4.

In some embodiments, the antibody comprises a modified constant region as described herein.

In another aspect, the invention provides a polynucleotide (which may be isolated) comprising a polynucleotide encoding a fragment or a region of the antibody G1 or its variants shown in Table 6. In one embodiment, the fragment is a light chain of the antibody G1. In another embodiment, the fragment is a heavy chain of the antibody G1. In yet another embodiment, the fragment contains one or more variable regions from a light chain and/or a heavy chain of the antibody G1. In yet another embodiment, the fragment contains one or more (i.e., one, two, three, four, five, or six) complementarity determining regions (CDRs) from a light chain and/or a heavy chain of the antibody G1.

In another aspect, the invention is a polynucleotide (which may be isolated) comprising a polynucleotide that encodes for antibody G1 or its variants shown in Table 6. In some embodiments, the polynucleotide comprises either or both of the polynucleotides shown in SEQ ID NO:9 and SEQ ID NO:10.

In another aspect, the invention provides polynucleotides encoding any of the antibodies (including antibody fragments) or polypeptides described herein.

In another aspect, the invention provides vectors (including expression and cloning vectors) and host cells comprising any of the polynucleotide disclosed herein. In some embodiments, the vector is pDb.CGRP.hFcGI having ATCC No. PTA-6867. In other embodiments, the vector is pEb.CGRP.hKGI having ATCC No. PTA-6866.

In another aspect, the invention is a host cell comprising a polynucleotide encoding any of the antibodies described herein.

In another aspect, the invention is a complex of CGRP bound by any of the antibodies or polypeptides described herein. In some embodiments, the antibody is antibody G1 or its variants shown in Table 6.

In another aspect, the invention is a pharmaceutical composition comprising an effective amount of any of the polypeptides (including antibodies, such as an antibody comprising one or more CDRs of antibody G1) or polynucleotides described herein, and a pharmaceutically acceptable excipient.

In another aspect, the invention is a method of generating antibody G1 comprising culturing a host cell or progeny thereof under conditions that allow production of antibody G1, wherein the host cell comprises an expression vector that encodes for antibody G1; and, in some embodiments, purifying the antibody G1. In some embodiments, the expression vector comprises one or both of the polynucleotide sequences shown in SEQ ID NO:9 and SEQ ID NO:10.

In another aspect, the invention provides methods of generating any of the antibodies or polypeptides described herein by expressing one or more polynucleotides encoding the antibody (which may be separately expressed as a single light or heavy chain, or both a light and a heavy chain are expressed from one vector) or the polypeptide in a suitable cell, generally followed by recovering and/or isolating the antibody or polypeptides of interest.

The anti-CGRP antagonist antibody and polypeptides, and polynucleotides encoding the antibodies and polypeptides of the present invention may be used for treating, preventing, ameliorating, controlling, or reducing incidence of diseases associated with abnormal function of CGRP, such as headache (e.g., migraine, cluster headache, chronic headache, and tension headache) and other conditions that may be treated or prevented by antagonizing CGRP activity.

In another aspect, the invention provides kits and compositions comprising any one or more of the compositions described herein. These kits, generally in suitable packaging and provided with appropriate instructions, are useful for any of the methods described herein.

BRIEF DESCRIPTION OF THE DRAWINGS

FIG. 1 is a table showing binding affinities of 12 murine antibodies for different alanine substituted human α-CGRP fragments. Binding affinities were measured at 25° C. using Biacore by flowing Fabs across CGRPs on the chip. The boxed values represent the loss in affinity of alanine mutants relative to parental fragment, 25-37 (italic), except K35A, which was derived from a 19-37 parent. "$^a$" indicates affinities for 19-37 and 25-37 fragments are the mean average±standard deviation of two independent measurements on different sensor chips. "$^b$" indicates these interactions deviated from a simple bimolecular interaction model due to a biphasic offrate, so their affinities were determined using a conformational change model. Grey-scale key: white (1.0) indicates parental affinity; light grey (less than 0.5) indicates higher affinity than parent; dark grey (more than 2) indicates lower affinity than parent; and black indicates that no binding was detected.

FIG. 5 shows the amino acid sequence of the heavy chain variable region (SEQ ID NO:1) and light chain variable region (SEQ ID NO:2) of antibody G1. The Kabat CDRs are in bold text, and the Chothia CDRs are underlined. The amino acid residues for the heavy chain and light chain variable region are numbered sequentially.

DETAILED DESCRIPTION OF THE INVENTION

Figure 2A:
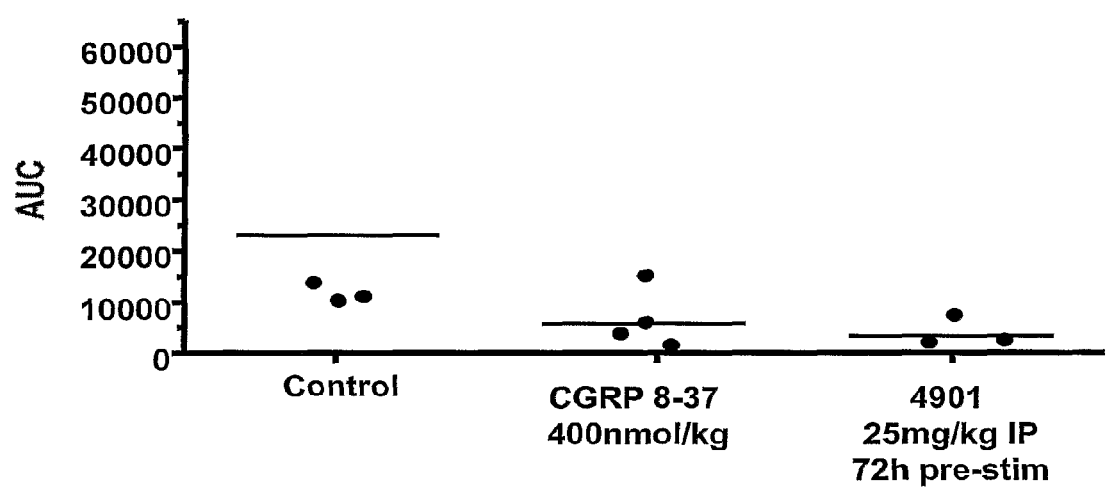
FIGS. 2A and 2B show the effect of administering CGRP 8-37 (400 nmol/kg), antibody 4901 (25 mg/kg), and antibody 7D11 (25 mg/kg) on skin blood flow measured as blood cell flux after electrical pulse stimulation for 30 seconds. CGRP 8-37 was administered intravenously (iv) 3-5 min before electrical pulse stimulation. Antibodies were administered intraperitoneal (IP) 72 hours before electrical pulse stimulation. Each point in the graphs represents AUC of one rat treated under the conditions as indicated. Each line in the graphs represents average AUC of rats treated under the condition as indicated. AUC (area under the curve) equals to Δflux×Δtime. "Δflux" represents the change of flux units after the electrical pulse stimulation; and "Δtime" represents the time period taken for the blood cell flux level to return to the level before the electrical pulse stimulation.

The invention disclosed herein provides methods for treating and/or preventing vasomotor symptoms such as headache (e.g., migraine, cluster headache, chronic headache, and tension headache) or hot flush in an individual by administering to the individual a therapeutically effective amount of an anti-CGRP antagonist antibody.

The invention disclosed herein also provides anti-CGRP antagonist antibodies and polypeptides derived from G1 or its variants shown in Table 6. The invention also provides methods of making and using these antibodies and polypeptides.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Definitions

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')$_2$, Fv), single chain (ScFv), mutants thereof, fusion proteins comprising an antibody portion (such as domain antibodies), and any other modified configuration of the immunoglobulin molecule that comprises an antigen recognition site. An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

As used herein, "monoclonal antibody" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, 1975, Nature, 256:495, or may be made by recombinant DNA methods such as described in U.S. Pat. No. 4,816,567. The monoclonal antibodies may also be isolated from phage libraries generated using the techniques described in McCafferty et al., 1990, Nature, 348:552-554, for example.

As used herein, "humanized" antibodies refer to forms of non-human (e.g. murine) antibodies that are specific chimeric immunoglobulins, immunoglobulin chains, or fragments thereof (such as Fv, Fab, Fab', F(ab')2 or other antigen-binding subsequences of antibodies) that contain minimal sequence derived from non-human immunoglobulin. For the most part, humanized antibodies are human immunoglobulins (recipient antibody) in which residues from a complementarity determining region (CDR) of the recipient are replaced by residues from a CDR of a non-human species (donor antibody) such as mouse, rat, or rabbit having the desired specificity, affinity, and, biological activity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, six) which are altered with respect to the original antibody, which are also termed one or more CDRs "derived from" one or more CDRs from the original antibody.

As used herein, "human antibody" means an antibody having an amino acid sequence corresponding to that of an antibody produced by a human and/or has been made using any of the techniques for making human antibodies known in the art or disclosed herein. This definition of a human antibody includes antibodies comprising at least one human heavy chain polypeptide or at least one human light chain polypeptide. One such example is an antibody comprising murine light chain and human heavy chain polypeptides. Human antibodies can be produced using various techniques known in the art. In one embodiment, the human antibody is selected from a phage library, where that phage library expresses human antibodies (Vaughan et al., 1996, Nature Biotechnology, 14:309-314; Sheets et al., 1998, PNAS, (USA) 95:6157-6162; Hoogenboom and Winter, 1991, J. Mol. Biol., 227:381; Marks et al., 1991, J. Mol. Biol., 222:581). Human antibodies can also be made by introducing human immunoglobulin loci into transgenic animals, e.g., mice in which the endogenous immunoglobulin genes have been partially or completely inactivated. This approach is described in U.S. Pat. Nos. 5,545,807; 5,545,806; 5,569,825; 5,625,126; 5,633,425; and 5,661,016. Alternatively, the human antibody may be prepared by immortalizing human B lymphocytes that produce an antibody directed against a target antigen (such B lymphocytes may be recovered from an individual or may have been immunized in vitro). See, e.g., Cole et al., Monoclonal Antibodies and Cancer Therapy, Alan R. Liss, p. 77 (1985); Boerner et al., 1991, J. Immunol., 147 (1):86-95; and U.S. Pat. No. 5,750,373.

As used herein, the term "calcitonin gene-related peptide" and "CGRP" refers to any form of calcitonin gene-related peptide and variants thereof that retain at least part of the activity of CGRP. For example, CGRP may be α-CGRP or β-CGRP. As used herein, CGRP includes all mammalian species of native sequence CGRP, e.g., human, canine, feline, equine, and bovine.

As used herein, an "anti-CGRP antagonist antibody" (interchangeably termed "anti-CGRP antibody") refers to an antibody that is able to bind to CGRP and inhibit CGRP biological activity and/or downstream pathway(s) mediated by CGRP signaling. An anti-CGRP antagonist antibody encompasses antibodies that block, antagonize, suppress or reduce (including significantly) CGRP biological activity, including downstream pathways mediated by CGRP signaling, such as receptor binding and/or elicitation of a cellular response to CGRP. For purpose of the present invention, it will be explicitly understood that the term "anti-CGRP antagonist antibody" encompasses all the previously identified terms, titles, and functional states and characteristics whereby the CGRP itself, an CGRP biological activity (including but not limited to its ability to mediate any aspect of headache), or the consequences of the biological activity, are substantially nullified, decreased, or neutralized in any meaningful degree. In some embodiment, an anti-CGRP antagonist antibody binds CGRP and prevents CGRP binding to a CGRP receptor. In other embodiments, an anti-CGRP antibody binds CGRP and prevents activation of a CGRP receptor. Examples of anti-CGRP antagonist antibodies are provided herein.

As used herein, the terms "G1" and "antibody G1" are used interchangeably to refer to an antibody produced by expression vectors having deposit numbers of ATCC PTA-6867 and ATCC PTA-6866. The amino acid sequence of the heavy chain and light chain variable regions are shown in FIG. 5. The CDR portions of antibody G1 (including Chothia and Kabat CDRs) are diagrammatically depicted in FIG. 5. The polynucleotides encoding the heavy and light chain variable regions are shown in SEQ ID NO:9 and SEQ ID NO:10. The characterization of G1 is described in the Examples.

The terms "polypeptide", "oligopeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon an antibody, the polypeptides can occur as single chains or associated chains.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al (1997) J. Molec. Biol. 273:927-948)). As used herein, a CDR may refer to CDRs defined by either approach or by a combination of both approaches.

A "constant region" of an antibody refers to the constant region of the antibody light chain or the constant region of the antibody heavy chain, either alone or in combination.

An epitope that "preferentially binds" or "specifically binds" (used interchangeably herein) to an antibody or a polypeptide is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a CGRP epitope is an antibody that binds this epitope with greater affinity, avidity, more readily, and/or with greater duration than it binds to other CGRP epitopes or non-CGRP epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

As used herein, "substantially pure" refers to material which is at least 50% pure (i.e., free from contaminants), more preferably at least 90% pure, more preferably at least 95% pure, more preferably at least 98% pure, more preferably at least 99% pure.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

The term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as in Kabat. Kabat et al., Sequences of Proteins of Imunological Interest, 5th Ed. Public Health Service, National Institutes of Health, Bethesda, Md., 1991. The Fc region of an immunoglobulin generally comprises two constant domains, CH2 and CH3.

As used herein, "Fc receptor" and "FcR" describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinet, 1991, Ann. Rev. Immunol., 9:457-92; Capel et al., 1994, Immunomethods, 4:25-34; and de Haas et al., 1995, J. Lab. Clin. Med., 126:330-41. "FcR" also includes the neonatal receptor, FcRn, which is responsible for the transfer of maternal IgGs to the fetus (Guyer et al., 1976, J. Immunol., 117:587; and Kim et al., 1994, J. Immunol., 24:249).

"Complement dependent cytotoxicity" and "CDC" refer to the lysing of a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., J. Immunol. Methods, 202:163 (1996), may be performed.

A "functional Fc region" possesses at least one effector function of a native sequence Fc region. Exemplary "effector functions" include C1q binding; complement dependent cytotoxicity (CDC); Fc receptor binding; antibody-dependent cell-mediated cytotoxicity (ADCC); phagocytosis; down-regulation of cell surface receptors (e.g. B cell receptor; BCR), etc. Such effector functions generally require the Fc region to be combined with a binding domain (e.g. an antibody variable domain) and can be assessed using various assays known in the art for evaluating such antibody effector functions.

A "native sequence Fc region" comprises an amino acid sequence identical to the amino acid sequence of an Fc region found in nature. A "variant Fc region" comprises an amino acid sequence which differs from that of a native sequence Fc region by virtue of at least one amino acid modification, yet retains at least one effector function of the native sequence Fc region. Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably at least about 90% sequence identity therewith, more preferably at least about 95%, at least about 96%, at least about 97%, at least about 98%, at least about 99% sequence identity therewith.

As used herein "antibody-dependent cell-mediated cytotoxicity" and "ADCC" refer to a cell-mediated reaction in which nonspecific cytotoxic cells that express Fc receptors (FcRs) (e.g. natural killer (NK) cells, neutrophils, and macrophages) recognize bound antibody on a target cell and subsequently cause lysis of the target cell. ADCC activity of a molecule of interest can be assessed using an in vitro ADCC assay, such as that described in U.S. Pat. No. 5,500,362 or 5,821,337. Useful effector cells for such assays include peripheral blood mononuclear cells (PBMC) and NK cells. Alternatively, or additionally, ADCC activity of the molecule of interest may be assessed in vivo, e.g., in a animal model such as that disclosed in Clynes et al., 1998, PNAS (USA), 95:652-656.

As used herein, "treatment" is an approach for obtaining beneficial or desired clinical results. For purposes of this invention, beneficial or desired clinical results include, but are not limited to, one or more of the following: improvement in any aspect of a headache including lessening severity, alleviation of pain intensity, and other associated symptoms, reducing frequency of recurrence, increasing the quality of life of those suffering from the headache, and decreasing dose of other medications required to treat the headache. For migraine, other associated symptoms include, but are not limited to, nausea, vomiting, and sensitivity to light, sound, and/or movement. For cluster headache, other associated symptoms include, but are not limited to swelling under or around the eyes, excessive tears, red eye, Rhinorrhea or nasal congestion, and red flushed face.

"Reducing incidence" of headache means any of reducing severity (which can include reducing need for and/or amount of (e.g., exposure to) other drugs and/or therapies generally used for this condition, including, for example, ergotamine, dihydroergotamine, or triptans for migraine), duration, and/or frequency (including, for example, delaying or increasing time to next episodic attack in an individual). As is understood by those skilled in the art, individuals may vary in terms of their response to treatment, and, as such, for example, a "method of reducing incidence of headache in an individual" reflects administering the anti-CGRP antagonist antibody based on a reasonable expectation that such administration may likely cause such a reduction in incidence in that particular individual.

"Ameliorating" headache or one or more symptoms of headache means a lessening or improvement of one or more symptoms of headache as compared to not administering an anti-CGRP antagonist antibody. "Ameliorating" also includes shortening or reduction in duration of a symptom.

As used herein, "controlling headache" refers to maintaining or reducing severity or duration of one or more symptoms of headache or frequency of headache attacks in an individual (as compared to the level before treatment). For example, the duration or severity of head pain, or frequency of attacks is reduced by at least about any of 10%, 20%, 30%, 40%, 50%, 60%, or 70% in the individual as compared to the level before treatment.

As used therein, "delaying" the development of headache means to defer, hinder, slow, retard, stabilize, and/or postpone progression of the disease. This delay can be of varying lengths of time, depending on the history of the disease and/or individuals being treated. As is evident to one skilled in the art, a sufficient or significant delay can, in effect, encompass prevention, in that the individual does not develop headache (e.g., migraine). A method that "delays" development of the symptom is a method that reduces probability of developing the symptom in a given time frame and/or reduces extent of the symptoms in a given time frame, when compared to not using the method. Such comparisons are typically based on clinical studies, using a statistically significant number of subjects.

"Development" or "progression" of headache means initial manifestations and/or ensuing progression of the disorder. Development of headache can be detectable and assessed using standard clinical techniques as well known in the art. However, development also refers to progression that may be undetectable. For purpose of this invention, development or progression refers to the biological course of the symptoms. "Development" includes occurrence, recurrence, and onset. As used herein "onset" or "occurrence" of headache includes initial onset and/or recurrence.

As used herein, an "effective dosage" or "effective amount" of drug, compound, or pharmaceutical composition is an amount sufficient to effect beneficial or desired results. For prophylactic use, beneficial or desired results include results such as eliminating or reducing the risk, lessening the severity, or delaying the outset of the disease, including biochemical, histological and/or behavioral symptoms of the disease, its complications and intermediate pathological phenotypes presenting during development of the disease. For therapeutic use, beneficial or desired results include clinical results such as reducing pain intensity, duration, or frequency of headache attack, and decreasing one or more symptoms resulting from headache (biochemical, histological and/or behavioral), including its complications and intermediate pathological phenotypes presenting during development of the disease, increasing the quality of life of those suffering from the disease, decreasing the dose of other medications required to treat the disease, enhancing effect of another medication, and/or delaying the progression of the disease of patients. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

An "individual" or a "subject" is a mammal, more preferably a human. Mammals also include, but are not limited to, farm animals, sport animals, pets, primates, horses, dogs, cats, mice and rats.

As used herein, "vector" means a construct, which is capable of delivering, and preferably expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, "pharmaceutically acceptable carrier" or "pharmaceutical acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline. Compositions comprising such carriers are formulated by well known conventional methods (see, for example, Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000).

The term "$k_{on}$", as used herein, is intended to refer to the rate constant for association of an antibody to an antigen.

The term "$k_{off}$", as used herein, is intended to refer to the rate constant for dissociation of an antibody from the antibody/antigen complex.

The term "$K_D$", as used herein, is intended to refer to the equilibrium dissociation constant of an antibody-antigen interaction.

As used herein, the term "vasomotor symptom," is intended to refer to conditions related to vasodilation and include, but are not limited to, headache (such as migraine, . . . others), hot flushing (or hot flashes), cold flashes, insomnia, sleep disturbances, mood disorders, irritability, excessive perspiration, night sweats, day sweats, fatigue, and the like, caused by, inter alia, thermoregulatory dysfunction.

As used herein, the terms "flushing", "hot flush" and "hot flash" are art-recognized terms that refer to an episodic disturbance in body temperature typically consisting of a sudden skin flushing, usually accompanied by perspiration in a subject.

A. Methods for Preventing or Treating Vasomotor Symptoms

In one aspect, the invention provides a method for treating or preventing at least one vasomotor symptom, such as headache (e.g., migraine) or hot flushes, in an individual comprising administering to the individual an effective amount of an anti-CGRP antagonist antibody or polypeptides derived from the antibody.

In another aspect, the invention provides a method for ameliorating, controlling, reducing incidence of, or delaying the development or progression of at least one vasomotor symptom, such as headache (e.g., migraine) or hot flushes, in an individual comprising administering to the individual an effective amount of an anti-CGRP antagonist antibody.

In another aspect, the invention provides methods for ameliorating, controlling, reducing incidence of, or delaying the development or progression of headache (e.g., migraine) in an individual comprising administering to the individual an effective amount of an anti-CGRP antagonist antibody in combination with at least one additional agent useful for treating headache.

Such additional agents include, but are not limited to, 5-HT agonists and NSAIDs. For example, the antibody and the at least one additional agent can be concomitantly administered, i.e., they can be given in close enough temporal proximity to allow their individual therapeutic effects to overlap. For example, the amount of 5-HT agonist or NSAID administered in combination with an anti-CGRP antibody should be sufficient to reduce the frequency of headache relapse in patients or produce longer lasting efficacy compared to the administration of either one of these agents in the absence of the other. This procedure may be used to treat headaches falling into any of a wide variety of classes including: migraine with or without aura; hemiplegic migraine; cluster headaches; migrainous neuralgia; chronic headaches; tension headaches; headaches resulting from other medical conditions (such as infection or increased pressure in the skull due to a tumor); chronic paroxysmal hemicrania; miscellaneous headache unassociated with a structural lesion; headache associated with a non-vascular intracranial disorder; headache associated with the administration of a substance or its withdrawal; headache associated with noncephalic infection; headache associated with a metabolic disorder; headache associated with a disorder of the cranium, neck, eyes, ears, nose, sinuses, teeth, mouth or other facial or cranial structure; cranial neuralgias; and nerve trunk pain and deafferentiation pain.

Those skilled in the art will be able to determine appropriate dosage amounts for particular agents to be used in combination with an anti-CGRP antibody. For example, sumatriptan may be administered in a dosage from about 0.01 to about 300 mg. When administered non-parenterally, the typical dosage of sumatriptan is from about 25 to about 100 mg with about 50 mg being generally preferred and, when administered parenterally, the preferred dosage is about 6 mg. However, these dosages may be varied according to methods standard in the art so that they are optimized for a particular patient or for a particular combination therapy. Further, for example, celecoxib may be administered in an amount of between 50 and 500 mg.

In another aspect, the invention provides methods for ameliorating, controlling, reducing incidence of, or delaying the development or progression of hot flushes in an individual comprising administering to the individual an effective amount of an anti-CGRP antagonist antibody in combination with at least one additional agent useful for treating hot flushes. Such additional agents include, but are not limited to, hormone-based treatments, including estrogens and/or some progestins.

With respect to all methods described herein, reference to anti-CGRP antagonist antibodies also include compositions comprising one or more of these agents. These compositions may further comprise suitable excipients, such as pharmaceutically acceptable excipients including buffers, which are well known in the art. The present invention can be used alone or in combination with other conventional methods of treatment.

The anti-CGRP antagonist antibody can be administered to an individual via any suitable route. It should be apparent to a person skilled in the art that the examples described herein are not intended to be limiting but to be illustrative of the techniques available. Accordingly, in some embodiments, the anti-CGRP antagonist antibody is administered to a individual in accord with known methods, such as intravenous administration, e.g., as a bolus or by continuous infusion over a period of time, by intramuscular, intraperitoneal, intracerebrospinal, subcutaneous, intra-articular, sublingually, intrasynovial, via insufflation, intrathecal, oral, inhalation or topical routes. Administration can be systemic, e.g., intravenous administration, or localized. Commercially available nebulizers for liquid formulations, including jet nebulizers and ultrasonic nebulizers are useful for administration. Liquid formulations can be directly nebulized and lyophilized powder can be nebulized after reconstitution. Alternatively, anti-CGRP antagonist antibody can be aerosolized using a fluorocarbon formulation and a metered dose inhaler, or inhaled as a lyophilized and milled powder.

In one embodiment, an anti-CGRP antagonist antibody is administered via site-specific or targeted local delivery techniques. Examples of site-specific or targeted local delivery techniques include various implantable depot sources of the anti-CGRP antagonist antibody or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568.

Various formulations of an anti-CGRP antagonist antibody may be used for administration. In some embodiments, the anti-CGRP antagonist antibody may be administered neat. In some embodiments, anti-CGRP antagonist antibody and a pharmaceutically acceptable excipient may be in various formulations. Pharmaceutically acceptable excipients are known in the art, and are relatively inert substances that facilitate administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonparenteral drug delivery are set forth in Remington, The Science and Practice of Pharmacy 20th Ed. Mack Publishing (2000).

In some embodiments, these agents are formulated for administration by injection (e.g., intraperitoneally, intravenously, subcutaneously, intramuscularly, etc.). Accordingly, these agents can be combined with pharmaceutically acceptable vehicles such as saline, Ringer's solution, dextrose solution, and the like. The particular dosage regimen, i.e., dose, timing and repetition, will depend on the particular individual and that individual's medical history.

An anti-CGRP antibody can be administered using any suitable method, including by injection (e.g., intraperitoneally, intravenously, subcutaneously, intramuscularly, etc.). Anti-CGRP antibodies can also be administered via inhalation, as described herein. Generally, for administration of anti-CGRP antibodies, an initial candidate dosage can be about 2 mg/kg. For the purpose of the present invention, a typical daily dosage might range from about any of 3 μg/kg to 30 μg/kg to 300 μg/kg to 3 mg/kg, to 30 mg/kg to 100 mg/kg or more, depending on the factors mentioned above. For example, dosage of about 1 mg/kg, about 2.5 mg/kg, about 5 mg/kg, about 10 mg/kg, and about 25 mg/kg may be used. For repeated administrations over several days or longer, depending on the condition, the treatment is sustained until a desired suppression of symptoms occurs or until sufficient therapeutic levels are achieved, for example, to reduce pain. An exemplary dosing regimen comprises administering an initial dose of about 2 mg/kg, followed by a weekly maintenance dose of about 1 mg/kg of the anti-CGRP antibody, or followed by a maintenance dose of about 1 mg/kg every other week. However, other dosage regimens may be useful, depending on the pattern of pharmacokinetic decay that the practitioner wishes to achieve. For example, in some embodiments, dosing from one-four times a week is contemplated. The progress of this therapy is easily monitored by conventional techniques and assays. The dosing regimen (including the CGRP antagonist(s) used) can vary over time.

For the purpose of the present invention, the appropriate dosage of an anti-CGRP antagonist antibody will depend on the anti-CGRP antagonist antibody (or compositions thereof) employed, the type and severity of headache (e.g., migraine) to be treated, whether the agent is administered for preventive or therapeutic purposes, previous therapy, the patient's clinical history and response to the agent, and the discretion of the attending physician. Typically the clinician will administer an anti-CGRP antagonist antibody, until a dosage is reached that achieves the desired result. Dose and/or frequency can vary over course of treatment.

Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of headache (e.g., migraine). Alternatively, sustained continuous release formulations of anti-CGRP antagonist antibodies may be appropriate. Various formulations and devices for achieving sustained release are known in the art.

In one embodiment, dosages for an anti-CGRP antagonist antibody may be determined empirically in individuals who have been given one or more administration(s) of an anti-CGRP antagonist antibody. Individuals are given incremental dosages of an anti-CGRP antagonist antibody. To assess efficacy of an anti-CGRP antagonist antibody, an indicator of the disease can be followed.

Administration of an anti-CGRP antagonist antibody in accordance with the method in the present invention can be continuous or intermittent, depending, for example, upon the recipient's physiological condition, whether the purpose of the administration is therapeutic or prophylactic, and other factors known to skilled practitioners. The administration of an anti-CGRP antagonist antibody may be essentially continuous over a preselected period of time or may be in a series of spaced dose, e.g., either before, during, or after developing headache (e.g., migraine); before; during; before and after; during and after; before and during; or before, during, and after developing headache. Administration can be before, during and/or after any event likely to give rise to headache.

In some embodiments, more than one anti-CGRP antagonist antibody may be present. At least one, at least two, at least three, at least four, at least five different, or more anti-CGRP antagonist antibody can be present. Generally, those anti-CGRP antagonist antibodies may have complementary activities that do not adversely affect each other. An antagonist anti-CGRP antibody can also be used in conjunction with other CGRP antagonists or CGRP receptor antagonists. For example, one or more of the following CGRP antagonists may be used: an anti-sense molecule directed to an CGRP (including an anti-sense molecule directed to a nucleic acid encoding CGRP), an CGRP inhibitory compound, an CGRP structural analog, a dominant-negative mutation of a CGRP receptor that binds an CGRP, and an anti-CGRP receptor antibody. An anti-CGRP antagonist antibody can also be used in conjunction with other agents that serve to enhance and/or complement the effectiveness of the agents.

Therapeutic formulations of the anti-CGRP antagonist antibody used in accordance with the present invention are prepared for storage by mixing an antibody having the desired degree of purity with optional pharmaceutically acceptable carriers, excipients or stabilizers (Remington, The Science and Practice of Pharmacy 20th Ed. Mack Publishing (2000)), in the form of lyophilized formulations or aqueous solutions. Acceptable carriers, excipients, or stabilizers are nontoxic to recipients at the dosages and concentrations employed, and may comprise buffers such as phosphate, citrate, and other organic acids; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosacchandes, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Liposomes containing the anti-CGRP antagonist antibody are prepared by methods known in the art, such as described in Epstein, et al., Proc. Natl. Acad. Sci. USA 82:3688 (1985); Hwang, et al., Proc. Natl Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington, The Science and Practice of Pharmacy 20th Ed. Mack Publishing (2000).

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or 'poly(v nylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The formulations to be used for in vivo administration must be sterile. This is readily accomplished by, for example, filtration through sterile filtration membranes. Therapeutic anti-CGRP antagonist antibody compositions are generally placed into a container having a sterile access port, for example, an intravenous solution bag or vial having a stopper pierceable by a hypodermic injection needle.

The compositions according to the present invention may be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example gylcerol or glucose, to adjust the tonicity of the emulsion. Suitable emulsions will typically contain up to 20% oil, for example, between 5 and 20%. The fat emulsion can comprise fat droplets between 0.1 and 1.0 lm, particularly 0.1 and 0.5 lm, and have a pH in the range of 5.5 to 8.0.

The emulsion compositions can be those prepared by mixing an anti-CGRP antagonist antibody with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect. Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Diagnosis or assessment of headache is well-established in the art. Assessment may be performed based on subjective measures, such as patient characterization of symptoms. For example, migraine may be diagnosed based on the following criteria: 1) episodic attacks of headache lasting 4 to 72 hours; 2) with two of the following symptoms: unilateral pain, throbbing, aggravation on movement, and pain of moderate or severe intensity; and 3) one of the following symptoms: nausea or vomiting, and photophobia or phonophobia. Goadsby et al., N. Engl. J. Med. 346:257-270, 2002.

Treatment efficacy can be assessed by methods well-known in the art. For example, pain relief may be assessed. Accordingly, in some embodiments, pain relief is subjectively observed after 1, 2, or a few hours after administering an anti-CGRP antibody. In some embodiments, frequency of headache attacks is subjectively observed after administering an anti-CGRP antibody.

B. Anti-CGRP Antagonist Antibodies

The methods of the invention use an anti-CGRP antagonist antibody, which refers to any antibody molecule that blocks, suppresses or reduces (including significantly) CGRP biological activity, including downstream pathways mediated by CGRP signaling, such as receptor binding and/or elicitation of a cellular response to CGRP.

An anti-CGRP antagonist antibody should exhibit any one or more of the following characteristics: (a) bind to CGRP; (b) block CGRP from binding to its receptor(s); (c) block or decrease CGRP receptor activation (including cAMP activation); (d) inhibit CGRP biological activity or downstream pathways mediated by CGRP signaling function; (e) prevent, ameliorate, or treat any aspect of headache (e.g., migraine); (f) increase clearance of CGRP; and (g) inhibit (reduce) CGRP synthesis, production or release. Anti-CGRP antagonist antibodies are known in the art. See, e.g., Tan et al., Clin. Sci. (Lond). 89:565-73, 1995; Sigma (Missouri, US), product number C7113 (clone #4901); Plourde et al., Peptides 14:1225-1229, 1993.

For purposes of this invention, the antibody reacts with CGRP in a manner that inhibits CGRP and/or downstream pathways mediated by the CGRP signaling function. In some embodiments, the anti-CGRP antagonist antibody recognizes human CGRP. In some embodiments, the anti-CGRP antagonist antibody binds to both human α-CGRP and β-CGRP. In some embodiments, the anti-CGRP antagonist antibody binds human and rat CGRP. In some embodiments, the anti-CGRP antagonist antibody binds the C-terminal fragment having amino acids 25-37 of CGRP. In some embodiments, the anti-CGRP antagonist antibody binds a C-terminal epitope within amino acids 25-37 of CGRP.

The antibodies useful in the present invention can encompass monoclonal antibodies, polyclonal antibodies, antibody fragments (e.g., Fab, Fab', F(ab')2, Fv, Fc, etc.), chimeric antibodies, bispecific antibodies, heteroconjugate antibodies, single chain (ScFv), mutants thereof, fusion proteins comprising an antibody portion (e.g., a domain antibody), humanized antibodies, and any other modified configuration of the immunoglobulin molecule that comprises an antigen recognition site of the required specificity, including glycosylation variants of antibodies, amino acid sequence variants of antibodies, and covalently modified antibodies. The antibodies may be murine, rat, human, or any other origin (including chimeric or humanized antibodies).

In some embodiments, the anti-CGRP antagonist antibody is a monoclonal antibody. In some embodiments, the anti-CGRP antagonist antibody is humanized. In some embodiments, the antibody is human. In some embodiments, the anti-CGRP antagonist antibody is antibody G1 (as described herein). In some embodiments, the anti-CGRP antagonist antibody comprises one or more CDR(s) (such as one, two, three, four, five, or, in some embodiments, all six CDRs) of antibody G1 or variants of G1 shown in Table 6. In still other embodiments, the anti-CGRP antagonist antibody comprises the amino acid sequence of the heavy chain variable region shown in FIG. 5 (SEQ ID NO:1) and the amino acid sequence of the light chain variable region shown in FIG. 5 (SEQ ID NO:2).

In some embodiments, the antibody comprises a modified constant region, such as a constant region that is immunologically inert described herein. In some embodiments, the constant region is modified as described in Eur. J. Immunol. (1999) 29:2613-2624; PCT Application No. PCT/GB99/01441; and/or UK Patent Application No. 9809951.8. In other embodiments, the antibody comprises a human heavy chain IgG2 constant region comprising the following mutations: A330P331 to S330S331 (amino acid numbering with reference to the wildtype IgG2 sequence). Eur. J. Immunol. (1999) 29:2613-2624. In some embodiments, the antibody comprises a constant region of IgG4 comprising the following mutations: E233F234L235 to P233V234A235. In still other embodiments, the constant region is aglycosylated for N-linked glycosylation. In some embodiments, the constant region is aglycosylated for N-linked glycosylation by mutating the oligosaccharide attachment residue (such as Asn297) and/or flanking residues that are part of the N-glycosylation recognition sequence in the constant region. In some embodiments, the constant region is aglycosylated for N-linked glycosylation. The constant region may be aglycosylated for N-linked glycosylation enzymatically or by expression in a glycosylation deficient host cell.

The binding affinity ($K_D$) of an anti-CGRP antagonist antibody to CGRP (such as human α-CGRP) can be about 0.02 to about 200 nM. In some embodiments, the binding affinity is any of about 200 nM, about 100 nM, about 50 nM, about 10 nM, about 1 nM, about 500 pM, about 100 pM, about 60 pM, about 50 pM, about 20 pM, about 15 pM, about 10 pM, about 5 pM, or about 2 pM. In some embodiments, the binding affinity is less than any of about 250 nM, about 200 nM, about 100 nM, about 50 nM, about 10 nM, about 1 nM, about 500 pM, about 100 pM, or about 50 pM.

One way of determining binding affinity of antibodies to CGRP is by measuring binding affinity of monofunctional Fab fragments of the antibody. To obtain monofunctional Fab fragments, an antibody (for example, IgG) can be cleaved with papain or expressed recombinantly. The affinity of an anti-CGRP Fab fragment of an antibody can be determined by surface plasmon resonance (Biacore3000™ surface plasmon resonance (SPR) system, Biacore, INC, Piscataway N.J.) equipped with pre-immobilized streptavidin sensor chips (SA) using HBS-EP running buffer (0.01M HEPES, pH 7.4, 0.15 NaCl, 3 mM EDTA, 0.005% v/v Surfactant P20). Biotinylated human CGRP (or any other CGRP) can be diluted into HBS-EP buffer to a concentration of less than 0.5 ug/mL and injected across the individual chip channels using variable contact times, to achieve two ranges of antigen density, either 50-200 response units (RU) for detailed kinetic studies or 800-1,000 RU for screening assays. Regeneration studies have shown that 25 mM NaOH in 25% v/v ethanol effectively removes the bound Fab while keeping the activity of CGRP on the chip for over 200 injections. Typically, serial dilutions (spanning concentrations of 0.1-10× estimated $K_D$ of purified Fab samples are injected for 1 min at 100 µL/minute and dissociation times of up to 2 hours are allowed. The concentrations of the Fab proteins are determined by ELISA and/or SDS-PAGE electrophoresis using a Fab of known concentration (as determined by amino acid analysis) as a standard. Kinetic association rates ($k_{on}$) and dissociation rates ($k_{off}$) are obtained simultaneously by fitting the data globally to a 1:1 Langmuir binding model (Karlsson, R. Roos, H. Fagerstam, L. Petersson, B. (1994). Methods Enzymology 6. 99-110) using the BIAevaluation program. Equilibrium dissociation constant ($K_D$) values are calculated as $k_{off}/k_{on}$. This protocol is suitable for use in determining binding affinity of an antibody to any CGRP, including human CGRP, CGRP of another mammalian (such as mouse CGRP, rat CGRP, primate CGRP), as well as different forms of CGRP (such as α and β form). Binding affinity of an antibody is generally measured at 25° C., but can also be measured at 37° C.

The anti-CGRP antagonist antibodies may be made by any method known in the art. The route and schedule of immunization of the host animal are generally in keeping with established and conventional techniques for antibody stimulation and production, as further described herein. General techniques for production of human and mouse antibodies are known in the art and are described herein.

It is contemplated that any mammalian subject including humans or antibody producing cells therefrom can be manipulated to serve as the basis for production of mammalian, including human, hybridoma cell lines. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C. (1975) Nature 256:495-497 or as modified by Buck, D. W., et al., In Vitro, 18:377-381 (1982). Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the anti-CGRP monoclonal antibodies of the subject invention. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as source of antibodies encompass all derivatives, progeny cells of the parent hybridomas that produce monoclonal antibodies specific for CGRP, or a portion thereof.

Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity if present, can be removed, for example, by running the preparation over adsorbents made of the immunogen attached to a solid phase and eluting or releasing the desired antibodies off the immunogen. Immunization of a host animal with a human CGRP, or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glutaradehyde, succinic anhydride, SOCl2, or R1N=C=NR, where R and R1 are different alkyl groups, can yield a population of antibodies (e.g., monoclonal antibodies).

If desired, the anti-CGRP antagonist antibody (monoclonal or polyclonal) of interest may be sequenced and the polynucleotide sequence may then be cloned into a vector for expression or propagation. The sequence encoding the antibody of interest may be maintained in vector in a host cell and the host cell can then be expanded and frozen for future use. In an alternative, the polynucleotide sequence may be used for genetic manipulation to "humanize" the antibody or to improve the affinity, or other characteristics of the antibody. For example, the constant region may be engineered to more resemble human constant regions to avoid immune response if the antibody is used in clinical trials and treatments in humans. It may be desirable to genetically manipulate the antibody sequence to obtain greater affinity to CGRP and greater efficacy in inhibiting CGRP. It will be apparent to one of skill in the art that one or more polynucleotide changes can be made to the anti-CGRP antagonist antibody and still maintain its binding ability to CGRP.

There are four general steps to humanize a monoclonal antibody. These are: (1) determining the nucleotide and predicted amino acid sequence of the starting antibody light and heavy variable domains (2) designing the humanized antibody, i.e., deciding which antibody framework region to use during the humanizing process (3) the actual humanizing methodologies/techniques and (4) the transfection and expression of the humanized antibody. See, for example, U.S. Pat. Nos. 4,816,567; 5,807,715; 5,866,692; 6,331,415; 5,530,101; 5,693,761; 5,693,762; 5,585,089; and 6,180,370.

A number of "humanized" antibody molecules comprising an antigen-binding site derived from a non-human immunoglobulin have been described, including chimeric antibodies having rodent or modified rodent V regions and their associated complementarity determining regions (CDRs) fused to human constant domains. See, for example, Winter et al. Nature 349:293-299 (1991), Lobuglio et al. Proc. Nat. Acad. Sci. USA 86:4220-4224 (1989), Shaw et al. J Immunol. 138:4534-4538 (1987), and Brown et al. Cancer Res. 47:3577-3583 (1987). Other references describe rodent CDRs grafted into a human supporting framework region (FR) prior to fusion with an appropriate human antibody constant domain. See, for example, Riechmann et al. Nature 332:323-327 (1988), Verhoeyen et al. Science 239:1534-1536 (1988), and Jones et al. Nature 321:522-525 (1986). Another reference describes rodent CDRs supported by recombinantly veneered rodent framework regions. See, for example, European Patent Publication No. 0519596. These "humanized" molecules are designed to minimize unwanted immunological response toward rodent anti-human antibody molecules which limits the duration and effectiveness of therapeutic applications of those moieties in human recipients. For example, the antibody constant region can be engineered such that it is immunologically inert (e.g., does not trigger complement lysis). See, e.g. PCT Publication No. PCT/GB99/01441; UK Patent Application No. 9809951.8. Other methods of humanizing antibodies that may also be utilized are disclosed by Daugherty et al., Nucl. Acids Res. 19:2471-2476 (1991) and in U.S. Pat. Nos. 6,180,377; 6,054,297; 5,997,867; 5,866,692; 6,210,671; and 6,350,861; and in PCT Publication No. WO 01/27160.

In yet another alternative, fully human antibodies may be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse™ from Abgenix, Inc. (Fremont, Calif.) and HuMAb-Mouse® and TC Mouse™ from Medarex, Inc. (Princeton, N.J.).

In an alternative, antibodies may be made recombinantly and expressed using any method known in the art. In another alternative, antibodies may be made recombinantly by phage display technology. See, for example, U.S. Pat. Nos. 5,565,332; 5,580,717; 5,733,743; and 6,265,150; and Winter et al., Annu. Rev. Immunol. 12:433-455 (1994). Alternatively, the phage display technology (McCafferty et al., Nature 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for review see, e.g., Johnson, Kevin S. and Chiswell, David J., Current Opinion in Structural Biology 3:564-571 (1993). Several sources of V-gene segments can be used for phage display. Clackson et al., Nature 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Mark et al., J. Mol. Biol. 222:581-597 (1991), or Griffith et al., EMBO J. 12:725-734 (1993). In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling." Marks, et al., Bio/Technol. 10:779-783 (1992)). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the pM-nM range. A strategy for making very large phage antibody repertoires (also known as "the mother-of-all libraries") has been described by Waterhouse et al., Nucl. Acids Res. 21:2265-2266 (1993). Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable regions capable of restoring a functional antigen-binding site, i.e., the epitope governs (imprints) the choice of partner. When the process is repeated in order to replace the remaining rodent V domain, a human antibody is obtained (see PCT Publication No. WO 93/06213, published Apr. 1, 1993). Unlike traditional humanization of rodent antibodies by CDR grafting, this technique provides completely human antibodies, which have no framework or CDR residues of rodent origin.

It is apparent that although the above discussion pertains to humanized antibodies, the general principles discussed are applicable to customizing antibodies for use, for example, in dogs, cats, primate, equines and bovines. It is further apparent that one or more aspects of humanizing an antibody described herein may be combined, e.g., CDR grafting, framework mutation and CDR mutation.

Antibodies may be made recombinantly by first isolating the antibodies and antibody producing cells from host animals, obtaining the gene sequence, and using the gene sequence to express the antibody recombinantly in host cells (e.g., CHO cells). Another method which may be employed is to express the antibody sequence in plants (e.g., tobacco) or transgenic milk. Methods for expressing antibodies recombinantly in plants or milk have been disclosed. See, for example, Peeters, et al. Vaccine 19:2756 (2001); Lonberg, N. and D. Huszar Int. Rev. Immunol 13:65 (1995); and Pollock, et al., J Immunol Methods 231:147(1999). Methods for making derivatives of antibodies, e.g., humanized, single chain, etc. are known in the art.

Immunoassays and flow cytometry sorting techniques such as fluorescence activated cell sorting (FACS) can also be employed to isolate antibodies that are specific for CGRP.

The antibodies can be bound to many different carriers. Carriers can be active and/or inert. Examples of well-known carriers include polypropylene, polystyrene, polyethylene, dextran, nylon, amylases, glass, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation. In some embodiments, the carrier comprises a moiety that targets the myocardium.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors (such as expression vectors disclosed in PCT Publication No. WO 87/04462), which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publication No. WO 87/04462. The DNA also may be modified, for example, by substituting the coding sequence for human heavy and light chain constant domains in place of the homologous murine sequences, Morrison et al., Proc. Nat. Acad. Sci. 81:6851 (1984), or by covalently joining to the immunoglobulin coding sequence all or part of the coding sequence for a non-immunoglobulin polypeptide. In that manner, "chimeric" or "hybrid" antibodies are prepared that have the binding specificity of an anti-CGRP monoclonal antibody herein.

Anti-CGRP antagonist antibodies and polypeptides derived from antibodies can be identified or characterized using methods known in the art, whereby reduction, amelioration, or neutralization of an CGRP biological activity is detected and/or measured. For example, anti-CGRP antagonist antibody can also be identified by incubating a candidate agent with CGRP and monitoring any one or more of the following characteristics: (a) bind to CGRP; (b) block CGRP from binding to its receptor(s); (c) block or decrease CGRP receptor activation (including cAMP activation); (d) inhibit CGRP biological activity or downstream pathways mediated by CGRP signaling function; (e) prevent, ameliorate, or treat any aspect of headache (e.g., migraine); (f) increase clearance of CGRP; and (g) inhibit (reduce) CGRP synthesis, production or release. In some embodiments, an anti-CGRP antagonist antibody or polypeptide is identified by incubating a candidate agent with CGRP and monitoring binding and/or attendant reduction or neutralization of a biological activity of CGRP. The binding assay may be performed with purified CGRP polypeptide(s), or with cells naturally expressing, or transfected to express, CGRP polypeptide(s). In one embodiment, the binding assay is a competitive binding assay, where the ability of a candidate antibody to compete with a known anti-CGRP antagonist for CGRP binding is evaluated. The assay may be performed in various formats, including the ELISA format. In other embodiments, an anti-CGRP antagonist antibody is identified by incubating a candidate agent with CGRP and monitoring binding and attendant inhibition of CGRP receptor activation expressed on the surface of a cell.

Following initial identification, the activity of a candidate anti-CGRP antagonist antibody can be further confirmed and refined by bioassays, known to test the targeted biological activities. Alternatively, bioassays can be used to screen candidates directly. For example, CGRP promotes a number of measurable changes in responsive cells. These include, but are not limited to, stimulation of cAMP in the cell (e.g., SK-N-MC cells). Antagonist activity may also be measured using animal models, such as measuring skin vasodilatation induced by stimulation of the rat saphenous nerve. Escott et al., Br. J. Pharmacol. 110: 772-776, 1993. Animal models of headaches (such as, migraine) may further be used for testing efficacy of antagonist antibodies or polypeptides. Reuter, et al., Functional Neurology (15) Suppl. 3, 2000. Some of the methods for identifying and characterizing anti-CGRP antagonist antibody or polypeptide are described in detail in the Examples.

Anti-CGRP antagonist antibodies may be characterized using methods well known in the art. For example, one method is to identify the epitope to which it binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which an anti-CGRP antagonist antibody binds. Epitope mapping is commercially available from various sources, for example, Pepscan Systems (Edelhertweg 15, 8219 PH Lelystad, The Netherlands). The epitope can be a linear epitope, i.e., contained in a single stretch of amino acids, or a conformational epitope formed by a three-dimensional interaction of amino acids that may not necessarily be contained in a single stretch. Peptides of varying lengths (e.g., at least 4-6 amino acids long) can be isolated or synthesized (e.g., recombinantly) and used for binding assays with an anti-CGRP antagonist antibody. In another example, the epitope to which the anti-CGRP antagonist antibody binds can be determined in a systematic screening by using overlapping peptides derived from the CGRP sequence and determining binding by the anti-CGRP antagonist antibody. According to the gene fragment expression assays, the open reading frame encoding CGRP is fragmented either randomly or by specific genetic constructions and the reactivity of the expressed fragments of CGRP with the antibody to be tested is determined. The gene fragments may, for example, be produced by PCR and then transcribed and translated into protein in vitro, in the presence of radioactive amino acids. The binding of the antibody to the radioactively labeled CGRP fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. In an additional example, mutagenesis of an antigen binding domain, domain swapping experiments and alanine scanning mutagenesis can be performed to identify residues required, sufficient, and/or necessary for epitope binding. For example, domain swapping experiments can be performed using a mutant CGRP in which various fragments of the CGRP polypeptide have been replaced (swapped) with sequences from a closely related, but antigenically distinct protein (such as another member of the neurotrophin protein family). By assessing binding of the antibody to the mutant CGRP, the importance of the particular CGRP fragment to antibody binding can be assessed.

Yet another method which can be used to characterize an anti-CGRP antagonist antibody is to use competition assays with other antibodies known to bind to the same antigen, i.e., various fragments on CGRP, to determine if the anti-CGRP antagonist antibody binds to the same epitope as other antibodies. Competition assays are well known to those of skill in the art.

An expression vector can be used to direct expression of an anti-CGRP antagonist antibody. One skilled in the art is familiar with administration of expression vectors to obtain expression of an exogenous protein in vivo. See, e.g., U.S. Pat. Nos. 6,436,908; 6,413,942; and 6,376,471. Administration of expression vectors includes local or systemic administration, including injection, oral administration, particle gun or catheterized administration, and topical administration. In another embodiment, the expression vector is administered directly to the sympathetic trunk or ganglion, or into a coronary artery, atrium, ventrical, or pericardium.

Targeted delivery of therapeutic compositions containing an expression vector, or subgenomic polynucleotides can also be used. Receptor-mediated DNA delivery techniques are described in, for example, Findeis et al., Trends Biotechnol. (1993) 11:202; Chiou et al., Gene Therapeutics: Methods And Applications Of Direct Gene Transfer (J. A. Wolff, ed.) (1994); Wu et al., J. Biol. Chem. (1988) 263:621; Wu et al., J. Biol. Chem. (1994) 269:542; Zenke et al., Proc. Natl. Acad. Sci. USA (1990) 87:3655; Wu et al., J. Biol. Chem. (1991) 266:338. Therapeutic compositions containing a polynucleotide are administered in a range of about 100 ng to about 200 mg of DNA for local administration in a gene therapy protocol. Concentration ranges of about 500 ng to about 50 mg, about 1 µg to about 2 mg, about 5 µg to about 500 µg, and about 20 µg to about 100 µg of DNA can also be used during a gene therapy protocol. The therapeutic polynucleotides and polypeptides can be delivered using gene delivery vehicles. The gene delivery vehicle can be of viral or non-viral origin (see generally, Jolly, Cancer Gene Therapy (1994) 1:51; Kimura, Human Gene Therapy (1994) 5:845; Connelly, Human Gene Therapy (1995) 1:185; and Kaplitt, Nature Genetics (1994) 6:148). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther. (1992) 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther. (1992) 3:147); ligand-linked DNA (see, e.g., Wu, J. Biol. Chem. (1989) 264:16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP 0524968. Additional approaches are described in Philip, Mol. Cell Biol. (1994) 14:2411, and in Woffendin, Proc. Natl. Acad. Sci. (1994) 91:1581.

C. Antibody G1 and Related Antibodies, Polypeptides, Polynucleotides, Vectors and Host Cells This invention encompasses compositions, including pharmaceutical compositions, comprising antibody G1 and its variants shown in Table 6 or polypeptide derived from antibody G1 and its variants shown in Table 6; and polynucleotides comprising sequences encoding G1 and its variants or the polypeptide. As used herein, compositions comprise one or more antibodies or polypeptides (which may or may not be an antibody) that bind to CGRP, and/or one or more polynucleotides comprising sequences encoding one or more antibodies or polypeptides that bind to CGRP. These compositions may further comprise suitable excipients, such as pharmaceutically acceptable excipients including buffers, which are well known in the art.

The anti-CGRP antagonist antibodies and polypeptides of the invention are characterized by any (one or more) of the following characteristics: (a) bind to CGRP; (b) block CGRP from binding to its receptor(s); (c) block or decrease CGRP receptor activation (including cAMP activation); (d) inhibit CGRP biological activity or downstream pathways mediated by CGRP signaling function; (e) prevent, ameliorate, or treat any aspect of headache (e.g., migraine); (0 increase clearance of CGRP; and (g) inhibit (reduce) CGRP synthesis, production or release.

Accordingly, the invention provides any of the following, or compositions (including pharmaceutical compositions) comprising any of the following: (a) antibody G1 or its variants shown in Table 6; (b) a fragment or a region of antibody G1 or its variants shown in Table 6; (c) a light chain of antibody G1 or its variants shown in Table 6; (d) a heavy chain of antibody G1 or its variants shown in Table 6; (e) one or more variable region(s) from a light chain and/or a heavy chain of antibody G1 or its variants shown in Table 6; (f) one or more CDR(s) (one, two, three, four, five or six CDRs) of antibody G1 or its variants shown in Table 6; (g) CDR H3 from the heavy chain of antibody G1; (h) CDR L3 from the light chain of antibody G1 or its variants shown in Table 6; (i) three CDRs from the light chain of antibody G1 or its variants shown in Table 6; (j) three CDRs from the heavy chain of antibody G1 or its variants shown in Table 6; (k) three CDRs from the light chain and three CDRs from the heavy chain, of antibody G1 or its variants shown in Table 6; and (l) an antibody comprising any one of (b) through (k). The invention also provides polypeptides comprising any one or more of the above.

The CDR portions of antibody G1 (including Chothia and Kabat CDRs) are diagrammatically depicted in FIG. 5. Determination of CDR regions is well within the skill of the art. It is understood that in some embodiments, CDRs can be a combination of the Kabat and Chothia CDR (also termed "combined CDRs" or "extended CDRs"). In some embodiments, the CDRs are the Kabat CDRs. In other embodiments, the CDRs are the Chothia CDRs. In other words, in embodiments with more than one CDR, the CDRs may be any of Kabat, Chothia, combination CDRs, or combinations thereof.

In some embodiments, the invention provides a polypeptide (which may or may not be an antibody) which comprises at least one CDR, at least two, at least three, or at least four, at least five, or all six CDRs that are substantially identical to at least one CDR, at least two, at least three, at least four, at least five or all six CDRs of G1 or its variants shown in Table 6. Other embodiments include antibodies which have at least two, three, four, five, or six CDR(s) that are substantially identical to at least two, three, four, five or six CDRs of G1 or derived from G1. In some embodiments, the at least one, two, three, four, five, or six CDR(s) are at least about 85%, 86%, 87%, 88%, 89%, 90%, 95%, 96%, 97%, 98%, or 99% identical to at least one, two, three, four, five or six CDRs of G1 or its variants shown in Table 6. It is understood that, for purposes of this invention, binding specificity and/or overall activity is generally retained, although the extent of activity may vary compared to G1 or its variants shown in Table 6 (may be greater or lesser).

The invention also provides a polypeptide (which may or may not be an antibody) which comprises an amino acid sequence of G1 or its variants shown in Table 6 that has any of the following: at least 5 contiguous amino acids, at least 8 contiguous amino acids, at least about 10 contiguous amino acids, at least about 15 contiguous amino acids, at least about 20 contiguous amino acids, at least about 25 contiguous amino acids, at least about 30 contiguous amino acids of a sequence of G1 or its variants shown in Table 6, wherein at least 3 of the amino acids are from a variable region of G1 (FIG. 5) or its variants shown in Table 6. In one embodiment, the variable region is from a light chain of G1. In another embodiment, the variable region is from a heavy chain of G1. An exemplary polypeptide has contiguous amino acid (lengths described above) from both the heavy and light chain variable regions of G1. In another embodiment, the 5 (or more) contiguous amino acids are from a complementarity determining region (CDR) of G1 shown in FIG. 5. In some embodiments, the contiguous amino acids are from a variable region of G1.

The binding affinity ($K_D$) of an anti-CGRP antagonist antibody and polypeptide to CGRP (such as human α-CGRP) can be about 0.06 to about 200 nM. In some embodiments, the binding affinity is any of about 200 nM, 100 nM, about 50 nM, about 10 nM, about 1 nM, about 500 pM, about 100 pM, about 60 pM, about 50 pM, about 20 pM, about 15 pM, about 10 pM, about 5 pM, or about 2 pM. In some embodiments, the binding affinity is less than any of about 250 nM, about 200 nM, about 100 nM, about 50 nM, about 10 nM, about 1 nM, about 500 pM, about 100 pM, or about 50 pM.

The invention also provides methods of making any of these antibodies or polypeptides. The antibodies of this invention can be made by procedures known in the art. The polypeptides can be produced by proteolytic or other degradation of the antibodies, by recombinant methods (i.e., single or fusion polypeptides) as described above or by chemical synthesis. Polypeptides of the antibodies, especially shorter polypeptides up to about 50 amino acids, are conveniently made by chemical synthesis. Methods of chemical synthesis are known in the art and are commercially available. For example, an antibody could be produced by an automated polypeptide synthesizer employing the solid phase method. See also, U.S. Pat. Nos. 5,807,715; 4,816,567; and 6,331,415.

In another alternative, the antibodies can be made recombinantly using procedures that are well known in the art. In one embodiment, a polynucleotide comprises a sequence encoding the heavy chain and/or the light chain variable regions of antibody G1 shown in SEQ ID NO:9 and SEQ ID NO:10. In another embodiment, the polynucleotide comprising the nucleotide sequence shown in SEQ ID NO:9 and SEQ ID NO:10 are cloned into one or more vectors for expression or propagation. The sequence encoding the antibody of interest may be maintained in a vector in a host cell and the host cell can then be expanded and frozen for future use. Vectors (including expression vectors) and host cells are further described herein.

The invention also encompasses single chain variable region fragments ("scFv") of antibodies of this invention, such as G1. Single chain variable region fragments are made by linking light and/or heavy chain variable regions by using a short linking peptide. Bird et al. (1988) Science 242:423-426. An example of a linking peptide is (GGGGS)3 (SEQ ID NO: 57) which bridges approximately 3.5 nm between the carboxy terminus of one variable region and the amino terminus of the other variable region. Linkers of other sequences have been designed and used. Bird et al. (1988). Linkers can in turn be modified for additional functions, such as attachment of drugs or attachment to solid supports. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as *E. coli*. Polynucleotides encoding the scFv of interest can be made by routine manipulations such as ligation of polynucleotides. The resultant scFv can be isolated using standard protein purification techniques known in the art.

Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad Sci. USA 90:6444-6448; Poljak, R. J., et al. (1994) Structure 2:1121-1123).

For example, bispecific antibodies, monoclonal antibodies that have binding specificities for at least two different antigens, can be prepared using the antibodies disclosed herein. Methods for making bispecific antibodies are known in the art (see, e.g., Suresh et al., 1986, Methods in Enzymology 121:210). Traditionally, the recombinant production of bispecific antibodies was based on the coexpression of two immunoglobulin heavy chain-light chain pairs, with the two heavy chains having different specificities (Millstein and Cuello, 1983, Nature 305, 537-539).

According to one approach to making bispecific antibodies, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2 and CH3 regions. It is preferred to have the first heavy chain constant region (CH1), containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one approach, the bispecific antibodies are composed of a hybrid immunoglobulin heavy chain with a first binding specificity in one arm, and a hybrid immunoglobulin heavy chain-light chain pair (providing a second binding specificity) in the other arm. This asymmetric structure, with an immunoglobulin light chain in only one half of the bispecific molecule, facilitates the separation of the desired bispecific compound from unwanted immunoglobulin chain combinations. This approach is described in PCT Publication No. WO 94/04690, published Mar. 3, 1994.

Heteroconjugate antibodies, comprising two covalently joined antibodies, are also within the scope of the invention. Such antibodies have been used to target immune system cells to unwanted cells (U.S. Pat. No. 4,676,980), and for treatment of HIV infection (PCT application publication Nos. WO 91/00360 and WO 92/200373; EP 03089). Heteroconjugate antibodies may be made using any convenient cross-linking methods. Suitable cross-linking agents and techniques are well known in the art, and are described in U.S. Pat. No. 4,676,980.

Chimeric or hybrid antibodies also may be prepared in vitro using known methods of synthetic protein chemistry, including those involving cross-linking agents. For example, immunotoxins may be constructed using a disulfide exchange reaction or by forming a thioether bond. Examples of suitable reagents for this purpose include iminothiolate and methyl-4-mercaptobutyrimidate.

Humanized antibody comprising one or more CDRs of antibody G1 or its variants shown in Table 6, or one or more CDRs derived from antibody G1 or its variants shown in Table 6 can be made using any methods known in the art. For example, four general steps may be used to humanize a monoclonal antibody.

The invention encompasses modifications to antibody G1 or its variants shown in Table 6, including functionally equivalent antibodies which do not significantly affect their properties and variants which have enhanced or decreased activity and/or affinity. For example, the amino acid sequence of antibody G1 or its variants shown in Table 6 may be mutated to obtain an antibody with the desired binding affinity to CGRP. Modification of polypeptides is routine practice in the art and need not be described in detail herein. Modification of polypeptides is exemplified in the Examples. Examples of modified polypeptides include polypeptides with conservative substitutions of amino acid residues, one or more deletions or additions of amino acids which do not significantly deleteriously change the functional activity, or use of chemical analogs.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide which increases the serum half-life of the antibody.

Substitution variants have at least one amino acid residue in the antibody molecule removed and a different residue inserted in its place. The sites of greatest interest for substitutional mutagenesis include the hypervariable regions, but FR alterations are also contemplated. Conservative substitutions are shown in Table 1 under the heading of "conservative substitutions". If such substitutions result in a change in biological activity, then more substantial changes, denominated "exemplary substitutions" in Table 1, or as further described below in reference to amino acid classes, may be introduced and the products screened.

TABLE 1

Amino Acid Substitutions

| Original Residue | Conservative Substitutions | Exemplary Substitutions |
| --- | --- | --- |
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |

TABLE 1-continued

Amino Acid Substitutions

| Original Residue | Conservative Substitutions | Exemplary Substitutions |
|---|---|---|
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) Non-polar: Norleucine, Met, Ala, Val, Leu, Ile;
(2) Polar without charge: Cys, Ser, Thr, Asn, Gln;
(3) Acidic (negatively charged): Asp, Glu;
(4) Basic (positively charged): Lys, Arg;
(5) Residues that influence chain orientation: Gly, Pro; and
(6) Aromatic: Trp, Tyr, Phe, His.

Non-conservative substitutions are made by exchanging a member of one of these classes for another class.

Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

Amino acid modifications can range from changing or modifying one or more amino acids to complete redesign of a region, such as the variable region. Changes in the variable region can alter binding affinity and/or specificity. In some embodiments, no more than one to five conservative amino acid substitutions are made within a CDR domain. In other embodiments, no more than one to three conservative amino acid substitutions are made within a CDR domain. In still other embodiments, the CDR domain is CDR H3 and/or CDR L3.

Modifications also include glycosylated and nonglycosylated polypeptides, as well as polypeptides with other post-translational modifications, such as, for example, glycosylation with different sugars, acetylation, and phosphorylation. Antibodies are glycosylated at conserved positions in their constant regions (Jefferis and Lund, 1997, Chem. Immunol. 65:111-128; Wright and Morrison, 1997, TibTECH 15:26-32). The oligosaccharide side chains of the immunoglobulins affect the protein's function (Boyd et al., 1996, Mol. Immunol. 32:1311-1318; Wittwe and Howard, 1990, Biochem. 29:4175-4180) and the intramolecular interaction between portions of the glycoprotein, which can affect the conformation and presented three-dimensional surface of the glycoprotein (Hefferis and Lund, supra; Wyss and Wagner, 1996, Current Opin. Biotech. 7:409-416). Oligosaccharides may also serve to target a given glycoprotein to certain molecules based upon specific recognition structures. Glycosylation of antibodies has also been reported to affect antibody-dependent cellular cytotoxicity (ADCC). In particular, CHO cells with tetracycline-regulated expression of β(1,4)-N-acetylglucosaminyltransferase III (GnTIII), a glycosyltransferase catalyzing formation of bisecting GlcNAc, was reported to have improved ADCC activity (Umana et al., 1999, Mature Biotech. 17:176-180).

Glycosylation of antibodies is typically either N-linked or O-linked. N-linked refers to the attachment of the carbohydrate moiety to the side chain of an asparagine residue. The tripeptide sequences asparagine-X-serine, asparagine-X-threonine, and asparagine-X-cysteine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

The glycosylation pattern of antibodies may also be altered without altering the underlying nucleotide sequence. Glycosylation largely depends on the host cell used to express the antibody. Since the cell type used for expression of recombinant glycoproteins, e.g. antibodies, as potential therapeutics is rarely the native cell, variations in the glycosylation pattern of the antibodies can be expected (see, e.g. Hse et al., 1997, J. Biol. Chem. 272:9062-9070).

In addition to the choice of host cells, factors that affect glycosylation during recombinant production of antibodies include growth mode, media formulation, culture density, oxygenation, pH, purification schemes and the like. Various methods have been proposed to alter the glycosylation pattern achieved in a particular host organism including introducing or overexpressing certain enzymes involved in oligosaccharide production (U.S. Pat. Nos. 5,047,335; 5,510,261 and 5,278,299). Glycosylation, or certain types of glycosylation, can be enzymatically removed from the glycoprotein, for example using endoglycosidase H (Endo H), N-glycosidase F, endoglycosidase F1, endoglycosidase F2, endoglycosidase F3. In addition, the recombinant host cell can be genetically engineered to be defective in processing certain types of polysaccharides. These and similar techniques are well known in the art.

Other methods of modification include using coupling techniques known in the art, including, but not limited to, enzymatic means, oxidative substitution and chelation. Modifications can be used, for example, for attachment of labels for immunoassay. Modified G1 polypeptides are made using established procedures in the art and can be screened using standard assays known in the art, some of which are described below and in the Examples.

In some embodiments of the invention, the antibody comprises a modified constant region, such as a constant region that is immunologically inert or partially inert, e.g., does not trigger complement mediated lysis, does not stimulate antibody-dependent cell mediated cytotoxicity (ADCC), or does not activate microglia; or have reduced activities (compared to the unmodified antibody) in any one or more of the following: triggering complement mediated lysis, stimulating antibody-dependent cell mediated cytotoxicity (ADCC), or activating microglia. Different modifications of the constant region may be used to achieve optimal level and/or combination of effector functions. See, for example, Morgan et al., Immunology 86:319-324 (1995); Lund et al., J. Immunology 157:4963-9 157:4963-4969 (1996); Idusogie et al., J. Immunology 164:4178-4184 (2000); Tao et al., J. Immunology 143: 2595-2601 (1989); and Jefferis et al., Immunological Reviews 163:59-76 (1998). In some embodiments, the constant region is modified as described in Eur. J. Immunol. (1999) 29:2613-2624; PCT Application No. PCT/GB99/01441; and/or UK Patent Application No. 9809951.8. In other embodiments, the antibody comprises a human heavy chain IgG2 constant region comprising the following mutations: A330P331 to S330S331 (amino acid numbering with reference to the wildtype IgG2 sequence). Eur. J. Immunol. (1999) 29:2613-2624. In still other embodiments, the constant region is aglycosylated for N-linked glycosylation. In some embodiments, the constant region is aglycosylated for N-linked glycosylation by mutating the glycosylated amino acid residue or flanking residues that are part of the N-glycosylation recognition sequence in the constant region. For example, N-glycosylation site N297 may be mutated to A, Q, K, or H. See, Tao et al., J. Immunology 143: 2595-2601 (1989); and Jefferis et al., Immunological Reviews 163:59-76 (1998). In some embodiments, the constant region is aglycosylated for N-linked glycosylation. The constant region may be aglycosylated for N-linked glycosylation enzymatically (such as removing carbohydrate by enzyme PNGase), or by expression in a glycosylation deficient host cell.

Other antibody modifications include antibodies that have been modified as described in PCT Publication No. WO 99/58572, published Nov. 18, 1999. These antibodies comprise, in addition to a binding domain directed at the target molecule, an effector domain having an amino acid sequence substantially homologous to all or part of a constant domain of a human immunoglobulin heavy chain. These antibodies are capable of binding the target molecule without triggering significant complement dependent lysis, or cell-mediated destruction of the target. In some embodiments, the effector domain is capable of specifically binding FcRn and/or FcγRIIb. These are typically based on chimeric domains derived from two or more human immunoglobulin heavy chain $C_H2$ domains. Antibodies modified in this manner are particularly suitable for use in chronic antibody therapy, to avoid inflammatory and other adverse reactions to conventional antibody therapy.

The invention includes affinity matured embodiments. For example, affinity matured antibodies can be produced by procedures known in the art (Marks et al., 1992, Bio/Technology, 10:779-783; Barbas et al., 1994, Proc Nat. Acad. Sci, USA 91:3809-3813; Schier et al., 1995, Gene, 169:147-155; Yelton et al., 1995, J. Immunol., 155:1994-2004; Jackson et al., 1995, J. Immunol., 154(7):3310-9; Hawkins et al, 1992, J. Mol. Biol., 226:889-896; and WO2004/058184).

The following methods may be used for adjusting the affinity of an antibody and for characterizing a CDR. One way of characterizing a CDR of an antibody and/or altering (such as improving) the binding affinity of a polypeptide, such as an antibody, termed "library scanning mutagenesis". Generally, library scanning mutagenesis works as follows. One or more amino acid positions in the CDR are replaced with two or more (such as 3, 4, 5, 6, 7, 8, 9, 10, 11, 12, 13, 14, 15, 16, 17, 18, 19, or 20) amino acids using art recognized methods. This generates small libraries of clones (in some embodiments, one for every amino acid position that is analyzed), each with a complexity of two or more members (if two or more amino acids are substituted at every position). Generally, the library also includes a clone comprising the native (unsubstituted) amino acid. A small number of clones, e.g., about 20-80 clones (depending on the complexity of the library), from each library are screened for binding affinity to the target polypeptide (or other binding target), and candidates with increased, the same, decreased or no binding are identified. Methods for determining binding affinity are well-known in the art. Binding affinity may be determined using Biacore surface plasmon resonance analysis, which detects differences in binding affinity of about 2-fold or greater. Biacore is particularly useful when the starting antibody already binds with a relatively high affinity, for example a $K_D$ of about 10 nM or lower. Screening using Biacore surface plasmon resonance is described in the Examples, herein.

Binding affinity may be determined using Kinexa Biocensor, scintillation proximity assays, ELISA, ORIGEN immunoassay (IGEN), fluorescence quenching, fluorescence transfer, and/or yeast display. Binding affinity may also be screened using a suitable bioassay.

In some embodiments, every amino acid position in a CDR is replaced (in some embodiments, one at a time) with all 20 natural amino acids using art recognized mutagenesis methods (some of which are described herein). This generates small libraries of clones (in some embodiments, one for every amino acid position that is analyzed), each with a complexity of 20 members (if all 20 amino acids are substituted at every position).

In some embodiments, the library to be screened comprises substitutions in two or more positions, which may be in the same CDR or in two or more CDRs. Thus, the library may comprise substitutions in two or more positions in one CDR. The library may comprise substitution in two or more positions in two or more CDRs. The library may comprise substitution in 3, 4, 5, or more positions, said positions found in two, three, four, five or six CDRs. The substitution may be prepared using low redundancy codons. See, e.g., Table 2 of Balint et al., (1993) Gene 137(1):109-18).

The CDR may be CDRH3 and/or CDRL3. The CDR may be one or more of CDRL1, CDRL2, CDRL3, CDRH1, CDRH2, and/or CDRH3. The CDR may be a Kabat CDR, a Chothia CDR, or an extended CDR.

Candidates with improved binding may be sequenced, thereby identifying a CDR substitution mutant which results in improved affinity (also termed an "improved" substitution). Candidates that bind may also be sequenced, thereby identifying a CDR substitution which retains binding.

Multiple rounds of screening may be conducted. For example, candidates (each comprising an amino acid substitution at one or more position of one or more CDR) with improved binding are also useful for the design of a second library containing at least the original and substituted amino acid at each improved CDR position (i.e., amino acid position in the CDR at which a substitution mutant showed improved binding). Preparation, and screening or selection of this library is discussed further below.

Library scanning mutagenesis also provides a means for characterizing a CDR, in so far as the frequency of clones with improved binding, the same binding, decreased binding or no binding also provide information relating to the importance of each amino acid position for the stability of the antibody-antigen complex. For example, if a position of the CDR retains binding when changed to all 20 amino acids, that position is identified as a position that is unlikely to be required for antigen binding. Conversely, if a position of CDR retains binding in only a small percentage of substitutions, that position is identified as a position that is important to CDR function. Thus, the library scanning mutagenesis methods generate information regarding positions in the CDRs that can be changed to many different amino acids (including all 20 amino acids), and positions in the CDRs which cannot be changed or which can only be changed to a few amino acids.

Candidates with improved affinity may be combined in a second library, which includes the improved amino acid, the original amino acid at that position, and may further include additional substitutions at that position, depending on the complexity of the library that is desired, or permitted using the desired screening or selection method. In addition, if desired, adjacent amino acid position can be randomized to at least two or more amino acids. Randomization of adjacent amino acids may permit additional conformational flexibility in the mutant CDR, which may in turn, permit or facilitate the introduction of a larger number of improving mutations. The library may also comprise substitution at positions that did not show improved affinity in the first round of screening.

The second library is screened or selected for library members with improved and/or altered binding affinity using any method known in the art, including screening using Biacore surface plasmon resonance analysis, and selection using any method known in the art for selection, including phage display, yeast display, and ribosome display.

The invention also encompasses fusion proteins comprising one or more fragments or regions from the antibodies (such as G1) or polypeptides of this invention. In one embodiment, a fusion polypeptide is provided that comprises at least 10 contiguous amino acids of the variable light chain region shown in SEQ ID NO:2 (FIG. 5) and/or at least 10 amino acids of the variable heavy chain region shown in SEQ ID NO:1 (FIG. 5). In other embodiments, a fusion polypeptide is provided that comprises at least about 10, at least about 15, at least about 20, at least about 25, or at least about 30 contiguous amino acids of the variable light chain region shown in SEQ ID NO:2 (FIG. 5) and/or at least about 10, at least about 15, at least about 20, at least about 25, or at least about 30 contiguous amino acids of the variable heavy chain region shown in SEQ ID NO:1 (FIG. 5). In another embodiment, the fusion polypeptide comprises a light chain variable region and/or a heavy chain variable region of G1, as shown in SEQ ID NO:2 and SEQ ID NO:1 of FIG. 5. In another embodiment, the fusion polypeptide comprises one or more CDR(s) of G1. In still other embodiments, the fusion polypeptide comprises CDR H3 and/or CDR L3 of antibody G1. For purposes of this invention, an G1 fusion protein contains one or more G1 antibodies and another amino acid sequence to which it is not attached in the native molecule, for example, a heterologous sequence or a homologous sequence from another region. Exemplary heterologous sequences include, but are not limited to a "tag" such as a FLAG tag or a 6His tag (SEQ ID NO: 56). Tags are well known in the art.

A G1 fusion polypeptide can be created by methods known in the art, for example, synthetically or recombinantly. Typically, the G1 fusion proteins of this invention are made by preparing an expressing a polynucleotide encoding them using recombinant methods described herein, although they may also be prepared by other means known in the art, including, for example, chemical synthesis.

This invention also provides compositions comprising antibodies or polypeptides derived from G1 conjugated (for example, linked) to an agent that facilitate coupling to a solid support (such as biotin or avidin). For simplicity, reference will be made generally to G1 or antibodies with the understanding that these methods apply to any of the CGRP binding embodiments described herein. Conjugation generally refers to linking these components as described herein. The linking (which is generally fixing these components in proximate association at least for administration) can be achieved in any number of ways. For example, a direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

An antibody or polypeptide of this invention may be linked to a labeling agent (alternatively termed "label") such as a fluorescent molecule, a radioactive molecule or any others labels known in the art. Labels are known in the art which generally provide (either directly or indirectly) a signal.

The invention also provides compositions (including pharmaceutical compositions) and kits comprising antibody G1, and, as this disclosure makes clear, any or all of the antibodies and/or polypeptides described herein.

The invention also provides isolated polynucleotides encoding the antibodies and polypeptides of the invention (including an antibody comprising the polypeptide sequences of the light chain and heavy chain variable regions shown in FIG. 5), and vectors and host cells comprising the polynucleotide.

Accordingly, the invention provides polynucleotides (or compositions, including pharmaceutical compositions), comprising polynucleotides encoding any of the following: (a) antibody G1 or its variants shown in Table 6; (b) a fragment or a region of antibody G1 or its variants shown in Table 6; (c) a light chain of antibody G1 or its variants shown in Table 6; (d) a heavy chain of antibody G1 or its variants shown in Table 6; (e) one or more variable region(s) from a light chain and/or a heavy chain of antibody G1 or its variants shown in Table 6; (0 one or more CDR(s) (one, two, three, four, five or six CDRs) of antibody G1 or its variants shown in Table 6; (g) CDR H3 from the heavy chain of antibody G1; (h) CDR L3 from the light chain of antibody G1 or its variants shown in Table 6; (i) three CDRs from the light chain of antibody G1 or its variants shown in Table 6; (j) three CDRs from the heavy chain of antibody G1 or its variants shown in Table 6; (k) three CDRs from the light chain and three CDRs from the heavy chain, of antibody G1 or its variants shown in Table 6; and (l) an antibody comprising any one of (b) through (k). In some embodiments, the polynucleotide comprises either or both of the polynucleotide(s) shown in SEQ ID NO: 9 and SEQ ID NO: 10.

In another aspect, the invention provides polynucleotides encoding any of the antibodies (including antibody fragments) and polypeptides described herein, such as antibodies and polypeptides having impaired effector function. Polynucleotides can be made by procedures known in the art.

In another aspect, the invention provides compositions (such as a pharmaceutical compositions) comprising any of the polynucleotides of the invention. In some embodiments, the composition comprises an expression vector comprising a polynucleotide encoding the G1 antibody as described herein. In other embodiment, the composition comprises an expression vector comprising a polynucleotide encoding any of the antibodies or polypeptides described herein. In still other embodiments, the composition comprises either or both of the polynucleotides shown in SEQ ID NO:9 and SEQ ID NO:10. Expression vectors, and administration of polynucleotide compositions are further described herein.

In another aspect, the invention provides a method of making any of the polynucleotides described herein.

Polynucleotides complementary to any such sequences are also encompassed by the present invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes an antibody or a portion thereof) or may comprise a variant of such a sequence. Polynucleotide variants contain one or more substitutions, additions, deletions and/or insertions such that the immunoreactivity of the encoded polypeptide is not diminished, relative to a native immunoreactive molecule. The effect on the immunoreactivity of the encoded polypeptide may generally be assessed as described herein. Variants preferably exhibit at least about 70% identity, more preferably at least about 80% identity and most preferably at least about 90% identity to a polynucleotide sequence that encodes a native antibody or a portion thereof.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J., 1990, Unified Approach to Alignment and Phylogenes pp. 626-645 Methods in Enzymology vol. 183, Academic Press, Inc., San Diego, Calif.; Higgins, D. G. and Sharp, P. M., 1989, CABIOS 5:151-153; Myers, E. W. and Muller W., 1988, CABIOS 4:11-17; Robinson, E. D., 1971, Comb. Theor. 11:105; Santou, N., Nes, M., 1987, Mol. Biol. Evol. 4:406-425; Sneath, P. H. A. and Sokal, R. R., 1973, Numerical Taxonomy the Principles and Practice of Numerical Taxonomy, Freeman Press, San Francisco, Calif.; Wilbur, W. J. and Lipman, D. J., 1983, Proc. Natl. Acad. Sci. USA 80:726-730.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e. gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native antibody (or a complementary sequence).

Suitable "moderately stringent conditions" include prewashing in a solution of 5×SSC, 0.5% SDS, 1.0 mM EDTA (pH 8.0); hybridizing at 50° C.–65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

The polynucleotides of this invention can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al. (1989).

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al. eds., Birkauswer Press, Boston (1994).

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., (1989), for example.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Stratagene, and Invitrogen.

Expression vectors generally are replicable polynucleotide constructs that contain a polynucleotide according to the invention. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

The invention also provides host cells comprising any of the polynucleotides described herein. Any host cells capable of over-expressing heterologous DNAs can be used for the purpose of isolating the genes encoding the antibody, polypeptide or protein of interest. Non-limiting examples of mammalian host cells include but not limited to COS, HeLa, and CHO cells. See also PCT Publication No. WO 87/04462. Suitable non-mammalian host cells include prokaryotes (such as *E. coli* or *B. subtilis*) and yeast (such as *S. cerevisae, S. pombe*; or *K. lactis*). Preferably, the host cells express the cDNAs at a level of about 5 fold higher, more preferably 10 fold higher, even more preferably 20 fold higher than that of the corresponding endogenous antibody or protein of interest, if present, in the host cells. Screening the host cells for a specific binding to A□1-40 is effected by an immunoassay or FACS. A cell overexpressing the antibody or protein of interest can be identified.

D. Compositions

The compositions used in the methods of the invention comprise an effective amount of an anti-CGRP antagonist antibody or an anti-CGRP antagonist antibody derived polypeptide described herein. Examples of such compositions, as well as how to formulate, are also described in an earlier section and below. In one embodiment, the composition further comprises a CGRP antagonist. In another embodiment, the composition comprises one or more anti-CGRP antagonist antibodies. In other embodiments, the anti-CGRP antagonist antibody recognizes human CGRP. In still other embodiments, the anti-CGRP antagonist antibody is humanized. In still other embodiment, the anti-CGRP antagonist antibody comprises a constant region that does not trigger an unwanted or undesirable immune response, such as antibody-mediated lysis or ADCC. In other embodiments, the anti-CGRP antagonist antibody comprises one or more CDR(s) of antibody G1 (such as one, two, three, four, five, or, in some embodiments, all six CDRs from G1). In some embodiments, the anti-CGRP antagonist antibody is human.

It is understood that the compositions can comprise more than one anti-CGRP antagonist antibody (e.g., a mixture of anti-CGRP antagonist antibodies that recognize different epitopes of CGRP). Other exemplary compositions comprise more than one anti-CGRP antagonist antibodies that recognize the same epitope(s), or different species of anti-CGRP antagonist antibodies that bind to different epitopes of CGRP.

The composition used in the present invention can further comprise pharmaceutically acceptable carriers, excipients, or stabilizers (Remington: The Science and practice of Pharmacy 20th Ed. (2000) Lippincott Williams and Wilkins, Ed. K. E. Hoover.), in the form of lyophilized formulations or aqueous solutions. Acceptable carriers, excipients, or stabilizers are nontoxic to recipients at the dosages and concentrations, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Pharmaceutically acceptable excipients are further described herein.

The anti-CGRP antagonist antibody and compositions thereof can also be used in conjunction with other agents that serve to enhance and/or complement the effectiveness of the agents.

E. Kits

The invention also provides kits for use in the instant methods. Kits of the invention include one or more containers comprising an anti-CGRP antagonist antibody (such as a humanized antibody) or polypeptide described herein and instructions for use in accordance with any of the methods of the invention described herein. Generally, these instructions comprise a description of administration of the anti-CGRP antagonist antibody to treat, ameliorate or prevent headache (such as migraine) according to any of the methods described herein. The kit may further comprise a description of selecting an individual suitable for treatment based on identifying whether that individual has headache or whether the individual is at risk of having headache. In still other embodiments, the instructions comprise a description of administering an anti-CGRP antagonist antibody to an individual at risk of having headache (such as migraine).

In some embodiments, the antibody is a humanized antibody. In some embodiments, the antibody is human. In other embodiments, the antibody is a monoclonal antibody. In still other embodiments. In some embodiment, the antibody comprises one or more CDR(s) of antibody G1 (such as one, two, three, four, five, or, in some embodiments, all six CDRs from G1).

The instructions relating to the use of an anti-CGRP antagonist antibody generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, ameliorating and/or preventing headache (such as migraine). Instructions may be provided for practicing any of the methods described herein.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an anti-CGRP antagonist antibody. The container may further comprise a second pharmaceutically active agent.

Kits may optionally provide additional components such as buffers and interpretive information. Normally, the kit comprises a container and a label or package insert(s) on or associated with the container.

The following Examples are provided to illustrate but not limit the invention.

EXAMPLES

Example 1: Generation and Characterization of Monoclonal Antibodies Directed Against CGRP Generation of anti-CGRP antibodies. To generate anti-CGRP antibodies that have cross-species reactivity for rat and human CGRP, mice were immunized with 25-100 µg of human α-CGRP or β-CGRP conjugated to KLH in adjuvant (50 µl per footpad, 100 µl total per mouse) at various intervals. Immunization was generally performed as described in Geerligs H J et al., 1989, J. Immunol. Methods 124:95-102; Kenney J S et al., 1989, J. Immunol. Methods 121:157-166; and Wicher K et al., 1989, Int. Arch. Allergy Appl. Immunol. 89:128-135. Mice were first immunized with 50 µg of human α-CGRP or β-CGRP conjugated to KLH in CFA (complete Freund's adjuvant). After 21 days, mice were secondly immunized with 25 µg of human β-CGRP (for mice first immunized with human α-CGRP) or α-CGRP (for mice first immunized with human β-CGRP) conjugated to KLH in IFA (incomplete Freund's adjuvant). Twenty three days later after the second immunization, third immunization was performed with 25 µg of rat α-CGRP conjugated to KLH in IFA. Ten days later, antibody titers were tested using ELISA. Forth immunization was performed with 25 µg of the peptide (rat α-CGRP-KLH) in IFA 34 days after the third immunization. Final booster was performed with 100 µg soluble peptide (rat α-CGRP) 32 days after the forth immunization.

Splenocytes were obtained from the immunized mouse and fused with NSO myeloma cells at a ratio of 10:1, with polyethylene glycol 1500. The hybrids were plated out into 96-well plates in DMEM containing 20% horse serum and 2-oxaloacetate/pyruvate/insulin (Sigma), and hypoxanthine/aminopterin/thymidine selection was begun. On day 8, 100 µl of DMEM containing 20% horse serum was added to all the wells. Supernatants of the hybrids were screened by using antibody capture immunoassay. Determination of antibody class was done with class-specific second antibodies.

A panel of monoclonal antibody-producing cell lines was selected based on their binding to human and rat CGRP for further characterization. These antibodies and characteristics are shown below in Tables 2 and 3.

Purification and Fab fragment preparation. Monoclonal antibodies selected for further characterization were purified from supernatants of hybridoma cultures using protein A affinity chromatography. The supernatants were equilibrated to pH 8. The supernatants were then loaded to the protein A column MabSelect (Amersham Biosciences #17-5199-02) equilibrated with PBS to pH 8. The column was washed with 5 column volumes of PBS, pH 8. The antibodies were eluted with 50 mM citrate-phosphate buffer, pH 3. The eluted antibodies were neutralized with 1M Phosphate Buffer, pH 8. The purified antibodies were dialyzed with PBS, pH 7.4. The antibody concentrations were determined by SDS-PAGE, using a murine monoclonal antibody standard curve.

Fabs were prepared by papain proteolysis of the full antibodies using Immunopure Fab kit (Pierce #44885) and purified by flow through protein A chromatography following manufacturer instructions. Concentrations were determined by ELISA and/or SDS-PAGE electrophoresis using a standard Fab of known concentration (determined by amino acid analysis), and by A280 using 1OD=0.6 mg/ml (or theoretical equivalent based on the amino acid sequence).

Affinity determination of the Fabs. Affinities of the anti-CGRP monoclonal antibodies were determined at either 25° C. or 37° C. using the Biacore3000™ surface plasmon resonance (SPR) system (Biacore, INC, Piscataway N.J.) with the manufacture's own running buffer, HBS-EP (10 mM HEPES pH 7.4, 150 mM NaCl, 3 mM EDTA, 0.005% v/v polysorbate P20). Affinity was determined by capturing N-terminally biotinylated CGRP peptides (custom ordered from GenScript Corporation, New Jersey or Global Peptide Services, Colorado) via pre-immobilized streptavidin on SA chip and measuring binding kinetics of antibody Fab titrated across the CGRP surface. Biotinylated CGRP was diluted into HBS-EP and injected over the chip at a concentration of less than 0.001 mg/ml. Using variable flow time across the individual chip channels, two ranges of antigen density were achieved: <50 response units (RU) for detailed kinetic studies and about 800 RU for concentration studies and screening. Two- or three-fold serial dilutions typically at concentrations spanning 1-0.1 nM (aimed at 0.1-10× estimated $K_D$) of purified Fab fragments were injected for 1 minute at 100 μL/min and dissociation times of 10 minutes were allowed. After each binding cycle, surfaces were regenerated with 25 mM NaOH in 25% v/v ethanol, which was tolerated over hundreds of cycles. Kinetic association rate ($k_{on}$) and dissociation rate ($k_{off}$) were obtained simultaneously by fitting the data to a 1:1 Langmuir binding model (Karlsson, R. Roos, H. Fagerstam, L. Petersson, B. (1994). Methods Enzymology 6. 99-110) using the BIAevaluation program. Global equilibrium dissociation constants ($K_D$) or "affinities" were calculated from the ratio $K_D=k_{off}/k_{on}$. Affinities of the murine Fab fragments are shown in Tables 2 and 3.

Epitope mapping of the murine anti-CGRP antibodies. To determine the epitope that anti-CGRP antibodies bind on human α-CGRP, binding affinities of the Fab fragments to various CGRP fragments were measured as described above by capturing N-terminally biotinylated CGRP fragments amino acids 19-37 and amino acids 25-37 on a SA sensor chip. FIG. 1 shows their binding affinities measured at 25° C. As shown in FIG. 1, all antibodies, except antibody 4901, bind to human α-CGRP fragments 19-37 and 25-37 with affinity similar to their binding affinity to full length human α-CGRP (1-37). Antibody 4901 binds to human α-CGRP fragment 25-37 with six fold lower affinity than binding to full length human α-CGRP fragment, due mainly to a loss in off-rate. The data indicate that these anti-CGRP antibodies generally bind to the C-terminal end of CGRP.

Alanine scanning was performed to further characterize amino acids in human α-CGRP involved in binding of anti-CGRP antibodies. Different variants of human α-CGRP with single alanine substitutions were generated by peptide synthesis. Their amino acid sequences are shown in Table 4 along with all the other peptides used in the Biacore analysis. Affinities of Fab fragments of the anti-CGRP antibodies to these variants were determined using Biacore as described above. As shown in FIG. 1, all 12 antibodies target a C-terminal epitope, with amino acid F37 being the most crucial residue. Mutation of F37 to alanine significantly lowered the affinity or even completely knocked out binding of the anti-CGRP antibodies to the peptide. The next most important amino acid residue is G33, however, only the high affinity antibodies (7E9, 8B6, 10A8, and 7D11) were affected by alanine replacement at this position. Amino acid residue S34 also plays a significant, but lesser, role in the binding of these four high affinity antibodies.

TABLE 2

Characteristics of the anti-CGRP monoclonal antibodies' binding to human α-CGRP and their antagonist activity

| Antibodies | $K_D$ to human α-CGRP at 25° C. (nM) | $K_D$ to human α-CGRP at 37° C. (nM) | Cell-based blocking human α-CGRP binding to its receptor at 25° C. (measured by cAMP activation) | $IC_{50}$ (nM binding sites) at 25° C. (room temp.) measured in radioligand binding assay. |
|---|---|---|---|---|
| 7E9 | 1.0 | 0.9 | Yes | 2.5 |
| 8B6 | 1.1 | 1.2 | Yes | 4.0 |
| 10A8 | 2.1 | 3.0 | Yes | n.d. |
| 7D11 | 4.4 | 5.4 | Yes | n.d. |
| 6H2 | 9.3 | 42 | Yes | 12.9 |
| 4901 | 61 | 139 | Yes | 58 |
| 14E10 | 80 | 179 | Yes | n.d. |
| 9B8 | 85 | 183 | No | n.d. |
| 13C2 | 94 | 379 | No | n.d. |
| 14A9 | 148 | 581 | No | n.d. |
| 6D5 | 210 | 647 | No | n.d. |
| 1C5 | 296 | 652 | No | n.d. |

Note:
Antibody 4901 is commercially available (Sigma, Product No. C7113).
n.d. = not determined

TABLE 3

Characteristics of the anti-CGRP monoclonal antibodies' binding to rat α-CGRP and antagonist activity

| Antibodies | $K_D$ to rat α-CGRP at 37° C. (nM) | Cell-based blocking of binding of rat α-CGRP to its receptor at 25° C. (measured by cAMP activation) | In vivo blocking in saphenous nerve assay |
|---|---|---|---|
| 4901 | 3.4 | Yes | Yes |
| 7E9 | 47 | Yes | Yes |

TABLE 3-continued

Characteristics of the anti-CGRP monoclonal antibodies' binding to rat α-CGRP and antagonist activity

| Antibodies | $K_D$ to rat α-CGRP at 37° C. (nM) | Cell-based blocking of binding of rat α-CGRP to its receptor at 25° C. (measured by cAMP activation) | In vivo blocking in saphenous nerve assay |
|---|---|---|---|
| 6H2 | 54 | No | No |
| 8B6 | 75 | Yes | Yes |
| 7D11 | 218 | Yes | Yes |
| 10A8 | 451 | No | n.d. |
| 9B8 | 876 | No | n.d. |
| 14E10 | 922 | No | n.d. |
| 13C2 | >1000 | No | n.d. |
| 14A9 | >1000 | No | n.d. |
| 6D5 | >1000 | No | n.d. |
| 1C5 | >1000 | No | n.d. |

"n.d." indicates no test was performed for the antibody.

TABLE 4

Amino acid sequences of human α-CGRP fragments (SEQ ID NOS: 15-40) and related peptides (SEQ ID NOS: 41-47). All peptides are C-terminally amidated except SEQ ID NOS: 36-40. Residues in bold indicate point mutations.

| CGRP | Amino acid sequence | SEQ ID NO |
|---|---|---|
| 1-37 (WT) | ACDTATCVTHRLAGLLSRSGGVVKNNFVPTNVGSKAF | 15 |
| 8-37 | VTHRLAGLLSRSGGVVKNNFVPTNVGSKAF | 16 |
| 19-37 | SGGVVKNNFVPTNVGSKAF | 17 |
| P29A (19-37) | SGGVVKNNFVATNVGSKAF | 18 |
| K35A (19-37) | SGGVVKNNFVPTNVGSAAF | 19 |
| K35E (19-37) | SGGVVKNNFVPTNVGSEAF | 20 |
| K35M (19-37) | SGGVVKNNFVPTNVGSMAF | 21 |
| K35Q (19-37) | SGGVVKNNFVPTNVGSQAF | 22 |
| F37A (19-37) | SGGVVKNNFVPTNVGSKAA | 23 |
| 25-38A | NNFVPTNVGSKAFA | 24 |
| 25-37 | NNFVPTNVGSKAF | 25 |
| F27A (25-37) | NNAVPTNVGSKAF | 26 |
| V28A (25-37) | NNFAPTNVGSKAF | 27 |
| P29A (25-37) | NNFVATNVGSKAF | 28 |
| T30A (25-37) | NNFVPANVGSKAF | 29 |
| N31A (25-37) | NNFVPTAVGSKAF | 30 |
| V32A (25-37) | NNFVPTNAGSKAF | 31 |
| G33A (25-37) | NNFVPTNVASKAF | 32 |
| S34A (25-37) | NNFVPTNVGAKAF | 33 |
| F37A (25-37) | NNFVPTNVGSKAA | 34 |
| 26-37 | NFVPTNVGSKAF | 35 |
| 19-37-COOH | SGGVVKNNFVPTNVGSKAF | 36 |
| 19-36-COOH | SGGVVKNNFVPTNVGSKA | 37 |
| 1-36-COOH | ACDTATCVTHRLAGLLSRSGGVVKNNFVPTNVGSKA | 38 |
| 1-19-COOH | ACDTATCVTHRLAGLLSRS | 39 |
| 1-13-COOH | ACDTATCVTHRLA | 40 |
| rat α (1-37) | SCNTATCVTHRLAGLLSRSGGVVKDNFVPTNVGSEAF | 41 |

TABLE 4-continued

Amino acid sequences of human α-CGRP fragments (SEQ ID NOS: 15-40) and related peptides (SEQ ID NOS: 41-47). All peptides are C-terminally amidated except SEQ ID NOS: 36-40. Residues in bold indicate point mutations.

| CGRP | Amino acid sequence | SEQ ID NO |
|---|---|---|
| rat α (19-37) | SGGVVKDNFVPTNVGSEAF | 42 |
| human β (1-37) | ACNTATCVTHRLAGLLSRSGGMVKSNFVPTNVGSKAF | 43 |
| rat β (1-37) | SCNTATCVTHRLAGLLSRSGGVVKDNFVPTNVGSKAF | 44 |
| Human calcitonin (1-32) | CGNLSTCMLGTYTQDFNKFHTFPQTAIGVGAP | 45 |
| Human amylin (1-37) | KCNTATCATQRLANFLVHSSNNFGAILSSTNVGSNTY | 46 |
| Human adrenomedullin (1-52) | YRQSMNNFQGLRSFGCRFGTCTVQKLAHQIYQFTDK DKDNVAPRSKISPQGY | 47 |

Example 2: Screening of Anti-CGRP Antagonist Antibodies Using In Vitro Assays

Murine anti-CGRP antibodies were further screened for antagonist activity in vitro using cell based cAMP activation assay and binding assay.

Antagonist activity measured by cAMP assay. Five microliters of human or rat α-CGRP (final concentration 50 nM) in the presence or absence of an anti-CGRP antibody (final concentration 1-3000 nM), or rat α-CGRP or human α-CGRP (final concentration 0.1 nM-10 μM; as a positive control for c-AMP activation) was dispensed into a 384-well plate (Nunc, Cat. No. 264657). Ten microliters of cells (human SK-N-MC if human α-CGRP is used, or rat L6 from ATCC if rat α-CGRP is used) in stimulation buffer (20 mM HEPES, pH 7.4, 146 mM NaCl, 5 mM KCl, 1 mM $CaCl_2$, 1 mM $MgCl_2$, and 500 uM 3-Isobutyl-1-methylxanthine (IBMX)) were added into the wells of the plate. The plate was incubated at room temperature for 30 min.

After the incubation, cAMP activation was performed using HitHunter™ Enzyme Fragment Complementation Assay (Applied Biosystems) following manufacture's instruction. The assay is based on a genetically engineered β-galactosidase enzyme that consists of two fragments—termed Enzyme Acceptor (EA) and Enzyme Donor (ED). When the two fragments are separated, the enzyme is inactive. When the fragments are together they can recombine spontaneously to form active enzyme by a process called complementation. The EFC assay platform utilizes an ED-cAMP peptide conjugate in which cAMP is recognized by anti-cAMP. This ED fragment is capable of reassociation with EA to form active enzyme. In the assay, anti-cAMP antibody is optimally titrated to bind ED-cAMP conjugate and inhibit enzyme formation. Levels of cAMP in cell lysate samples compete with ED-cAMP conjugate for binding to the anti-cAMP antibody. The amount of free ED conjugate in the assay is proportional to the concentration of cAMP. Therefore, cAMP is measured by the formation of active enzyme that is quantified by the turnover of β-galactosidase luminescent substrate. The cAMP activation assay was performed by adding 10 μl of lysis buffer and anti-cAMP antibody (1:1 ratio) following by incubation at room temperature for 60 min. Then 10 μl of ED-cAMP reagent was added into each well and incubated for 60 minutes at room temperature. After the incubation, 20 μl of EA reagent and CL mixture (containing the substrate) (1:1 ratio) was added into each well and incubated for 1-3 hours or overnight at room temperature. The plate was read at 1 second/well on PMT instrument or 30 seconds/place on imager. The antibodies that inhibit activation of cAMP by α-CGRP were identified (referred to as "yes") in Tables 2 and 3 above. Data in Tables 2 and 3 indicate that antibodies that demonstrated antagonist activity in the assay generally have high affinity. For example, antibodies having $K_D$ (determined at 25° C.) of about 80 nM or less to human α-CGRP or having $K_D$ (determined at 37° C.) of about 47 nM or less to rat α-CGRP showed antagonist activity in this assay.

Radioligand binding assay. Binding assay was performed to measure the $IC_{50}$ of anti-CGRP antibody in blocking the CGRP from binding to the receptor as described previously. Zimmermann et al., Peptides 16:421-4, 1995; Mallee et al., J. Biol. Chem. 277:14294-8, 2002. Membranes (25 μl) from SK-N-MC cells were incubated for 90 min at room temperature in incubation buffer (50 mM Tris-HCL, pH 7.4, 5 mM MgCL2, 0.1% BSA) containing 10 pM $^{125}$I-human α-CGRP in a total volume of 1 mL. To determine inhibition concentrations ($IC_{50}$), antibodies or unlabeled CGRP (as a control), from a about 100 fold higher stock solution were dissolved at varying concentrations in the incubation buffer and incubated at the same time with membranes and 10 pM $^{125}$I-human α-CGRP. Incubation was terminated by filtration through a glass microfiber filter (GF/B, 1 μm) which had been blocked with 0.5% polyethylemimine. Dose response curves were plotted and $K_i$ values were determined by using the equation: $K_i=IC_{50}/(1+([ligand]/K_D))$; where the equilibrium dissociation constant $K_D$=8 pM for human α-CGRP to CGRP1 receptor as present in SK-N-MC cells, and $B_{max}$=0.025 pmol/mg protein. The reported $IC_{50}$ value (in terms of IgG molecules) was converted to binding sites (by multiplying it by 2) so that it could be compared with the affinities ($K_D$) determined by Biacore (see Table 2).

Table 2 shows the $IC_{50}$ of murine antibodies 7E9, 8B6, 6H2 and 4901. Data indicate that antibody affinity generally correlates with $IC_{50}$: antibodies with higher affinity (lower $K_D$ values) have lower $IC_{50}$ in the radioligand binding assay.

Example 3: Effect of Anti-CGRP Antagonist Antibodies on Skin Vasodilatation Induced by Stimulation of Rat Saphenous Nerve To test antagonist activity of anti-CGRP antibodies, effect of the antibodies on skin vasodilatation by stimulation of rat saphenous nerve was tested using a rat model described previously. Escott et al., Br. J. Pharmacol. 110:772-776, 1993. In this rat model, electrical stimulation of saphenous nerve induces release of CGRP from nerve endings, resulting in an increase in skin blood flow. Blood flow in the foot skin of male Sprague Dwaley rats (170-300 g, from Charles River Hollister) was measured after saphenous nerve stimulation. Rats were maintained under anesthesia with 2% isoflurane. Bretylium tosylate (30 mg/kg, administered i.v.) was given at the beginning of the experiment to minimize vasoconstriction due to the concomitant stimulation of sympathetic fibers of the saphenous nerve. Body temperature was maintained at 37° C. by the use of a rectal probe thermostatically connected to a temperature controlled heating pad. Compounds including antibodies, positive control (CGRP 8-37), and vehicle (PBS, 0.01% Tween 20) were given intravenously through the right femoral vein, except for the experiment shown in FIG. 3, the test compound and the control were injected through tail vein, and for experiments shown in FIGS. 2A and 2B, antibodies 4901 and 7D11 were injected intraperitoneally (IP). Positive control compound CGRP 8-37 (vasodilatation antagonist), due to its short half-life, was given 3-5 min before nerve stimulation at 400 nmol/kg (200 µl). Tan et al., Clin. Sci. 89:656-73, 1995. The antibodies were given in different doses (1 mg/kg, 2.5 mg/kg, 5 mg/kg, 10 mg/kg, and 25 mg/kg).

Figure 2B:
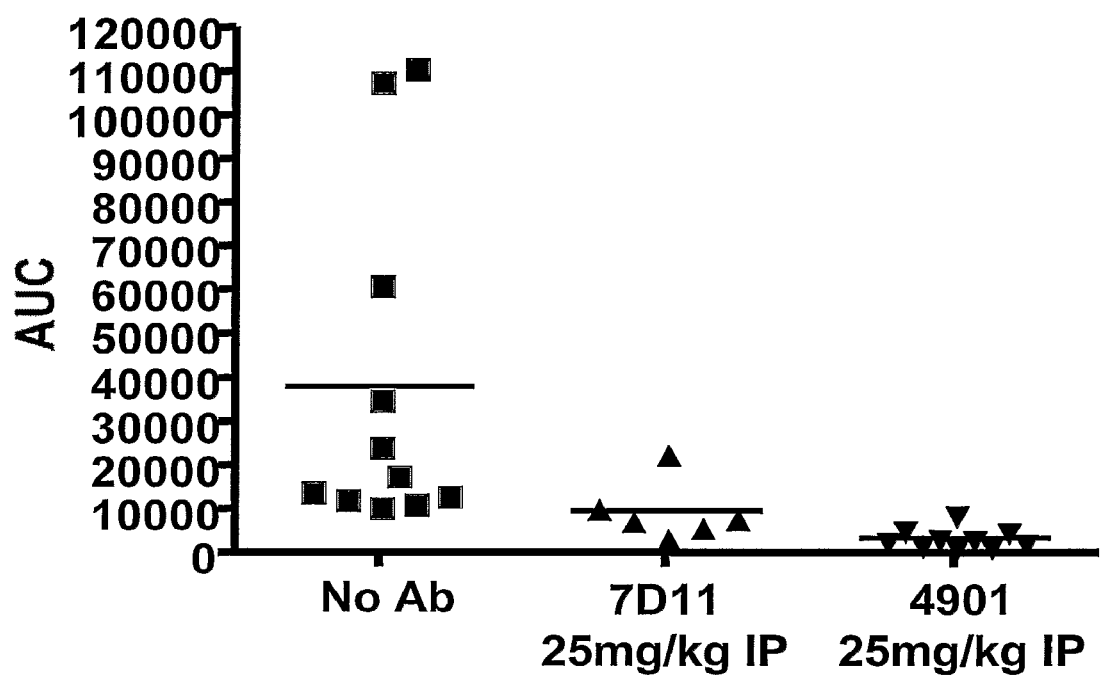

For experiments shown in FIGS. 2A and 2B, antibody 4901 (25 mg/kg), antibody 7D11 (25 mg/kg), or vehicle control (PBS with 0.01% Tween 20) was administered intraperitoneally (IP) 72 hours before the electrical pulse stimulation. For experiment shown in FIG. 3, antibody 4901 (1 mg/kg, 2.5 mg/kg, 5 mg/kg, or 25 mg/kg) or vehicle control (PBS with 0.01% Tween 20) was administered intravenously 24 hours before the electrical pulse stimulation. After administration of the antibodies or vehicle control, the saphenous nerve of the right hindlimb was exposed surgically, cut proximally and covered with plastic wrap to prevent drying. A laser Doppler probe was placed over the medio-dorsal side of the hindpaw skin, which is the region innervated by the saphenous nerve. Skin blood flow, measured as blood cell flux, was monitored with a laser Doppler flow meter. When a stable base-line flux (less than 5% variation) was established for at least 5 min, the nerve was placed over platinum bipolar electrodes and electrically stimulated with 60 pulses (2 Hz, 10 V, 1 ms, for 30 sec) and then again 20 minutes later. Cumulative change in skin blood flow was estimated by the area under the flux-time curve (AUC, which is equal to change in flux multiplied by change in time) for each flux response to electrical pulse stimulation. The average of the blood flow response to the two stimulations was taken. Animals were kept under anesthesia for a period of one to three hours.

Figure 3:
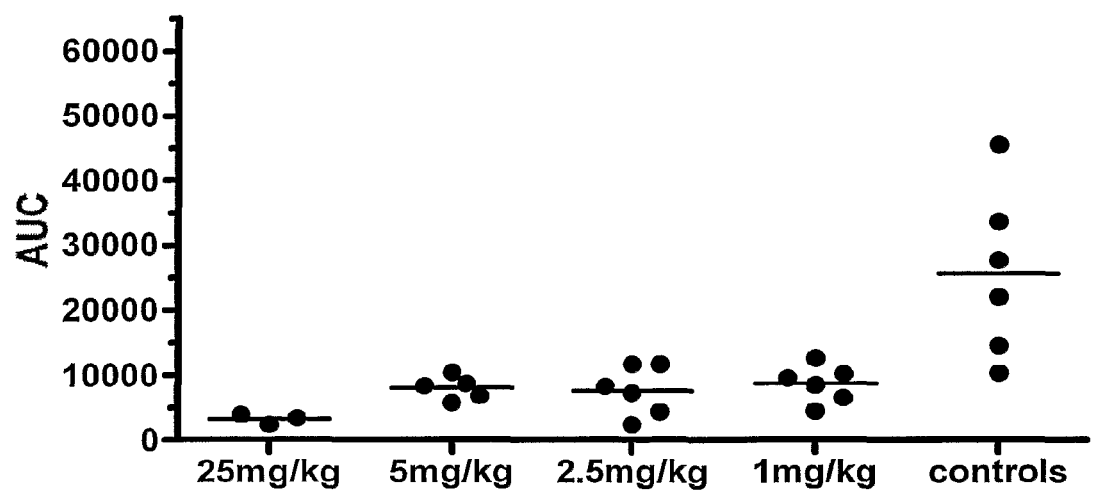
FIG. 3 shows the effect of administering different dosage of antibody 4901 (25 mg/kg, 5 mg/kg, 2.5 mg/kg, or 1 mg/kg) on skin blood flow measured as blood cell flux after electrical pulse stimulation for 30 seconds. Antibodies were administered intravenously (IV) 24 hours before electrical pulse stimulation. Each point in the graph represents AUC of one rat treated under the conditions as indicated. The line in the graph represents average AUC of rats treated under the condition as indicated.

As shown in FIG. 2A and FIG. 2B, blood flow increase stimulated by applying electronic pulses on saphenous nerve was inhibited by the presence of CGRP 8-37 (400 nmol/kg, administered i.v.), antibody 4901 (25 mg/kg, administered ip), or antibody 7D11 (25 mg/kg, administered ip) as compared to the control. CGRP 8-37 was administered 3-5 min before the saphenous nerve stimulation; and antibodies were administered 72 hours before the saphenous nerve stimulation. As shown in FIG. 3, blood flow increase stimulated by applying electronic pulses on saphenous nerve was inhibited by the presence of antibody 4901 at different doses (1 mg/kg, 2.5 mg/kg, 5 mg/kg, and 25 mg/kg) administered intravenously at 24 h before the saphenous nerve stimulation.

Figure 4A:
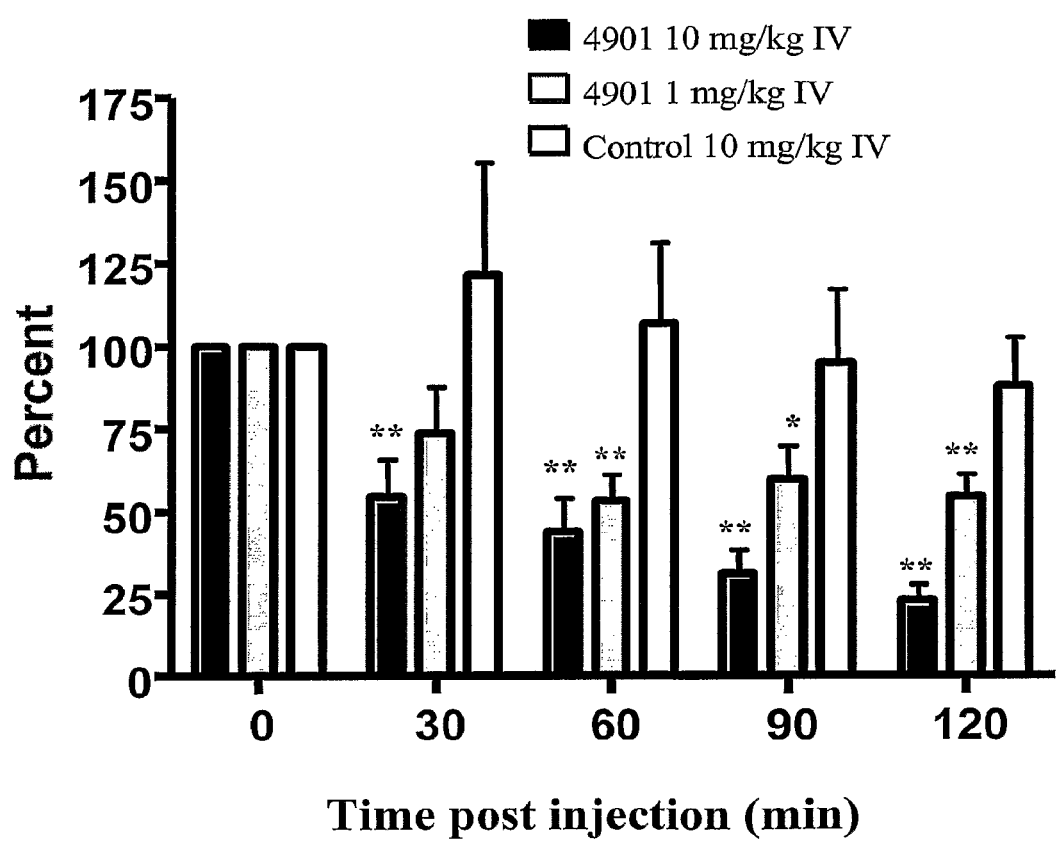
FIGS. 4A and 4B show the effect of administering antibody 4901 (1 mg/kg or 10 mg/kg, i.v.), antibody 7E9 (10 mg/kg, i.v.), and antibody 8B6 (10 mg/kg, i.v.) on skin blood flow measured as blood cell flux after electrical pulse stimulation for 30 seconds. Antibodies were administered intravenously (i.v.) followed by electrical pulse stimulation at 30 min, 60 min, 90 min, and 120 min after antibody administration. Y axis represents percent of AUC as compared to level of AUC when no antibody was administered (time 0). X axis represents time (minutes) period between the administration of antibodies and electrical pulse stimulation. "*" indicates P<0.05, and "**" indicates P<0.01, as compared to time 0. Data were analyzed using one-way ANOVA with a Dunnett's Multiple comparison test.
Figure 4B:
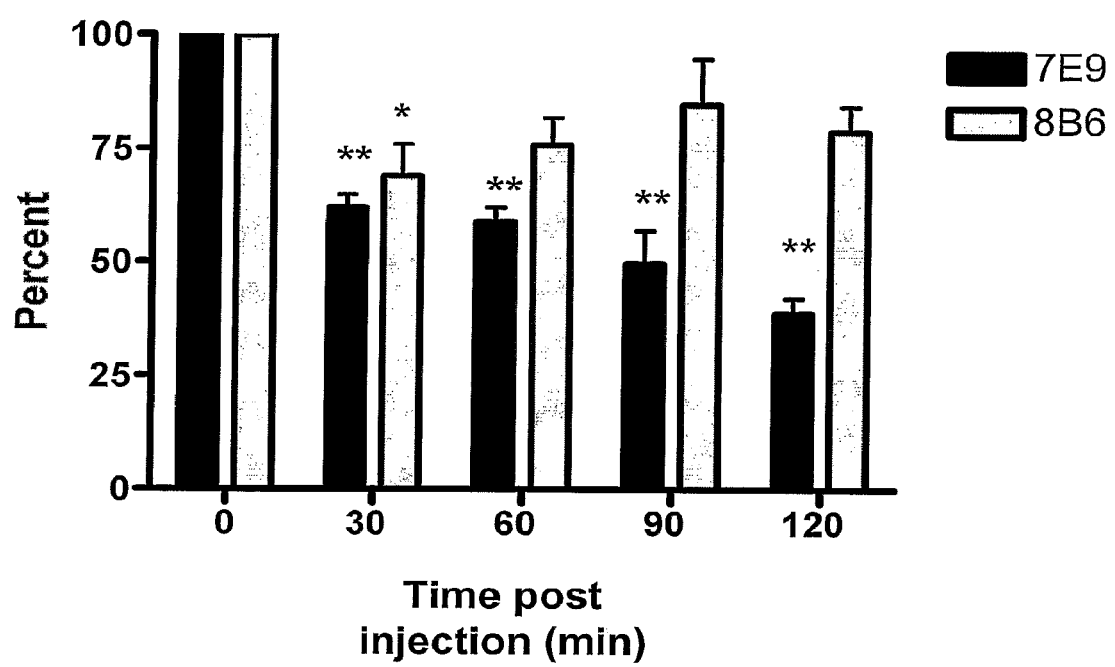

For experiments shown in FIGS. 4A and 4B, saphenous nerve was exposed surgically before antibody administration. The saphenous nerve of the right hindlimb was exposed surgically, cut proximally and covered with plastic wrap to prevent drying. A laser Doppler probe was placed over the medio-dorsal side of the hindpaw skin, which is the region innervated by the saphenous nerve. Skin blood flow, measured as blood cell flux, was monitored with a laser Doppler flow meter. Thirty to forty five minutes after bretylium tosylate injection, when a stable base-line flux (less than 5% variation) was established for at least 5 min, the nerve was placed over platium bipolar electrodes and electrically stimulated (2 Hz, 10V, 1 ms, for 30 sec) and again 20 minutes later. The average of the blood flow flux response to these two stimulations was used to establish the baseline response (time 0) to electrical stimulation. Antibody 4901 (1 mg/kg or 10 mg/kg), antibody 7E9 (10 mg/kg), antibody 8B6 (10 mg/kg), or vehicle (PBS with 0.01% Tween 20) were then administered intravenously (i.v.). The nerve was subsequently stimulated (2 Hz, 10V, 1 ms, for 30 sec) at 30 min, 60 min, 90 min, and 120 min after antibody or vehicle administration. Animals were kept under anesthesia for a period of approximately three hours. Cumulative change in skin blood flow was estimated by the area under the flux-time curve (AUC, which is equal to change in flux multiplied by change in time) for each flux response to electrical pulse stimulations.

As shown in FIG. 4A, blood flow increase stimulated by applying electronic pulses on saphenous nerve was significantly inhibited by the presence of antibody 4901 1 mg/kg administered i.v., when electronic pulse stimulation was applied at 60 min, 90 min, and 120 min after the antibody administration, and blood flow increase stimulated by applying electronic pulses on saphenous nerve was significantly inhibited by the presence of antibody 4901 10 mg/kg administered i.v., when electronic pulse stimulation was applied at 30 min, 60 min, 90 min, and 120 min after the antibody administration. FIG. 4B shows that blood flow increase stimulated by applying electronic pulses on saphenous nerve was significantly inhibited by the presence of antibody 7E9 (10 mg/kg, administered i.v.) when electronic pulse stimulation was applied at 30 min, 60 min, 90 min, and 120 min after antibody administration, and by the presence of antibody 8B6 (10 mg/kg, administered i.v.) when electronic pulse stimulation was applied at 30 min after antibody administration.

These data indicate that antibodies 4901, 7E9, 7D11, and 8B6 are effective in blocking CGRP activity as measured by skin vasodilatation induced by stimulation of rat saphenous nerve.

Example 4. Characterization of Anti-CGRP Antibody G1 and its Variants

Amino acid sequences for the heavy chain variable region and light chain variable region of anti-CGRP antibody G1 are shown in FIG. 5. The following methods were used for expression and characterization of antibody G1 and its variants.

Expression vector used. Expression of the Fab fragment of the antibodies was under control of an IPTG inducible lacZ promoter similar to that described in Barbas (2001)

Phage display: a laboratory manual, Cold Spring Harbor, N.Y., Cold Spring Harbor Laboratory Press pg 2.10. Vector pComb3x), however, modifications included addition and expression of the following additional domains: the human Kappa light chain constant domain and the CH1 constant domain of IgG2 human immunoglobulin, Ig gamma-2 chain C region, protein accession number P01859; Immunoglobulin kappa light chain (homosapiens), protein accession number CAA09181.

Small scale Fab preparation. From *E. Coli* transformed (either using electroporation-competent TG1 cells or chemically-competent Top 10 cells) with a Fab library, single colonies were used to inoculate both a master plate (agar LB+carbenicillin (50 ug/mL)+2% glucose) and a working plate (2 mL/well, 96-well/plate) where each well contained 1.5 mL LB+carbenicillin (50 ug/mL)+2% glucose. A gas permeable adhesive seal (ABgene, Surrey, UK) was applied to the plate. Both plates were incubated at 30° C. for 12-16 h; the working plate was shaken vigorously. The master plate was stored at 4° C. until needed, while the cells from the working plate were pelleted (4000 rpm, 4° C., 20 mins) and resuspended in 1.0 mL LB+carbenicillin (50 ug/mL)+ 0.5 mM IPTG to induce expression of Fabs by vigorous shaking for 5 h at 30° C. Induced cells were centrifuges at 4000 rpm, 4° C. for 20 mins and resuspended in 0.6 mL Biacore HB-SEP buffer (10 mM Hepes pH 7.4, 150 mM NaCl, 3 mM EDTA, 0.005% v/v P20). Lysis of HB-SEP resuspended cells was accomplished by freezing (-80° C.) and then thawing at 37° C. Cell lysates were centrifuged at 4000 rpm, 4° C. for 1 hour to separate the debris from the Fab-containing supernatants, which were subsequently filtered (0.2 um) using a Millipore MultiScreen Assay System 96-Well Filtration Plate and vacuum manifold. Biacore was used to analyze filtered supernatants by injecting them across CGRPs on the sensor chip. Affinity-selected clones expressing Fabs were rescued from the master plate, which provided template DNA for PCR, sequencing, and plasmid preparation.

Large scale Fab preparation. To obtain kinetic parameters, Fabs were expressed on a larger scale as follows. Erlenmeyer flasks containing 150 mL LB+carbenicillin (50 ug/mL)+2% glucose were inoculated with 1 mL of a "starter" overnight culture from an affinity-selected Fab-expressing *E. Coli* clone. The remainder of the starter culture (~3 mL) was used to prepare plasmid DNA (QIAprep mini-prep, Qiagen kit) for sequencing and further manipulation. The large culture was incubated at 30° C. with vigorous shaking until an $OD_{600\ nm}$ of 1.0 was attained (typically 12-16 h). The cells were pelleted by centrifuging at 4000 rpm, 4° C. for 20 mins, and resuspended in 150 mL LB+carbenicillin (50 ug/mL)+0.5 mM IPTG. After 5 h expression at 30° C., cells were pelleted by centrifuging at 4000 rpm, 4° C. for 20 mins, resuspended in 10 mL Biacore HBS-EP buffer, and lysed using a single freeze (-80° C.)/thaw (37° C.) cycle. Cell lysates were pelleted by centrifuging at 4000 rpm, 4° C. for 1 hour, and the supernatant was collected and filtered (0.2 um). Filtered supernatants were loaded onto Ni-NTA superflow sepharose (Qiagen, Valencia. Calif.) columns equilibrated with PBS, pH 8, then washed with 5 column volumes of PBS, pH 8. Individual Fabs eluted in different fractions with PBS (pH 8)+300 mM Imidazole. Fractions containing Fabs were pooled and dialyzed in PBS, then quantified by ELISA prior to affinity characterization.

Full antibody preparation. For expression of full antibodies, heavy and light chain variable regions were cloned in mammalian expression vectors and transfected using lipofectamine into HEK 293 cells for transient expression. Antibodies were purified using protein A using standard methods.

Vector pDb.CGRP.hFcGI is an expression vector comprising the heavy chain of the G1 antibody, and is suitable for transient or stable expression of the heavy chain. Vector pDb.CGRP.hFcGI has nucleotide sequences corresponding to the following regions: the murine cytomegalovirus promoter region (nucleotides 7-612); a synthetic intron (nucleotides 613-1679); the DHFR coding region (nucleotides 688-1253); human growth hormone signal peptide (nucleotides 1899-1976); heavy chain variable region of G1 (nucleotides 1977-2621); human heavy chain IgG2 constant region containing the following mutations: A330P331 to S330S331 (amino acid numbering with reference to the wildtype IgG2 sequence; see Eur. J. Immunol. (1999) 29:2613-2624). Vector pDb.CGRP.hFcGI was deposited at the ATCC on Jul. 15, 2005, and was assigned ATCC Accession No. PTA-6867.

Vector pEb.CGRP.hKGI is an expression vector comprising the light chain of the G1 antibody, and is suitable for transient expression of the light chain. Vector pEb.CGRP.hKGI has nucleotide sequences corresponding to the following regions: the murine cytomegalovirus promoter region (nucleotides 2-613); human EF-1 intron (nucleotides 614-1149); human growth hormone signal peptide (nucleotides 1160-1237); antibody G1 light chain variable region (nucleotides 1238-1558); human kappa chain constant region (nucleotides 1559-1882). Vector pEb.CGRP.hKGI was deposited at the ATCC on Jul. 15, 2005, and was assigned ATCC Accession No. PTA-6866.

Biacore assay for affinity determination. Affinities of G1 monoclonal antibody and its variants were determined at either 25° C. or 37° C. using the Biacore3000™ surface plasmon resonance (SPR) system (Biacore, INC, Piscataway N.J.). Affinity was determined by capturing N-terminally biotinylated CGRP or fragments via pre-immobilized streptavidin (SA sensor chip) and measuring the binding kinetics of antibody G1 Fab fragments or variants titrated across the CGRP or fragment on the chip. All Biacore assays were conducted in HBS-EP running buffer (10 mM HEPES pH 7.4, 150 mM NaCl, 3 mM EDTA, 0.005% v/v polysorbate P20). CGRP surfaces were prepared by diluting the N-biotinylated CGRP to a concentration of less than 0.001 mg/mL into HBS-EP buffer and injecting it across the SA sensor chip using variable contact times. Low capacity surfaces, corresponding to capture levels <50 response units (RU) were used for high-resolution kinetic studies, whereas high capacity surfaces (about 800 RU of captured CGRP) were used for concentration studies, screening, and solution affinity determinations. Kinetic data were obtained by diluting antibody G1 Fab serially in two- or three-fold increments to concentrations spanning 1 uM-0.1 nM (aimed at 0.1-10× estimated $K_D$). Samples were typically injected for 1 minute at 100 μL/min and dissociation times of at least 10 minutes were allowed. After each binding cycle, surfaces were regenerated with 25 mM NaOH in 25% v/v ethanol, which was tolerated over hundreds of cycles. An entire titration series (typically generated in duplicate) was fit globally to a 1:1 Langmuir binding model using the BIAevaluation program. This returned a unique pair of association and dissociation kinetic rate constants (respectively, $k_{on}$ and $k_{off}$) for each binding interaction, whose ratio gave the equilibrium dissociation constant ($K_D=k_{off}/k_{on}$). Affinities ($K_D$ values) determined in this way are listed in Tables 6 and 7.

High-resolution analysis of binding interactions with extremely slow offrates. For interactions with extremely slow offrates (in particular, antibody G1 Fab binding to human α-CGRP on the chip at 25° C.), affinities were obtained in a two-part experiment. The protocol described above was used with the following modifications. The association rate constant ($k_{on}$) was determined by injecting a 2-fold titration series (in duplicate) spanning 550 nM-1 nM for 30 sec at 100 uL/min and allowing only a 30 sec dissociation phase. The dissociation rate constant ($k_{off}$) was determined by injecting three concentrations (high, medium, and low) of the same titration series in duplicate for 30 sec and allowing a 2-hour dissociation phase. The affinity ($K_D$) of each interaction was obtained by combining the $k_{on}$ and $k_{off}$ values obtained in both types of experiments, as shown in Table 5.

Determining solution affinity by Biacore. The solution affinity of antibody G1 for rat α-CGRP and F37A (19-37) human α-CGRP was measured by Biacore at 37° C. A high capacity CGRP chip surface was used (the high-affinity human α-CGRP was chosen for detection purposes) and HBS-EP running buffer was flowed at 5 uL/min. Antibody G1 Fab fragment at a constant concentration of 5 nM (aimed to be at or below the expected $K_D$ of the solution-based interaction) was pre-incubated with competing peptide, either rat α-CGRP or F37A (19-37) human α-CGRP, at final concentrations spanning 1 nM to 1 uM in 3-fold serial dilutions. Antibody G1 Fab solutions in the absence or presence of solution-based competing peptide, were injected across CGRP on the chip and the depletion of binding responses detected at the chip surface as a result of solution competition was monitored. These binding responses were converted to "free Fab concentrations" using a calibration curve, which was constructed by titrating antibody G1 Fab alone (5, 2.5, 1.25, 0.625, 0.325 and 0 nM) across the CGRP on the chip. "Free Fab concentrations" were plotted against the concentration of competing solution-based peptide used to generate each data point and fit to a solution affinity model using the BIAevaluation software. The solution affinities determined (indirectly) in this way are shown in Tables 5 and 7 and were used to validate the affinities obtained when Fabs are injected directly across N-biotinylated CGRPs on a SA chip. The close agreement between the affinities determined by these two methods confirms that tethering an N-biotinylated version of the CGRP to the chip does not alter its native solution binding activity.

Table 5 below shows the binding affinities of antibody G1 to human α-CGRP, human β-CGRP, rat α-CGRP, and rat β-CGRP determined by Biacore, by flowing Fab fragments across N-biotinylated CGRPs on a SA chip. To better resolve the affinities of binding interactions with extremely slow offrates, affinities were also determined in a two-part experiment to complement this assay orientation, the solution affinity of the rat α-CGRP interaction was also determined (as described above). The close agreement of the affinities measured in both assay orientations confirms that the binding affinity of the native rat α-CGRP in solution is not altered when it is N-biotinylated and tethered to a SA chip.

TABLE 5

Binding affinities of antibody G1 Fabs titrated across CGRPs on the chip

| CGRP on chip | Temp. (° C.) | $k_{on}$ (1/Ms) | $k_{off}$(1/s) | $K_D$ (nM) |
|---|---|---|---|---|
| Human α-CGRP | 25 | $1.86 \times 10^5$ | $7.80 \times 10^{-6}$ | 0.042 (7%, n = 4)* |
| Human α-CGRP | 37 | $5.78 \times 10^5$ | $3.63 \times 10^{-5}$ | 0.063 (4%, n = 2)* |
| Human β-CGRP | 37 | $4.51 \times 10^5$ | $6.98 \times 10^{-5}$ | 0.155 |
| Rat α-CGRP | 25 | $5.08 \times 10^4$ | $6.18 \times 10^{-5}$ | 1.22 (12%, n = 2)* |
| Rat α-CGRP | 37 | $1.55 \times 10^5$ | $3.99 \times 10^{-4}$ | 2.57* (Solution $K_D$ = 10 (50% n = 4)** |
| Rat β-CGRP | 37 | $5.16 \times 10^5$ | $7.85 \times 10^{-5}$ | 0.152 |

*Affinities for α-CGRPs (rat and human) were determined in a high-resolution two-part experiment, in which the dissociation phase was monitored for 2 hours (the values for $k_{on}$, $k_{off}$, and $K_D$ represent the average of n replicate experiments with the standard deviation expressed as a percent variance). Affinities for β-CGRPs (rat and human) were determined by global analysis using only a 20-min dissociation phase, which was not accurate enough to quantify their extremely offrates (their offrates are likely slower than stated here and therefore their affinities are likely even higher). Antibody G1 Fab dissociated extremely slowly from all CGRPs (except α-rat CGRP) with offrates that approached the resolution limit of the Biacore assay (especially at 25° C.).

**Solution affinity determined by measuring the depletion of binding responses detected at CGRP on the chip for antibody G1 Fab pre-incubated with solution-based rat α-CGRP competitor.

Table 6 below shows antibodies having the amino acid sequence variation as compared to antibody G1 and their affinities to both rat α-CGRP and human α-CGRP. All amino acid substitutions of the variants shown in Table 6 are described relative to the sequence of G1. The binding affinities of Fab fragments were determined by Biacore by flowing them across CGRPs on a SA chip.

TABLE 6

Amino acid sequences and binding affinity data for antibody G1 variants determined at 37° C. by Biacore.

| Clone | L1 | L2 | H2 | HC-FW3 | α-rat $k_{off}$(1/s) | α-rat $K_D$ (nM) | α-human $k_{off}$(1/s) | α-human $K_D$ (nM) |
|---|---|---|---|---|---|---|---|---|
| G1 | | | | | $3.99 \times 10^{-4}$ | 2.57 | $3.63 \times 10^{-5}$ | 0.063 |
| M1 | | | | A100L | $1.10 \times 10^{-3}$ | | $1.73 \times 10^{-4}$ | |
| M2 | | | | L99A A100R | $2.6 \times 10^{-3}$ | 58 | $3.1 \times 10^{-4}$ | 3 |
| M3 | | | | L99A A100S | $2.0 \times 10^{-3}$ | 61 | $2.1 \times 10^{-4}$ | 1.7 |
| M4 | | | | L99A A100V | $1.52 \times 10^{-3}$ | 84.4 | $6.95 \times 10^{-5}$ | 0.43 |
| M5 | | | | L99A A100Y | $7.35 \times 10^{-4}$ | 40.8 | $3.22 \times 10^{-5}$ | 0.20 |
| M6 | | | | L99N | $7.84 \times 10^{-4}$ | 43.6 | $1.33 \times 10^{-4}$ | 0.83 |
| M7 | | | | L99N A100C | $9.18 \times 10^{-4}$ | 51.0 | $2.43 \times 10^{-4}$ | 1.52 |

TABLE 6-continued

Amino acid sequences and binding affinity data for antibody G1 variants determined at 37° C. by Biacore.

| Clone | L1 | L2 | H2 | HC-FW3 | α-rat $k_{off}$(1/s) | α-rat $K_D$ (nM) | α-human $k_{off}$(1/s) | α-human $K_D$ (nM) |
|---|---|---|---|---|---|---|---|---|
| M8 |  |  |  | L99N A100G | $7.45 \times 10^{-4}$ | 41.4 | $9.20 \times 10^{-5}$ | 0.58 |
| M9 |  |  |  | L99N A100Y | n.d. | n.d. | $1.00 \times 10^{-5}$ | 0.06 |
| M10 |  |  |  | L99S A100S | $1.51 \times 10^{-3}$ | 83.9 | $1.73 \times 10^{-4}$ | 1.08 |
| M11 |  |  |  | L99S A100T | $4.83 \times 10^{-3}$ | 268.3 | $2.83 \times 10^{-4}$ | 1.77 |
| M12 |  |  |  | L99S A100V | $1.94 \times 10^{-3}$ | 107.8 | $1.01 \times 10^{-4}$ | 0.63 |
| M13 |  |  |  | L99T A100G | $1.84 \times 10^{-3}$ | 102.2 | $1.86 \times 10^{-4}$ | 1.16 |
| M14 |  |  |  | L99T A100K | n.d. | n.d. | $1.00 \times 10^{-5}$ | 0.06 |
| M15 |  |  |  | L99T A100P | $1.15 \times 10^{-3}$ | 63.9 | $1.58 \times 10^{-5}$ | 0.10 |
| M16 |  |  |  | L99T A100S | $9.96 \times 10^{-4}$ | 55.3 | $1.65 \times 10^{-4}$ | 1.03 |
| M17 |  |  |  | L99T A100V | $2.06 \times 10^{-3}$ | 114.4 | $1.85 \times 10^{-4}$ | 1.16 |
| M18 |  |  |  | L99V A100G | $1.22 \times 10^{-3}$ | 67.8 | $7.03 \times 10^{-5}$ | 0.44 |
| M19 |  |  |  | L99V A100R | n.d. | n.d. | $1.00 \times 10^{-5}$ | 0.06 |
| M20 | R28W |  |  | L99R A100L | $1.44 \times 10^{-3}$ | 80.0 | $1.36 \times 10^{-4}$ | 0.85 |
| M21 | R28W |  |  | L99S | $6.95 \times 10^{-4}$ | 15.2 | $1.42 \times 10^{-4}$ | 1.23 |
| M22 | R28W |  |  | L99T | $1.10 \times 10^{-3}$ | 61.1 | $1.16 \times 10^{-4}$ | 0.73 |
| M23 | R28G |  |  | L99T A100V | $7.99 \times 10^{-4}$ | 44.4 | $1.30 \times 10^{-4}$ | 0.81 |
| M24 | R28L |  |  | L99T A100V | $1.04 \times 10^{-3}$ | 57.8 | $1.48 \times 10^{-4}$ | 0.93 |
| M25 | R28N |  |  | L99T A100V | $1.4 \times 10^{-3}$ | 76 | $1.4 \times 10^{-4}$ | 1.3 |
| M26 | R28N |  | A57G | L99T A100V | $9.24 \times 10^{-4}$ | 51.3 | $1.48 \times 10^{-4}$ | 0.93 |
| M27 | R28N T30A |  |  | L99T A100V | $3.41 \times 10^{-3}$ | 189.4 | $3.57 \times 10^{-4}$ | 2.23 |
| M28 | R28N T30D |  | E54R A57N | L99T A100V | $1.25 \times 10^{-3}$ | 69.4 | $9.96 \times 10^{-5}$ | 0.62 |
| M29 | R28N T30G |  |  | L99T A100V | $3.59 \times 10^{-3}$ | 199.4 | $3.80 \times 10^{-4}$ | 2.38 |
| M30 | R28N T30G |  | E54K A57E | L99T A100V | $6.38 \times 10^{-3}$ | 354.4 | $5.90 \times 10^{-4}$ | 3.69 |
| M31 | R28N T30G |  | E54K A57G | L99T A100V | $3.61 \times 10^{-3}$ | 200.6 | $3.47 \times 10^{-4}$ | 2.17 |
| M32 | R28N T30G |  | E54K A57H | L99T A100V | $2.96 \times 10^{-3}$ | 164.4 | $2.71 \times 10^{-4}$ | 1.69 |
| M33 | R28N T30G |  | E54K A57N S58G | L99T A100V | $9.22 \times 10^{-3}$ | 512.2 | $7.50 \times 10^{-4}$ | 4.69 |
| M34 | R28N T30G |  | E54K A57N S58T | L99T A100V | $2.17 \times 10^{-3}$ | 120.6 | $6.46 \times 10^{-4}$ | 4.04 |
| M35 | R28N T30G |  | E54K A57S | L99T A100V | $3.99 \times 10^{-3}$ | 221.7 | $3.39 \times 10^{-4}$ | 2.12 |
| M36 | R28N T30R |  |  | L99T A100V | $4.79 \times 10^{-3}$ | 266.1 | $2.39 \times 10^{-4}$ | 1.49 |
| M37 | R28N T30S |  | A57G | L99T A100V | $1.45 \times 10^{-3}$ | 80.6 | $2.26 \times 10^{-4}$ | 1.41 |
| M38 | R28N T30W |  |  | L99T A100V | $5.11 \times 10^{-3}$ | 283.9 | $2.18 \times 10^{-4}$ | 1.36 |
| M39 | R28N | G50A L56T | A57N S58Y | L99T A100V | $9.95 \times 10^{-3}$ | 552.8 | $4.25 \times 10^{-4}$ | 2.66 |
| M40 | R28N | G50A L56T | E54K A57L | L99T A100V | 0.36 | 20000.0 | $1.28 \times 10^{-3}$ | 8.00 |
| M41 | R28N | G50A L56T | E54K A57N E64D | L99T A100V | $4.53 \times 10^{-3}$ | 251.7 | $2.10 \times 10^{-4}$ | 1.31 |
| M42 | R28N | G50A L56T | E54K A57N H61F | L99T A100V | $7.52 \times 10^{-3}$ | 417.8 | $4.17 \times 10^{-4}$ | 2.61 |

TABLE 6-continued

Amino acid sequences and binding affinity data for antibody G1 variants determined at 37° C. by Biacore.

| Clone | L1 | L2 | H2 | HC-FW3 | α-rat $k_{off}$(1/s) | α-rat $K_D$ (nM) | α-human $k_{off}$(1/s) | α-human $K_D$ (nM) |
|---|---|---|---|---|---|---|---|---|
| M43 | R28N | G50A L56T | E54K A57N S58C | L99T A100V | $4.53 \times 10^{-3}$ | 251.7 | $2.63 \times 10^{-4}$ | 1.64 |
| M44 | R28N | G50A L56T | E54K A57N S58E | L99T A100V | $\underline{6.13 \times 10^{-3}}$ | $\underline{443}$ | $\underline{2.10 \times 10^{-4}}$ | $\underline{2.05}$ |
| M45 | R28N | G50A L56T | E54K A57N S58E E64D | L99T A100V | $\underline{5.58 \times 10^{-3}}$ | $\underline{259}$ | $\underline{2.11 \times 10^{-4}}$ | $\underline{1.85}$ |
| M46 | R28N | G50A L56T | E54K A57N S58E H61F | L99T A100V | $2.94 \times 10^{-3}$ | 163.3 | $5.39 \times 10^{-4}$ | 3.37 |
| M47 | R28N | G50A L56T | E54K A57N S58G | L99T A100V | $8.23 \times 10^{-3}$ | 457.2 | $3.32 \times 10^{-4}$ | 2.08 |
| M48 | R28N | G50A L56T | E54K A57N S58L | L99T A100V | 0.0343 | 1905.6 | $8.42 \times 10^{-4}$ | 5.26 |
| M49 | R28N | G50A L56T | E54K A57N S58Y H61F | L99T A100V | 0.0148 | 822.2 | $5.95 \times 10^{-4}$ | 3.72 |
| M50 | R28N | G50A L56T | E54K A57R | L99T A100V | $5.30 \times 10^{-3}$ | 294.4 | $4.06 \times 10^{-4}$ | 2.54 |
| M51 | R28N | L56I | E54K A57G | L99T A100V | $1.18 \times 10^{-3}$ | 65.6 | $1.31 \times 10^{-4}$ | 0.82 |
| M52 | R28N | L56I | E54K A57N S58A | L99T A100V | $2.29 \times 10^{-3}$ | 127.2 | $2.81 \times 10^{-4}$ | 1.76 |
| M53 | R28N | L56I | E54K A57N S58G | L99T A100V | $1.91 \times 10^{-3}$ | 106.1 | $3.74 \times 10^{-4}$ | 2.34 |
| M54 | R28N T30A | G50A | E54K A57N S58P | L99T A100V | $2.16 \times 10^{-3}$ | 120.0 | $1.79 \times 10^{-3}$ | 11.19 |
| M55 | R28N T30A | L56S | E54K A57N S58E E64D | L99T A100V | $5.85 \times 10^{-3}$ | 325.0 | $4.78 \times 10^{-4}$ | 2.99 |
| M56 | R28N T30D | L56S | E54K A57N H61F | L99T A100V | $9.35 \times 10^{-3}$ | 519.4 | $4.79 \times 10^{-4}$ | 2.99 |
| M57 | R28N T30D | L56S | E54K A57N S58E | L99T A100V | $\underline{0.0104}$ | $\underline{1,200}$ | $\underline{3.22 \times 10^{-4}}$ | $\underline{3.08}$ |
| M58 | R28N T30D | L56S | E54K A57N S58I H61F | L99T A100V | No binding | n.d. | $1.95 \times 10^{-3}$ | 12.19 |
| M59 | R28N T30D | L56S | E54K A57N S58N H61F | L99T A100V | 0.0123 | 683.3 | $5.24 \times 10^{-4}$ | 3.28 |
| M60 | R28N T30D | L56S | E54K A57N S58R H61F | L99T A100V | 0.0272 | 1511.1 | $9.11 \times 10^{-4}$ | 5.69 |
| M61 | R28N T30G | A51H | E54Q A57N H61F | L99T A100V | $5.21 \times 10^{-3}$ | 289.4 | $4.59 \times 10^{-4}$ | 2.87 |
| M62 | R28N T30G | A51H L56T | E54K A57N S58E | L99T A100V | $\underline{5.75 \times 10^{-3}}$ | $\underline{242}$ | $\underline{5.57 \times 10^{-4}}$ | $\underline{5.86}$ |
| M63 | R28N T30G | G50A | E54K A57N S58T | L99T A100V | $2.65 \times 10^{-3}$ | 147.2 | $1.50 \times 10^{-3}$ | 9.38 |
| M64 | R28N T30G | G50A | E54K A57N S58V | L99T A100V | 0.0234 | 1300.0 | $1.32 \times 10^{-3}$ | 8.25 |
| M65 | R28N T30G | G50A L56I | E54K A57C | L99T A100V | $4.07 \times 10^{-3}$ | 226.1 | $8.03 \times 10^{-4}$ | 5.02 |

TABLE 6-continued

Amino acid sequences and binding affinity data for antibody G1 variants determined at 37° C. by Biacore.

| Clone | L1 | L2 | H2 | HC-FW3 | α-rat $k_{off}$(1/s) | α-rat $K_D$ (nM) | α-human $k_{off}$(1/s) | α-human $K_D$ (nM) |
|---|---|---|---|---|---|---|---|---|
| M66 | R28N T30G | L56I | E54K A57E | L99T A100V | $5.11 \times 10^{-3}$ | 283.9 | $5.20 \times 10^{-4}$ | 3.25 |
| M67 | R28N T30G | L56I | E54K A57F | L99T A100V | $1.71 \times 10^{-3}$ | 95.0 | $8.20 \times 10^{-4}$ | 5.13 |
| M68 | R28N T30G | L56I | E54K A57N S58D E64D | L99T A100V | $6.76 \times 10^{-3}$ | 375.6 | $4.28 \times 10^{-4}$ | 2.68 |
| M69 | R28N T30G | L56I | E54K A57N S58E | L99T A100V | $1.81 \times 10^{-3}$ | 100.6 | $7.33 \times 10^{-4}$ | 4.58 |
| M70 | R28N T30G | L56I | E54K A57S | L99T A100V | $6.07 \times 10^{-3}$ | 337.2 | $5.59 \times 10^{-4}$ | 3.49 |
| M71 | R28N T30G | L56I | E54K A57Y | L99T A100V | $2.12 \times 10^{-3}$ | 117.8 | $1.28 \times 10^{-3}$ | 8.00 |
| M72 | R28N T30G | L56S | E54K | L99T A100V | $3.95 \times 10^{-3}$ | 219.4 | $4.00 \times 10^{-4}$ | 2.50 |
| M73 | R28N T30G | L56S | E54K A57N S58Y E64D | L99T A100V | $3.00 \times 10^{-3}$ | 166.7 | $2.55 \times 10^{-4}$ | 1.59 |
| M74 | R28N T30G | L56S | E54K A57S | L99T A100V | $6.03 \times 10^{-3}$ | 335.0 | $5.97 \times 10^{-4}$ | 3.73 |
| M75 | R28N T30G | L56S | E54K A57V | L99T A100V | $1.87 \times 10^{-2}$ | 1038.9 | $1.16 \times 10^{-3}$ | 7.25 |
| M76 | R28N T30S | G50A L56T | A57G | L99T A100V | $1.16 \times 10^{-3}$ | 64.4 | $3.64 \times 10^{-4}$ | 2.28 |
| M77 | R28N T30S | G50A L56T | E54K A57D | L99T A100V | 0.0143 | 794.4 | $4.77 \times 10^{-4}$ | 2.98 |
| M78 | R28N T30S | G50A L56T | E54K A57N S58T | L99T A100V | 0.167 | 9277.8 | $1.31 \times 10^{-3}$ | 8.19 |
| M79 | R28N T30S | G50A L56T | E54K A57P | L99T A100V | 0.19 | 10555.6 | $1.29 \times 10^{-3}$ | 8.06 |
| M80 | R28N T30S | L56I | E54K A57N S58V | L99T A100V | 0.0993 | 5516.7 | $2.09 \times 10^{-3}$ | 13.06 |
| M81 | R28N T30S | L56S | E54K A57N S58E | L99T A100V | $4.29 \times 10^{-3}$ | 238.3 | $4.90 \times 10^{-4}$ | 3.06 |
| M82 | R28N T30V | A51H L56T | A57N | L99T A100V | $6.99 \times 10^{-3}$ | 388.3 | $8.77 \times 10^{-4}$ | 5.48 |
| M83 | R28N T30V | A51H L56T | E54K A57N S58M H61F | L99T A100V | No binding | n.d. | $9.33 \times 10^{-4}$ | 5.83 |
| M84 | R28N T30V | A51H L56T | E54N A57N | L99T A100V | $1.76 \times 10^{-2}$ | 977.8 | $1.08 \times 10^{-3}$ | 6.75 |

Figure 6:
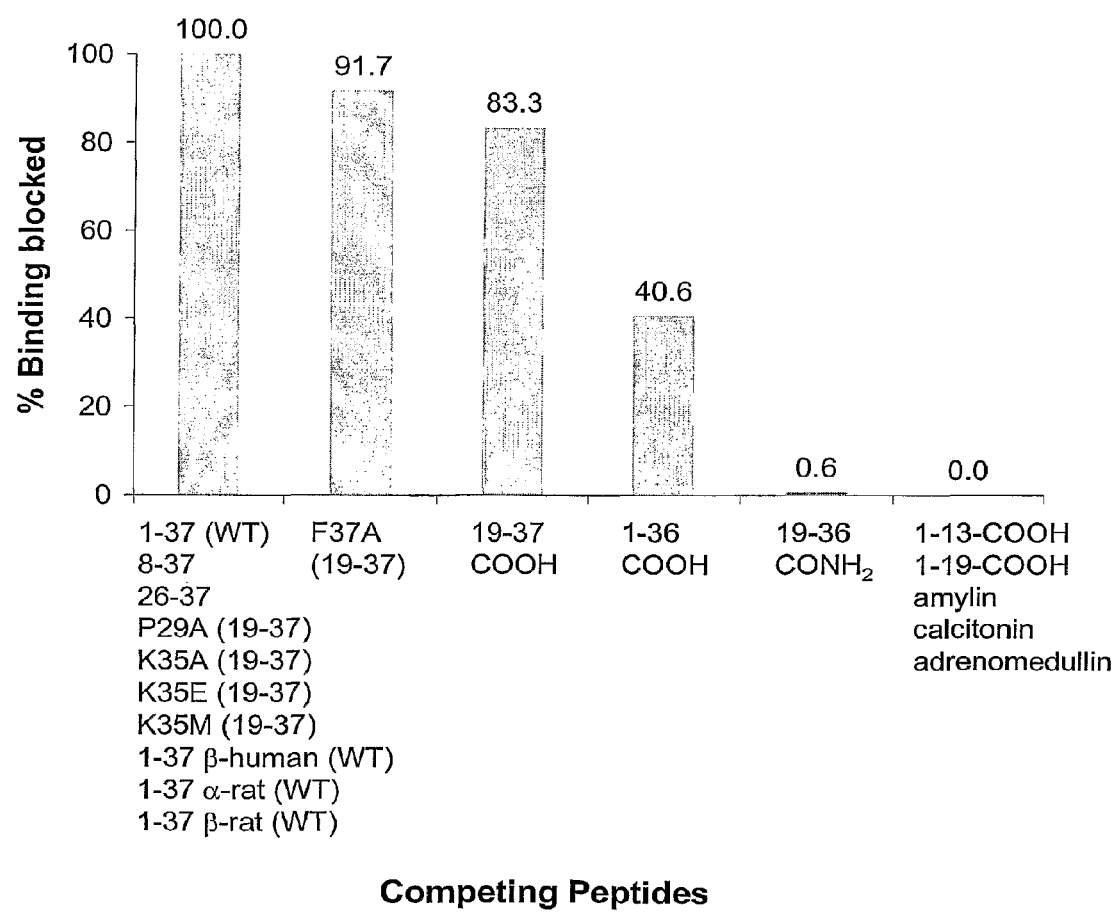
FIG. 6 shows epitope mapping of antibody G1 by peptide competition using Biacore. N-biotinylated human α-CGRP was captured on SA sensor chip. G1 Fab (50 nM) in the absence of a competing peptide or pre-incubated for 1 h with 10 uM of a competing peptide was flowed onto the chip. Binding of G1 Fab to the human α-CGRP on the chip was measured. Y axis represents percentage of binding blocked by the presence of the competing peptide compared with the binding in the absence of the competing peptide.

All CDRs including both Kabat and Chothia CDRs. Amino acid residues are numbered sequentially (see FIG. 5). All clones have L3 + H1 + H3 sequences identical to G1.
$K_D = k_{off}/k_{on}$. All $k_{off}$ values were determined in a screening mode except those that are underlined, which were obtained by global analysis of a Fab concentration series (G1 was analyzed in a high-resolution mode). Underlined $K_D$ values were therefore determined experimentally by measuring $k_{on}$. Other $k_{on}$ values were estimated to be the same as M25.
n.d. = not determined To determine the epitope on human α-CGRP that is recognized by antibody G1, Biacore assays described above were used. Human α-CGRP was purchased as an N-biotinylated version to enable its high-affinity capture via SA sensor chips. The binding of G1 Fab fragment to the human α-CGRP on the chip in the absence or presence of a CGRP peptide was determined. Typically, a 2000:1 mol peptide/Fab solution (e.g., 10 uM peptide in 50 nM G1 Fab) was injected across human α-CGRP on the chip. FIG. 6 shows the percentage of binding blocked by competing peptide. Data shown in FIG. 6 indicate that peptides that block 100% binding of G1 Fab to human α-CGRP are 1-37 (WT), 8-37, 26-37, P29A (19-37), K35A (19-37), K35E (19-37), and K35M (19-37) of human α-CGRP; 1-37 of β-CGRP (WT); 1-37 of rat α-CGRP (WT); and 1-37 of rat β-CGRP (WT). All these peptides are amidated at the C-terminus. Peptides F37A (19-37) and 19-37 (the latter not amidated at the C-terminus) of human α-CGRP also blocked about 80% to 90% of binding of G1 Fab to human α-CGRP. Peptide 1-36 (not amidated at the C-terminus) of human α-CGRP blocked about 40% of binding of G1 Fab to human α-CGRP. Peptide fragment 19-36 (amidated at the C-terminus) of human α-CGRP; peptide fragments 1-13 and 1-19 of human α-CGRP (neither of which are amidated at the C-terminus); and human amylin, calcitonin, and adrenomedullin (all amidated at the C-terminus) did not compete with binding of G1 Fab to human α-CGRP on the chip. These data demonstrate that G1 targets a C-terminal epitope of CGRP and that both the identity of the most terminal residue (F37) and its amidation is important for binding.

Binding affinities of G1 Fab to variants of human α-CGRP (at 37° C.) was also determined. Table 7 below shows the affinities as measured directly by titrating G1 Fab across N-biotinylated human α-CGRP and variants on the chip. Data in Table 7 indicate that antibody G1 binds to a C-terminal epitope with F37 and G33 being the most important residues. G1 does not bind to CGRP when an extra amino acid residue (alanine) is added at the C-terminal (which is amidated).

TABLE 7

Binding affinities of G1 Fab to human α-CGRP and variants measured at 37° C. (see Table 4 for their amino acid sequences)

| CGRP on chip | $k_{on}$ (1/Ms) | $k_{off}$ (1/s) | $K_D$ (nM) |
|---|---|---|---|
| 1-37 (WT) | $4.68 \times 10^5$ | $7.63 \times 10^{-5}$ | 0.16 (high resolution $K_D$ = 0.06) |
| 19-37 | $4.60 \times 10^5$ | $7.30 \times 10^{-5}$ | 0.16 |
| 25-37 | $3.10 \times 10^5$ | $8.80 \times 10^{-5}$ | 0.28 |
| F27A (25-37) | $3.25 \times 10^5$ | $1.24 \times 10^{-4}$ | 0.38 |
| V28A (25-37) | $3.32 \times 10^5$ | $9.38 \times 10^{-5}$ | 0.28 |
| P29A (25-37) | $2.26 \times 10^5$ | $1.78 \times 10^{-4}$ | 0.79 |
| T30A (25-37) | $1.79 \times 10^5$ | $8.41 \times 10^{-5}$ | 0.47 |
| N31A (25-37) | $2.17 \times 10^5$ | $1.14 \times 10^{-4}$ | 0.53 |
| V32A (25-37) | $2.02 \times 10^5$ | $3.46 \times 10^{-4}$ | 1.71 |
| G33A (25-37) | $2.07 \times 10^5$ | 0.0291 | 141 |
| S34A (25-37) | $2.51 \times 10^5$ | $7.64 \times 10^{-4}$ | 3.04 |
| K35A (19-37) | $2.23 \times 10^5$ | $2.97 \times 10^{-4}$ | 1.33 |
| K35E (19-37) | $5.95 \times 10^4$ | $5.79 \times 10^{-4}$ | 9.73 |
| K35M (19-37) | $2.63 \times 10^5$ | $1.34 \times 10^{-4}$ | 0.51 |
| K35Q (19-37) | $1.95 \times 10^5$ | $2.70 \times 10^{-4}$ | 1.38 |
| F37A (25-37) | $8.90 \times 10^4$ | $8.48 \times 10^{-3}$ | 95 (solution $K_D$ = 172 nM) |
| 38A (25-38A) | — | — | No binding detected |

The above data indicate that the epitope that antibody G1 binds is on the C-terminal end of human α-CGRP, and amino acids 33 and 37 on human α-CGRP are important for binding of antibody G1. Also, the amidation of residue F37 is important for binding.

Example 5: Effect of Anti-CGRP Antagonist Antibody G1 on Skin Vasodilatation Induced by Stimulation of Rat Saphenous Nerve To test antagonist activity of anti-CGRP antibody G1, effect of the antibody on skin vasodilatation by stimulation of rat saphenous nerve was tested using a rat model described in Example 3. Briefly, rats were maintained anesthesia with 2% isoflurane. Bretylium tosylate (30 mg/kg, administered i.v.) was given at the beginning of the experiment to minimize vasoconstriction due to the concomitant stimulation of sympathetic fibers of the saphenous nerve. Body temperature was maintained at 37° C. by the use of a rectal probe thermostatically connected to a temperature controlled heating blanket. The saphenous nerve of the right hindlimb was exposed surgically, cut proximally and covered with plastic wrap to prevent drying. A laser Doppler probe was placed over the medio-dorsal side of the hindpaw skin, which is the region innervated by the saphenous nerve. Skin blood flow, measured as blood cell flux, was monitored with a laser Doppler flow meter. In experiments to determine effects of antibody within two hours of injection thirty to forty five minutes after bretylium tosylate injection, when a stable base-line flux (less than 5% variation) was established for at least 5 min, the nerve was placed over platium bipolar electrodes and electrically stimulated (2 Hz, 10V, 1 ms, for 30 sec) and again 20 minutes later. The average of the blood flow flux response to these two stimulations was used to establish the baseline response (time 0) to electrical stimulation. Antibody G1 (1 mg/kg or 10 mg/kg) or vehicle (PBS with 0.01% Tween 20 equal volume to 10 mg/kg G1) were then administered intravenously (i.v.). The nerve was subsequently stimulated (2 Hz, 10V, 1 ms, for 30 sec) at 30 min, 60 min, 90 min, and 120 min after the antibody administration. Animals were kept under anesthesia for a period of approximately three hours. Cumulative change in skin blood flow was estimated by the area under the flux-time curve (AUC, which is equal to change in flux multiplied by change in time) for each flux response to electrical pulse stimulations.

Figure 7:
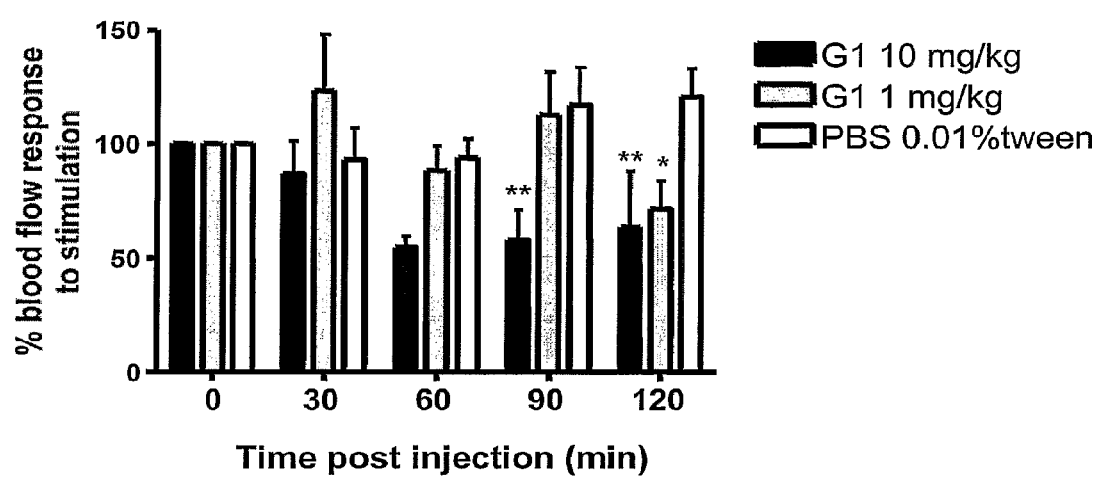
FIG. 7 shows the effect of administering antibody G1 (1 mg/kg or 10 mg/kg, i.v.) or vehicle (PBS, 0.01% Tween 20) on skin blood flow measured as blood cell flux after electrical pulse stimulation for 30 seconds. Antibody G1 or vehicle was administered intravenously (i.v.) followed by nerve electrical pulse stimulation at 30 min, 60 min, 90 min, and 120 min after antibody administration. Y axis represents percent of AUC as compared to level of AUC when no antibody or vehicle (defined as 100%) was administered (time 0). X axis represents time (minutes) period between the administration of antibodies and electrical pulse stimulation. "*" indicates P<0.05, and "**" indicates P<0.01, as compared to vehicle. Data were analyzed using two-way ANOVA and Bonferroni post tests.

As shown in FIG. 7, blood flow increase stimulated by applying electronic pulses on saphenous nerve was significantly inhibited by the presence of antibody G1 at 1 mg/kg (administered i.v.) as compared to the vehicle, when the saphenous nerve was electrically stimulated at 90 min after the antibody administration. Blood flow increase stimulated by applying electronic pulses on saphenous nerve was significantly inhibited by the presence of antibody G1 at 10 mg/kg (administered i.v.) as compared to the vehicle, when the saphenous nerve was electrically stimulated at 90 minutes and 120 minutes after antibody administration.

In experiments to determine effects of the antibodies at longer time points in the saphenous assay, rats were injected i.v. with the indicated doses of antibody 24 hours or 7 days prior to preparing the animal for saphenous nerve stimulation as described above. In these experiments it was impossible to establish a baseline response in individual rats to electrical pulse stimulation prior to dosing, so treated groups were compared to animals dosed with vehicle (PBS, 0.01% Tween 20) at 24 hours or 7 days.

Figure 8A:
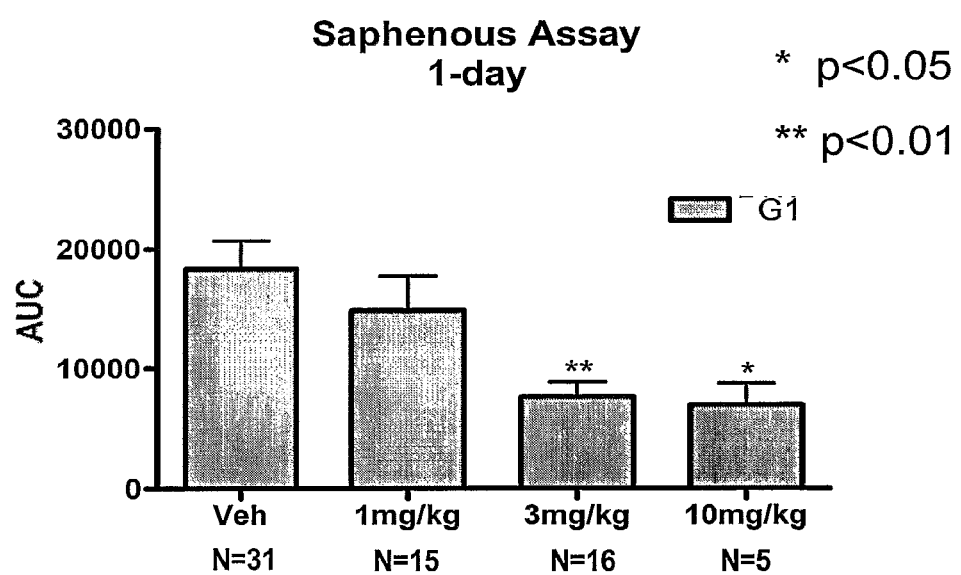
FIG. 8A shows the effect of administering antibody G1 (1 mg/kg, 3 mg/kg or 10 mg/kg, i.v.) or vehicle (PBS, 0.01% Tween 20) on skin blood flow measured as blood cell flux after electrical pulse stimulation for 30 seconds 24 hours after dosing. Antibody G1 or vehicle was administered intravenously (i.v.) 24 hours before nerve electrical pulse stimulation. Y axis represents total area under curve (change in blood cell flux multiplied by the change in time from stimulation until flux returns to baseline, AUC). X axis represents varying doses of antibody G1. "*" indicates P<0.05, and "**" indicates P<0.01, as compared to vehicle. Data were analyzed using one-way ANOVA and Dunn's multiple comparison test.
Figure 8B:
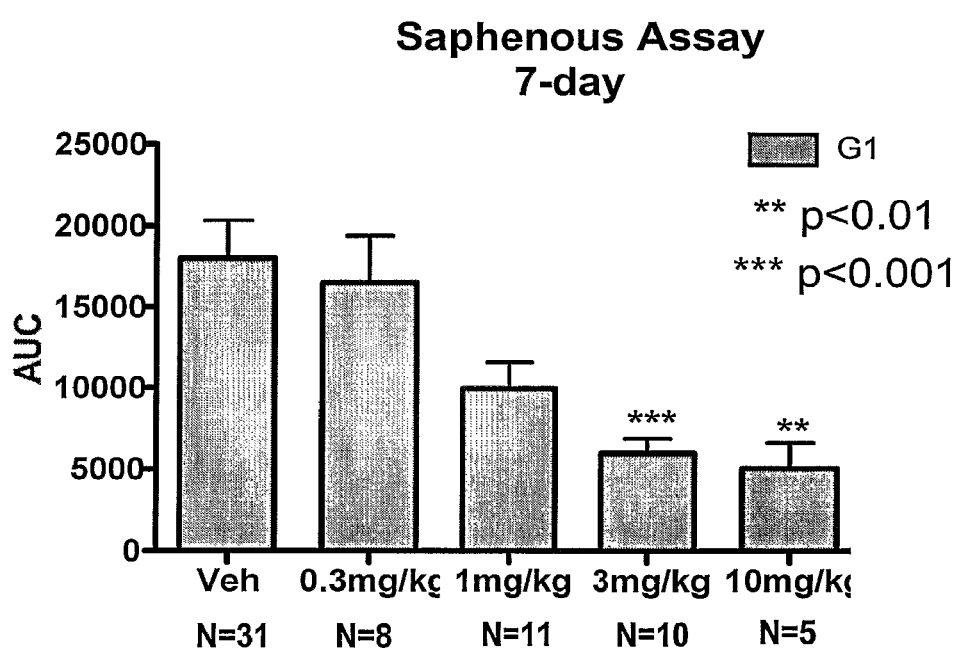
FIG. 8B shows the effect of administering antibody G1 (0.3 mg/kg, 1 mg/kg, 3 mg/kg or 10 mg/kg, i.v.) or vehicle (PBS, 0.01% Tween 20) on skin blood flow measured as blood cell flux after electrical pulse stimulation for 30 seconds 7 days after dosing. Antibody G1 or vehicle was administered intravenously (i.v.) 7 days before nerve electrical pulse stimulation. Y axis represents total AUC. X axis represents varying doses of antibody G1. "" indicates $P<0.01$, and "*" indicates $P<0.001$, as compared to vehicle. Data were analyzed using one-way ANOVA and Dunn's multiple comparison test.

As shown in FIGS. 8A and 8B blood flow increases in the dorso-medial hindpaw skin evoked by saphenous nerve stimulation were significantly inhibited in the groups of animals dosed with either 10 mg/kg or 3 mg/kg G1 at either 24 hours or 7 days prior to stimulation as compared to vehicle groups dosed at the same time points.

Figure 8C:
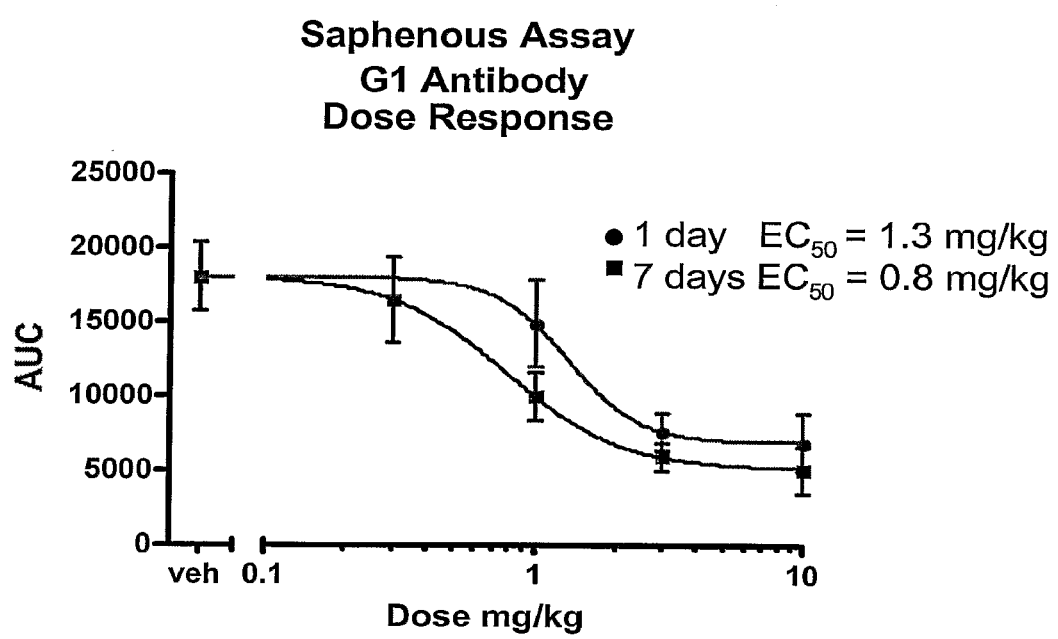
FIG. 8C is a curve fit analysis of the data from FIGS. 8A and 8B. Antibody G1 or vehicle was administered intravenously (i.v.) either 24 hours or 7 days before nerve electrical pulse stimulation. Y axis represents total AUC. X axis represents varying doses of antibody G1 in "mg/kg" on a logarithmic scale to determine $EC_{50}$.

FIG. 8C represents a curve fit analysis applied to the dose response data represented in FIGS. 8A and 8B to determine the dose required for 50% maximal effect ($EC_{50}$). The $EC_{50}$ at 24 hours is 1.3 mg/kg and the $EC_{50}$ at 7 days is slightly lower (0.8 mg/kg).

Example 6: Acute Effect of Anti-CGRP Antagonist Antibody G1 in a Dural Artery (Closed Cranial Window) Assay Closed Cranial Window Model: The purpose of this experiment was to determine the acute effect of anti-CGRP antagonist antibodies and compare it with the acute effect of the CGRP receptor antagonist BIBN4096BS. Experiments were carried out as previously described (Williamson et al., Cephalalgia 17(4):518-24 (1997)) with the following modifications. Sprague Dawley rats (300-400 g) were anesthetized with 70 mg/kg i.p. pentobarbital. Anesthesia was maintained with 20 mg/kg/hr i.v. pentobarbital. Rats were cannulated through the jugular vein for delivery of all drugs. Blood pressure was monitored with a probe (mikro-tip catheter, Millar Instruments) threaded through the femoral artery into the abdominal aorta. The rats were tracheotomized and breathing rate was maintained at 75 breaths per minute at a volume of 3.5 mL. After fixating the head in a stereotactic instrument and removing the scalp, a 2×6 mm window in the left parietal area just lateral to the sagittal suture was made by thinning the bone with a dental drill. Using a micromanipulator, a platinum bipolar electrode was lowered onto the surface and covered with heavy mineral oil. Lateral to the electrode window another window of 5×6 mm was created and filled with heavy mineral oil through which the diameter of a branch of the middle meningeal artery (MMA) was continuously monitored with a CCD camera and a video dimension analyzer (Living Systems). The rats were rested for no less than 45 minutes after the preparation. A baseline response to electrical stimulation was established (15 V, 10 hz, 0.5 ms pulses, 30 seconds) and then rats were dosed i.v. with experimental compound (10 mg/kg mu7E9, 300 µl/kg BIBN4096BS or PBS 0.01% Tween 20). Additional electrical stimulations were done at 5 (BIBN4096BS), 30, 60, 90 and 120 minutes after dosing. All data was recorded using chart software (ADInstruments).

Figure 9:
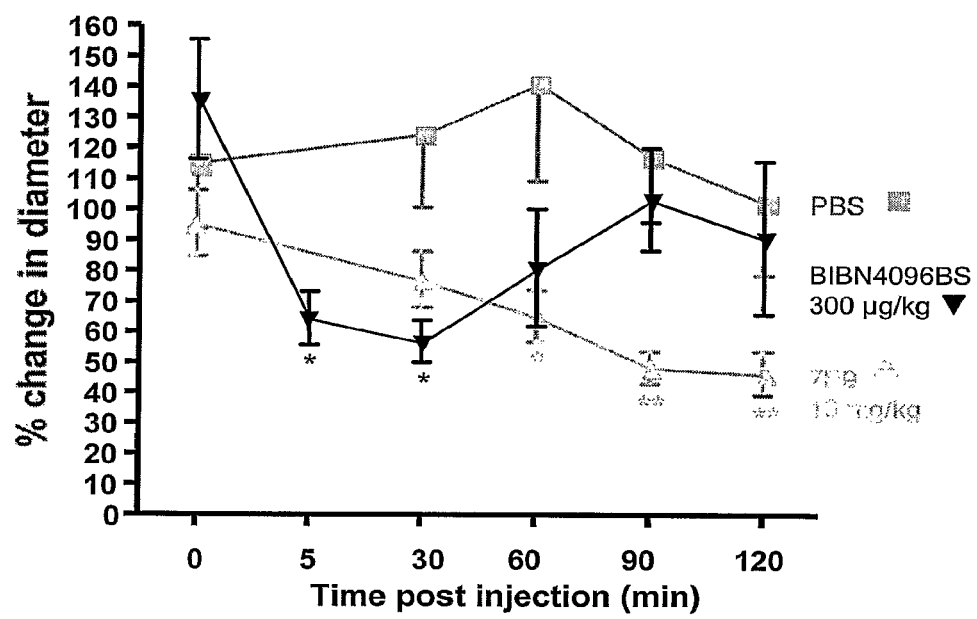
FIG. 9 shows the effect of antibody mu7E9 (10 mg/kg), BIBN4096BS or vehicle (PBS, 0.01% Tween 20) on the change in diameter of the middle meningeal artery after electrical field stimulation. Antibody mu7E9, BIBN4096BS or vehicle were administered intravenously (i.v.) at time point 0 minutes after a baseline response to electrical stimulation was established. Y axis represents change in diameter of the middle meningeal artery after electrical field stimulation. Resting diameter corresponds to 0%. X axis represents time (minutes) of electrical pulse stimulation. "*" indicates $P<0.05$, and "**" indicates $P<0.01$, as compared to vehicle. Data were analyzed using one-way ANOVA and Dunett's multiple comparison test.

As shown in FIG. 9 mu7E9 at 10 mg/kg significantly blocks MMA dilation evoked by electrical field stimulation within 60 minutes after dosing and maintains the effect throughout the duration of the assay (120 minutes). For comparison BIBN4096BS blocks MMA dilation within 5 minutes of dosing but the effect has completely disappeared by 90 minutes. The magnitude of the block is comparable between BIBN4096BS and mu7E9.

Example 7: Chronic Effect of Anti-CGRP Antagonist Antibody G1 in a Dural Artery (Closed Cranial Window) Assay The purpose of this experiment was to determine if the anti CGRP antibody could still block electrically stimulated MMA dilation 7 days after dosing. Preparation of the rats was identical to the above described acute experiment (Example 6) with the following exceptions. Rats were injected i.v. (10 mg/kg, 3 mg/kg or 1 mg/kg G1) 7 days prior to creating the closed cranial window prep and stimulation. It was impossible to establish a baseline dilation response to electrical stimulation prior to dosing as in the acute experiment so the antibody groups were compared to dilation of the MMA in a vehicle (PBS, 0.01% Tween 20) dosed control group. After the rats were allowed to rest for no less than 45 minutes the dura was electrically stimulated at 30 minute intervals. Stimulations were at 2.5V, 5V, 10V, 15V and 20V, all at 10 hz, 0.5 ms pulses for 30 seconds.

Figure 10:
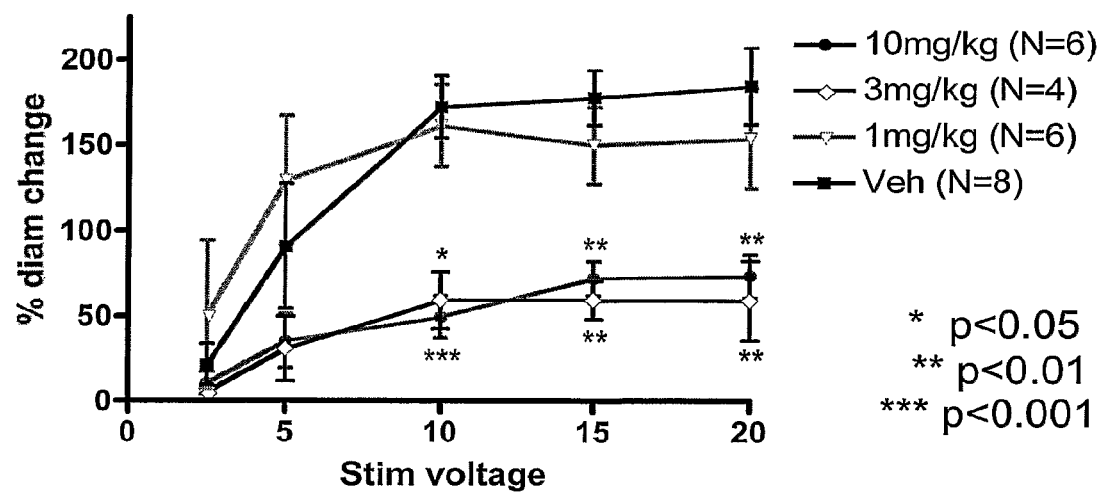
FIG. 10 shows the effect of varying doses of antibody G1 (1 mg/kg, 3 mg/kg or 10 mg/kg, i.v.) or vehicle (PBS, 0.01% Tween 20) on the change in diameter of the middle meningeal artery after electrical field stimulation. Antibody G1 or vehicle was administered intravenously (i.v.) 7 days before electrical field stimulation. Y axis represents change in diameter of the middle meningeal artery. Resting diameter corresponds to 0%. X axis represents stimulation voltage. "*" indicates $P<0.05$, "" indicates $P<0.01$, and "*" indicates $P<0.001$, as compared to vehicle. Data were analyzed using two-way ANOVA and Bonferroni posttests.

As shown in FIG. 10 G1 at 10 mg/kg and 3 mg/kg significantly blocked MMA dilation evoked by electrical stimulation in the range of 10 to 20 volts. This data demonstrates that G1 can block electrically stimulated MMA dilation up to 7 days after dosing.

Example 8: Morphine Withdrawal Hot Flush Model

The morphine withdrawal rat model is an established rodent model for menopausal hot flush mechanisms (Sipe et al., Brain Res. 1028(2):191-202 (2004); Merchenthaler et al., Maturitas 30:307-316 (1998); Katovich et al., Brain Res. 494:85-94 (1989); Simpkins et al., Life Sciences 32:1957-1966 (1983)). Basically the rats are addicted to morphine by implanting morphine pellets under the skin. Upon addiction the animals are injected with naloxone (opioid antagonist) which sends them into withdrawal immediately. This withdrawal is accompanied by a skin temperature increase, a core body temperature decrease, an increase in heart rate and an increase in serum luteinizing hormone. These are all similar in magnitude and timing to what occurs in human hot flush (Simpkins et al., Life Sciences 32:1957-1966 (1983)). Furthermore, if rats are treated with estradiol prior to inducing withdrawal, the symptoms of hot flush are reduced (Merchenthaler et al., Maturitas 30:307-316 (1998)). This is why the morphine withdrawal model is believed to mimic clinical hot flush.

Figure 11A:
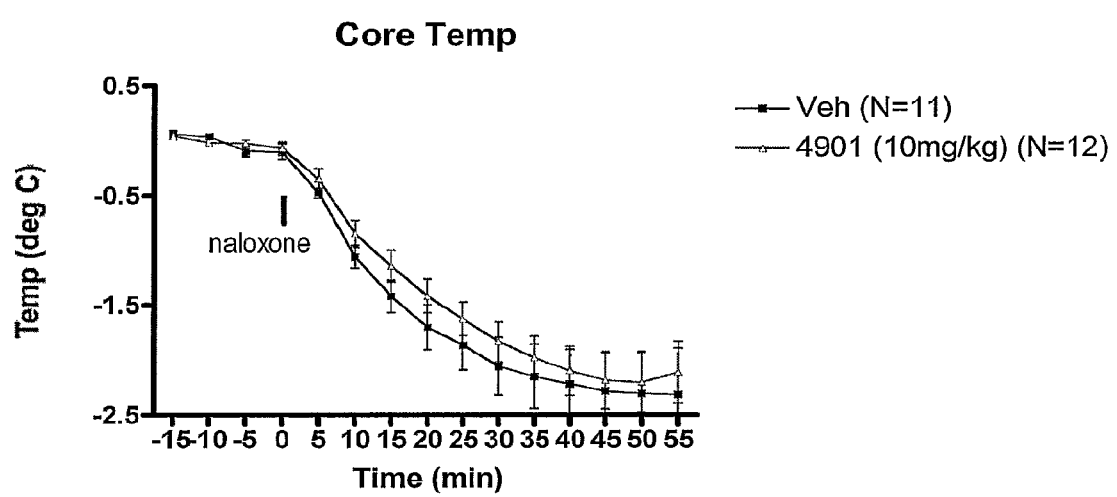
FIG. 11A shows the effect of antibody mu4901 (10 mg/kg) or vehicle (PBS, 0.01% Tween 20), administered intravenously (i.v.) 24 hours prior, on the decrease in core temperature induced by subcutaneous injection of naloxone (1 mg/kg) in morphine addicted rats. The Y axis represents temperature difference from baseline. The X axis represents time measured from the point of naloxone injection.
Figure 11B:
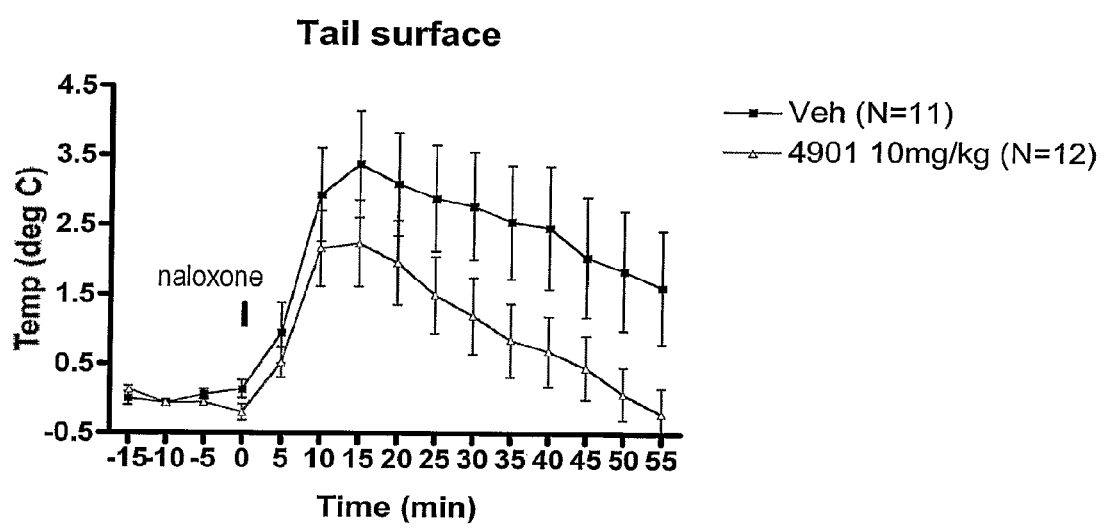
FIG. 11B shows the effect of antibody mu4901 (10 mg/kg) or vehicle (PBS, 0.01% Tween 20), administered intravenously (i.v.) 24 hours prior, on the increase in tail surface temperature induced by subcutaneous injection of naloxone (1 mg/kg) in morphine addicted rats. The Y axis represents temperature difference from baseline. The X axis represents time measured from the point of naloxone injection.

Ovariectomized rats were ordered from Charles River Laboratories. Not less than 7 days post ovariectomy morphine dependency was created by implanting a morphine pellet (75 mg morphine base) subcutaneously. Two days later 2 more pellets were implanted. The following day rats were injected intravenously with either 10 mg/kg 4901 [**] or vehicle (PBS, 0.01% tween). Two days after the second pelleting the rats were anesthetized with ketamine (90 mg/kg) and lightly restrained. A surface temperature thermocouple was taped to the base of the tail and a rectal thermocouple is used to measure core temperature. Data was recorded using Chart software (ADInstruments). After recording 15 minutes of stable baseline temperature, naloxone (1 mg/kg) was injected subcutaneously. Temperature was recorded continuously for the next 60 minutes. The results are shown in FIGS. 11A and 11B.

It is understood that the examples and embodiments described herein are for illustrative purposes only and that various modifications or changes in light thereof will be suggested to persons skilled in the art and are to be included within the spirit and purview of this application. All publications, patents and patent applications cited herein are hereby incorporated by reference in their entirety for all purposes to the same extent as if each individual publication, patent or patent application were specifically and individually indicated to be so incorporated by reference.

Deposit of Biological Material

The following materials have been deposited with the American Type Culture Collection, 10801 University Boulevard, Manassas, Va. 20110-2209, USA (ATCC):

| Material | Antibody No. | ATCC Accession No. | Date of Deposit |
| --- | --- | --- | --- |
| pDb.CGRP.hFcGI | G1 heavy chain | PTA-6867 | Jul. 15, 2005 |
| pEb.CGRP.hKGI | G1 light chain | PTA-6866 | Jul. 15, 2005 |

Vector pEb.CGRP.hKGI is a polynucleotide encoding the G1 light chain variable region and the light chain kappa constant region; and vector pDb.CGRP.hFcGI is a polynucleotide encoding the G1 heavy chain variable region and the heavy chain IgG2 constant region containing the following mutations: A330P331 to S330S331 (amino acid numbering with reference to the wildtype IgG2 sequence; see Eur. J. Immunol. (1999) 29:2613-2624).

These deposits were made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposit will be made available by ATCC under the terms of the Budapest Treaty, and subject to an agreement between Rinat Neuroscience Corp. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC Section 122 and the Commissioners rules pursuant thereto (including 37 CFR Section 1.14 with particular reference to 886 OG 638).

The assignee of the present application has agreed that if a culture of the materials on deposit should die or be lost or destroyed when cultivated under suitable conditions, the materials will be promptly replaced on notification with

| Antibody sequences |
| --- |
| G1 heavy chain variable region amino acid sequence (SEQ ID NO: 1) |

EVQLVESGGGLVQPGGSLRLSCAASGFTFSNYWISWVRQAPGKGLEWVAEIRSESDASATHYAEAVKGRFTI

SRDNAKNSLYLQMNSLRAEDTAVYYCLAYFDYGLAIQNYWGQGTLVTVSS

| G1 light chain variable region amino acid sequence (SEQ ID NO: 2) |
| --- |

EIVLTQSPATLSLSPGERATLSCKASKRVTTYVSWYQQKPGQAPRLLIYGASNRYLGIPARFSGSGSGTDFTL

TISSLEPEDFAVYYCSQSYNYPYTFGQGTKLEIK

| G1 CDR H1 (extended CDR) (SEQ ID NO: 3) |
| --- |

GFTFSNYWIS

| G1 CDR H2 (extended CDR) (SEQ ID NO: 4) |
| --- |

EIRSESDASATHYAEAVKG

| G1 CDR H3 (SEQ ID NO: 5) |
| --- |

YFDYGLAIQNY

| G1 CDR L1 (SEQ ID NO: 6) |
| --- |

KASKRVTTYVS

| G1 CDR L2 (SEQ ID NO: 7) |
| --- |

GASNRYL

| G1 CDR L3 (SEQ ID NO: 8) |
| --- |

SQSYNYPYT

| G1 heavy chain variable region nucleotide sequence (SEQ ID NO: 9) |
| --- |

GAAGTTCAGCTGGTTGAATCCGGTGGTGGTCTGGTTCAGCCAGGTGGTTCCCTGCGTCTGTCCTGCGCT

GCTTCCGGTTTCACCTTCTCCAACTACTGGATCTCCTGGGTTCGTCAGGCTCCTGGTAAAGGTCTGGAAT

GGGTTGCTGAAATCCGTTCCGAATCCGACGCGTCCGCTACCCATTACGCTGAAGCTGTTAAAGGTCGTTT

CACCATCTCCCGTGACAACGCTAAGAACTCCCTGTACCTGCAGATGAACTCCCTGCGTGCTGAAGACAC

CGCTGTTTACTACTGCCTGGCTTACTTTGACTACGGTCTGGCTATCCAGAACTACTGGGGTCAGGGTACC

CTGGTTACCGTTTCCTCC

| G1 light chain variable region nucleotide sequence (SEQ ID NO: 10) |
| --- |

GAAATCGTTCTGACCCAGTCCCCGGCTACCCTGTCCCTGTCCCCAGGTGAACGTGCTACCCTGTCCTGCAAA

GCTTCCAAACGGGTTACCACCTACGTTTCCTGGTACCAGCAGAAACCCGGTCAGGCTCCTCGTCTGCTGATC

TACGGTGCTTCCAACCGTTACCTCGGTATCCCAGCTCGTTTCTCCGGTTCCGGTTCCGGTACCGACTTCACC

CTGACCATCTCCTCCCTGGAACCCGAAGACTTCGCTGTTTACTACTGCAGTCAGTCCTACAACTACCCCTACA

CCTTCGGTCAGGGTACCAAACTGGAAATCAAA

| G1 heavy chain full antibody amino acid sequence (including modified IgG2 as described herein)(SEQ ID NO: 11) |
| --- |

EVQLVESGGGLVQPGGSLRLSCAASGFTFSNYWISWVRQAPGKGLEWVAEIRSESDASATHYAEAVKGRFTI

SRDNAKNSLYLQMNSLRAEDTAVYYCLAYFDYGLAIQNYWGQGTLVTVSSASTKGPSVFPLAPCSRSTSEST

AALGCLVKDYFPEPVTVSWNSGALTSGVHTFPAVLQSSGLYSLSSVVTVPSSNFGTQTYTCNVDHKPSNTKV

DKTVERKCCVECPPCPAPPVAGPSVFLFPPKPKDTLMISRTPEVTCVVVDVSHEDPEVQFNWYVDGVEVHNA

KTKPREEQFNSTFRVVSVLTVVHQDWLNGKEYKCKVSNKGLPSSIEKTISKTKGQPREPQVYTLPPSREEMTK

NQVSLTCLVKGFYPSDIAVEWESNGQPENNYKTTPPMLDSDGSFFLYSKLTVDKSRWQQGNVFSCSVMHEA

LHNHYTQKSLSLSPGK

G1 light chain full antibody amino acid sequence (SEQ ID NO: 12)

EIVLTQSPATLSLSPGERATLSCKASKRVTTYVSWYQQKPGQAPRLLIYGASNRYLGIPARFSGSGSGTDFTL

TISSLEPEDFAVYYCSQSYNYPYTFGQGTKLEIKRTVAAPSVFIFPPSDEQLKSGTASVVCLLNNFYPREAKV

QWKVDNALQSGNSQESVTEQDSKDSTYSLSSTLTLSKADYEKHKVYACEVTHQGLSSPVTKSFNRGEC

G1 heavy chain full antibody nucleotide sequence (including
modified IgG2 as described herein)(SEQ ID NO: 13)

GAAGTTCAGCTGGTTGAATCCGGTGGTGGTCTGGTTCAGCCAGGTGGTTCCCTGCGTCTGTCCTGCGCT

GCTTCCGGTTTCACCTTCTCCAACTACTGGATCTCCTGGGTTCGTCAGGCTCCTGGTAAAGGTCTGGAAT

GGGTTGCTGAAATCCGTTCCGAATCCGACGCGTCCGCTACCCATTACGCTGAAGCTGTTAAAGGTCGTTT

CACCATCTCCCGTGACAACGCTAAGAACTCCCTGTACCTGCAGATGAACTCCCTGCGTGCTGAAGACAC

CGCTGTTTACTACTGCCTGGCTTACTTTGACTACGGTCTGGCTATCCAGAACTACTGGGGTCAGGGTACC

CTGGTTACCGTTTCCTCCGCCTCCACCAAGGGCCCATCTGTCTTCCCACTGGCCCCATGCTCCCGCAGC

ACCTCCGAGAGCACAGCCGCCCTGGGCTGCCTGGTCAAGGACTACTTCCCAGAACCTGTGACCGTGTC

CTGGAACTCTGGCGCTCTGACCAGCGGCGTGCACACCTTCCCAGCTGTCCTGCAGTCCTCAGGTCTCTA

CTCCCTCAGCAGCGTGGTGACCGTGCCATCCAGCAACTTCGGCACCCAGACCTACACCTGCAACGTAGA

TCACAAGCCAAGCAACACCAAGGTCGACAAGACCGTGGAGAGAAAGTGTTGTGTGGAGTGTCCACCTTG

TCCAGCCCCTCCAGTGGCCGGACCATCCGTGTTCCTGTTCCCTCCAAAGCCAAAGGACACCCTGATGAT

CTCCAGAACCCCAGAGGTGACCTGTGTGGTGGTGGACGTGTCCCACGAGGACCCAGAGGTGCAGTTCA

ACTGGTATGTGGACGGAGTGGAGGTGCACAACGCCAAGACCAAGCCAAGAGAGGAGCAGTTCAACTCC

ACCTTCAGAGTGGTGAGCGTGCTGACCGTGGTGCACCAGGACTGGCTGAACGGAAAGGAGTATAAGTG

TAAGGTGTCCAACAAGGGACTGCCATCCAGCATCGAGAAGACCATCTCCAAGACCAAGGGACAGCCAAG

AGAGCCACAGGTGTATACCCTGCCCCCATCCAGAGAGGAGATGACCAAGAACCAGGTGTCCCTGACCTG

TCTGGTGAAGGGATTCTATCCATCCGACATCGCCGTGGAGTGGGAGTCCAACGGACAGCCAGAGAACAA

CTATAAGACCACCCCTCCAATGCTGGACTCCGACGGATCCTTCTTCCTGTATTCCAAGCTGACCGTGGAC

AAGTCCAGATGGCAGCAGGGAAACGTGTTCTCTTGTTCCGTGATGCACGAGGCCCTGCACAACCACTAT

ACCCAGAAGAGCCTGTCCCTGTCTCCAGGAAAGTAA

G1 light chain full antibody nucleotide sequence (SEQ ID NO: 14)

GAAATCGTTCTGACCCAGTCCCCGGCTACCCTGTCCCTGTCCCCAGGTGAACGTGCTACCCTGTCCTGC

AAAGCTTCCAAACGGGTTACCACCTACGTTTCCTGGTACCAGCAGAAACCCGGTCAGGCTCCTCGTCTG

CTGATCTACGGTGCTTCCAACCGTTACCTCGGTATCCCAGCTCGTTTCTCCGGTTCCGGTTCCGGTACC

GACTTCACCCTGACCATCTCCTCCCTGGAACCCGAAGACTTCGCTGTTTACTACTGCAGTCAGTCCTACA

ACTACCCCTACACCTTCGGTCAGGGTACCAAACTGGAAATCAAACGCACTGTGGCTGCACCATCTGTCTT

CATCTTCCCTCCATCTGATGAGCAGTTGAAATCCGGAACTGCCTCTGTTGTGTGCCTGCTGAATAACTTC

TATCCGCGCGAGGCCAAAGTACAGTGGAAGGTGGATAACGCCCTCCAATCCGGTAACTCCCAGGAGAG

TGTCACAGAGCAGGACAGCAAGGACAGCACCTACAGCCTCAGCAGCACCCTGACCCTGAGCAAAGCAG

ACTACGAGAAACACAAAGTCTACGCCTGCGAAGTCACCCATCAGGGCCTGAGTTCTCCAGTCACAAAGA

GCTTCAACCGCGGTGAGTGCTAA

-continued

Amino acid sequence comparison of human and rat CGRP (human α-CGRP (SEQ ID NO: 15); human β-CGRP (SEQ ID NO: 43); rat α-CGRP (SEQ ID NO: 41); and rat β-CGRP (SEQ ID NO: 44)):

NH$_2$-ACDTATCVTHRLAGLLSRSGGVVKNNFVPTNVGSKAF-CONH$_2$ (human α-CGRP)

NH$_2$-ACNTATCVTHRLAGLLSRSGGMVKSNFVPTNVGSKAF-CONH$_2$ (human β-CGRP)

NH$_2$-SCNTATCVTHRLAGLLSRSGGVVKDNFVPTNVGSEAF-CONH$_2$ (rat α-CGRP)

NH$_2$-SCNTATCVTHRLAGLLSRSGGVVKDNFVPTNVGSKAF-CONH$_2$ (rat β-CGRP)

---

We claim:

1. A humanized monoclonal anti-Calcitonin Gene-Related Peptide (CGRP) antagonist antibody, comprising:
   two human IgG heavy chains, each heavy chain comprising three complementarity determining regions (CDRs) and four framework regions, wherein portions of the two heavy chains together form an Fc region; and
   two light chains, each light chain comprising three CDRs and four framework regions;
   wherein the CDRs impart to the antibody specific binding to a CGRP consisting of amino acid residues 1 to 37 of SEQ ID NO:15 or SEQ ID NO: 43.

2. The antibody of claim 1, wherein constant regions of the IgG heavy chains are IgG1 constant regions.

3. The antibody of claim 2, wherein the CDRs impart to the antibody specific binding to a fragment of the CGRP comprising amino acid residues 8 to 37 of SEQ ID NO:15.

4. The antibody of claim 2, wherein the CDRs of the humanized monoclonal antibody are derived from mouse, rat, or rabbit CDRs.

5. The antibody of claim 2, wherein a constant region of at least one IgG heavy chain comprises a mutation in an oligosaccharide attachment amino acid residue that is part of an N-glycosylation recognition sequence in the constant region.

6. The antibody of claim 1, wherein the IgG constant regions are IgG2 constant regions.

7. The antibody of claim 6, wherein the CDRs impart to the antibody specific binding to a fragment of the CGRP comprising amino acid residues 8 to 37 of SEQ ID NO:15.

8. The antibody of claim 6, wherein the CDRs impart to the antibody specific binding to a fragment of the CGRP comprising amino acid residues 33 to 37 of SEQ ID NO:15.

9. The antibody of claim 6, wherein the CDRs of the humanized monoclonal antibody are derived from mouse, rat, or rabbit CDRs.

10. The antibody of claim 6, wherein a constant region of at least one IgG heavy chain comprises a mutation in an oligosaccharide attachment amino acid residue that is part of an N-glycosylation recognition sequence in the constant region.

11. The antibody of claim 1, wherein constant regions of the IgG heavy chains are IgG4 constant regions.

12. The antibody of claim 11, wherein the CDRs impart to the antibody specific binding to a fragment of the CGRP comprising amino acid residues 8 to 37 of SEQ ID NO:15.

13. The antibody of claim 11, wherein the CDRs of the humanized monoclonal antibody are derived from mouse, rat, or rabbit CDRs.

14. The antibody of claim 11, wherein a constant region of the antibody comprises a mutation in an oligosaccharide attachment amino acid residue that is part of an N-glycosylation recognition sequence in the constant region.

15. The antibody of claim 14, wherein the antibody is aglycosylated at the mutation position.

* * * * *

(12) INTER PARTES REVIEW CERTIFICATE (2644th)
United States Patent
Zeller et al.

(10) Number: US 9,890,210 K1
(45) Certificate Issued: Mar. 4, 2022

(54) ANTAGONIST ANTIBODIES DIRECTED AGAINST CALCITONIN GENE- RELATED PEPTIDE

(71) Applicants: Joerg Zeller; Kristian T. Poulsen; Yasmina Noubia Abdiche; Jaume Pons; Sierra Jones Collier; Arnon Rosenthal

(72) Inventors: Joerg Zeller; Kristian T. Poulsen; Yasmina Noubia Abdiche; Jaume Pons; Sierra Jones Collier; Arnon Rosenthal

(73) Assignee: TEVA PHARMACEUTICALS INTERNATIONAL GMBH

Trial Number:

IPR2018-01425 filed Aug. 8, 2018

Inter Partes Review Certificate for:

Patent No.: 9,890,210
Issued: Feb. 13, 2018
Appl. No.: 15/588,432
Filed: May 5, 2017

The results of IPR2018-01425 are reflected in this inter partes review certificate under 35 U.S.C. 318(b).

INTER PARTES REVIEW CERTIFICATE
U.S. Patent 9,890,210 K1
Trial No. IPR2018-01425
Certificate Issued Mar. 4, 2022

AS A RESULT OF THE INTER PARTES REVIEW PROCEEDING, IT HAS BEEN DETERMINED THAT:

Claims 1-15 are cancelled.

\* \* \* \* \*

SEQUENCE LISTING

<160> NUMBER OF SEQ ID NOS: 57

<210> SEQ ID NO 1
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Ile Ser Trp Val Arg Gln Ala Pro Gly Lys Gly Leu Glu Trp Val
        35                  40                  45

Ala Glu Ile Arg Ser Glu Ser Asp Ala Ser Ala Thr His Tyr Ala Glu
    50                  55                  60

Ala Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Leu Ala Tyr Phe Asp Tyr Gly Leu Ala Ile Gln Asn Tyr Trp
            100                 105                 110

Gly Gln Gly Thr Leu Val Thr Val Ser Ser
        115                 120

<210> SEQ ID NO 2
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Ile Val Leu Thr Gln Ser Pro Ala Thr Leu Ser Leu Ser Pro Gly
1               5                   10                  15

Glu Arg Ala Thr Leu Ser Cys Lys Ala Ser Lys Arg Val Thr Thr Tyr
            20                  25                  30

Val Ser Trp Tyr Gln Gln Lys Pro Gly Gln Ala Pro Arg Leu Leu Ile
        35                  40                  45

Tyr Gly Ala Ser Asn Arg Tyr Leu Gly Ile Pro Ala Arg Phe Ser Gly
    50                  55                  60

Ser Gly Ser Gly Thr Asp Phe Thr Leu Thr Ile Ser Ser Leu Glu Pro

```
                65                  70                  75                  80
Glu Asp Phe Ala Val Tyr Tyr Cys Ser Gln Ser Tyr Asn Tyr Pro Tyr
                    85                  90                  95

Thr Phe Gly Gln Gly Thr Lys Leu Glu Ile Lys
            100                 105

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Phe Thr Phe Ser Asn Tyr Trp Ile Ser
1               5                   10

<210> SEQ ID NO 4
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Glu Ile Arg Ser Glu Ser Asp Ala Ser Ala Thr His Tyr Ala Glu Ala
1               5                   10                  15

Val Lys Gly

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Phe Asp Tyr Gly Leu Ala Ile Gln Asn Tyr
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Lys Ala Ser Lys Arg Val Thr Thr Tyr Val Ser
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Ala Ser Asn Arg Tyr Leu
1               5
```

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ser Gln Ser Tyr Asn Tyr Pro Tyr Thr
1               5

<210> SEQ ID NO 9
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
gaagttcagc tggttgaatc cggtggtggt ctggttcagc caggtggttc cctgcgtctg      60
tcctgcgctg cttccggttt caccttctcc aactactgga tctcctgggt tcgtcaggct     120
cctggtaaag gtctggaatg ggttgctgaa atccgttccg aatccgacgc gtccgctacc     180
cattacgctg aagctgttaa aggtcgtttc accatctccc gtgacaacgc taagaactcc     240
ctgtacctgc agatgaactc cctgcgtgct gaagacaccg ctgttttacta ctgcctggct     300 tactttgact acggtctggc tatccagaac tactggggtc agggtaccct ggttaccgtt     360
tcctcc                                                                366

<210> SEQ ID NO 10
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
gaaatcgttc tgacccagtc cccggctacc ctgtccctgt ccccaggtga acgtgctacc      60
ctgtcctgca agcttccaa acgggttacc acctacgttt cctggtacca gcagaaaccc     120
ggtcaggctc ctcgtctgct gatctacggt gcttccaacc gttacctcgg tatcccagct     180
cgtttctccg gttccggttc cggtaccgac ttcaccctga ccatctcctc cctggaaccc     240
gaagacttcg ctgttttacta ctgcagtcag tcctacaact accctacac cttcggtcag     300 ggtaccaaac tggaaatcaa a                                               321

<210> SEQ ID NO 11
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

-continued

Trp Ile Ser Trp Val Arg Gln Ala Pro Gly Lys Gly Leu Glu Trp Val
         35                  40                  45

Ala Glu Ile Arg Ser Glu Ser Asp Ala Ser Ala Thr His Tyr Ala Glu
 50                  55                  60

Ala Val Lys Gly Arg Phe Thr Ile Ser Arg Asp Asn Ala Lys Asn Ser
 65                  70                  75                  80

Leu Tyr Leu Gln Met Asn Ser Leu Arg Ala Glu Asp Thr Ala Val Tyr
                 85                  90                  95

Tyr Cys Leu Ala Tyr Phe Asp Tyr Gly Leu Ala Ile Gln Asn Tyr Trp
                100                 105                 110

Gly Gln Gly Thr Leu Val Thr Val Ser Ser Ala Ser Thr Lys Gly Pro
            115                 120                 125

Ser Val Phe Pro Leu Ala Pro Cys Ser Arg Ser Thr Ser Glu Ser Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Asn Phe Gly Thr Gln Thr Tyr Thr Cys Asn Val Asp
            195                 200                 205

His Lys Pro Ser Asn Thr Lys Val Asp Lys Thr Val Glu Arg Lys Cys
        210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Phe Arg Val Val
    290                 295                 300

Ser Val Leu Thr Val Val His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Thr Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Met Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 12
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 12

Glu Ile Val Leu Thr Gln Ser Pro Ala Thr Leu Ser Leu Ser Pro Gly
1               5                   10                  15

Glu Arg Ala Thr Leu Ser Cys Lys Ala Ser Lys Arg Val Thr Thr Tyr
            20                  25                  30

Val Ser Trp Tyr Gln Gln Lys Pro Gly Gln Ala Pro Arg Leu Leu Ile
        35                  40                  45

Tyr Gly Ala Ser Asn Arg Tyr Leu Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Ser Gln Ser Tyr Asn Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 13
<211> LENGTH: 1347
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 13
gaagttcagc tggttgaatc cggtggtggt ctggttcagc caggtggttc cctgcgtctg      60
tcctgcgctg cttccggttt caccttctcc aactactgga tctcctgggt tcgtcaggct     120
cctggtaaag gtctggaatg ggttgctgaa atccgttccg aatccgacgc gtccgctacc     180
cattacgctg aagctgttaa aggtcgtttc accatctccc gtgacaacgc taagaactcc     240
ctgtacctgc agatgaactc cctgcgtgct gaagacaccg ctgtttacta ctgcctggct     300
tactttgact acggtctggc tatccagaac tactggggtc agggtaccct ggttaccgtt     360
tcctccgcct ccaccaaggg cccatctgtc ttcccactgg ccccatgctc ccgcagcacc     420
tccgagagca cagccgccct gggctgcctg gtcaaggact acttcccaga acctgtgacc     480

```
gtgtcctgga actctggcgc tctgaccagc ggcgtgcaca ccttcccagc tgtcctgcag    540
tcctcaggtc tctactccct cagcagcgtg gtgaccgtgc catccagcaa cttcggcacc    600
cagacctaca cctgcaacgt agatcacaag ccaagcaaca ccaaggtcga caagaccgtg    660
gagagaaagt gttgtgtgga gtgtccacct tgtccagccc ctccagtggc cggaccatcc    720
gtgttcctgt tccctccaaa gccaaaggac accctgatga tctccagaac cccagaggtg    780
acctgtgtgg tggtggacgt gtcccacgag gacccagagg tgcagttcaa ctggtatgtg    840
gacggagtgg aggtgcacaa cgccaagacc aagccaagag aggagcagtt caactccacc    900
ttcagagtgg tgagcgtgct gaccgtggtg caccaggact ggctgaacgg aaaggagtat    960
aagtgtaagg tgtccaacaa gggactgcca tccagcatcg agaagaccat ctccaagacc   1020
aagggacagc caagagagcc acaggtgtat accctgcccc catccagaga ggagatgacc   1080
aagaaccagg tgtccctgac ctgtctggtg aagggattct atccatccga catcgccgtg   1140
gagtgggagt ccaacggaca gccagagaac aactataaga ccacccctcc aatgctggac   1200
tccgacggat ccttcttcct gtattccaag ctgaccgtgg acaagtccag atggcagcag   1260
ggaaacgtgt tctcttgttc cgtgatgcac gaggccctgc acaaccacta cccagaag    1320 agcctgtccc tgtctccagg aaagtaa                                       1347

<210> SEQ ID NO 14
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
gaaatcgttc tgacccagtc cccggctacc ctgtccctgt ccccaggtga acgtgctacc     60
ctgtcctgca agcttccaa acgggttacc acctacgttt cctggtacca gcagaaaccc    120
ggtcaggctc ctcgtctgct gatctacggt gcttccaacc gttacctcgg tatcccagct    180
cgtttctccg gttccggttc cggtaccgac ttcaccctga ccatctcctc cctggaaccc    240
gaagacttcg ctgtttacta ctgcagtcag tcctacaact accctacac cttcggtcag    300 ggtaccaaac tggaaatcaa acgcactgtg gctgcaccat ctgtcttcat cttccctcca    360
tctgatgagc agttgaaatc cggaactgcc tctgttgtgt gcctgctgaa taacttctat    420
ccgcgcgagg ccaaagtaca gtggaaggtg gataacgccc tccaatccgg taactcccag    480
gagagtgtca cagagcagga cagcaaggac agcacctaca gcctcagcag caccctgacc    540
ctgagcaaag cagactacga gaaacacaaa gtctacgcct gcgaagtcac ccatcagggc    600
ctgagttctc cagtcacaaa gagcttcaac cgcggtgagt gctaa                   645

<210> SEQ ID NO 15
<211> LENGTH: 37
<212> TYPE: PRT
<213> ORGANISM: Homo sapiens

<400> SEQUENCE: 15

Ala Cys Asp Thr Ala Thr Cys Val Thr His Arg Leu Ala Gly Leu Leu
1               5                   10                  15

Ser Arg Ser Gly Gly Val Val Lys Asn Asn Phe Val Pro Thr Asn Val
            20                  25                  30

Gly Ser Lys Ala Phe
        35
```

```
<210> SEQ ID NO 16
<211> LENGTH: 30
<212> TYPE: PRT
<213> ORGANISM: Homo sapiens

<400> SEQUENCE: 16

Val Thr His Arg Leu Ala Gly Leu Leu Ser Arg Ser Gly Gly Val Val
1               5                   10                  15

Lys Asn Asn Phe Val Pro Thr Asn Val Gly Ser Lys Ala Phe
            20                  25                  30

<210> SEQ ID NO 17
<211> LENGTH: 19
<212> TYPE: PRT
<213> ORGANISM: Homo sapiens

<400> SEQUENCE: 17

Ser Gly Gly Val Val Lys Asn Asn Phe Val Pro Thr Asn Val Gly Ser
1               5                   10                  15

Lys Ala Phe

<210> SEQ ID NO 18
<211> LENGTH: 19
<212> TYPE: PRT
<213> ORGANISM: Homo sapiens

<400> SEQUENCE: 18

Ser Gly Gly Val Val Lys Asn Asn Phe Val Ala Thr Asn Val Gly Ser
1               5                   10                  15

Lys Ala Phe

<210> SEQ ID NO 19
<211> LENGTH: 19
<212> TYPE: PRT
<213> ORGANISM: Homo sapiens

<400> SEQUENCE: 19

Ser Gly Gly Val Val Lys Asn Asn Phe Val Pro Thr Asn Val Gly Ser
1               5                   10                  15

Ala Ala Phe

<210> SEQ ID NO 20
<211> LENGTH: 19
<212> TYPE: PRT
<213> ORGANISM: Homo sapiens

<400> SEQUENCE: 20

Ser Gly Gly Val Val Lys Asn Asn Phe Val Pro Thr Asn Val Gly Ser
1               5                   10                  15

Glu Ala Phe

<210> SEQ ID NO 21
<211> LENGTH: 19
<212> TYPE: PRT
<213> ORGANISM: Homo sapiens

<400> SEQUENCE: 21

Ser Gly Gly Val Val Lys Asn Asn Phe Val Pro Thr Asn Val Gly Ser
1               5                   10                  15
```

Met Ala Phe

<210> SEQ ID NO 22
<211> LENGTH: 19
<212> TYPE: PRT
<213> ORGANISM: Homo sapiens

<400> SEQUENCE: 22

Ser Gly Gly Val Val Lys Asn Asn Phe Val Pro Thr Asn Val Gly Ser
1               5                   10                  15

Gln Ala Phe

<210> SEQ ID NO 23
<211> LENGTH: 19
<212> TYPE: PRT
<213> ORGANISM: Homo sapiens

<400> SEQUENCE: 23

Ser Gly Gly Val Val Lys Asn Asn Phe Val Pro Thr Asn Val Gly Ser
1               5                   10                  15

Lys Ala Ala

<210> SEQ ID NO 24
<211> LENGTH: 14
<212> TYPE: PRT
<213> ORGANISM: Homo sapiens

<400> SEQUENCE: 24

Asn Asn Phe Val Pro Thr Asn Val Gly Ser Lys Ala Phe Ala
1               5                   10

<210> SEQ ID NO 25
<211> LENGTH: 13
<212> TYPE: PRT
<213> ORGANISM: Homo sapiens

<400> SEQUENCE: 25

Asn Asn Phe Val Pro Thr Asn Val Gly Ser Lys Ala Phe
1               5                   10

<210> SEQ ID NO 26
<211> LENGTH: 13
<212> TYPE: PRT
<213> ORGANISM: Homo sapiens

<400> SEQUENCE: 26

Asn Asn Ala Val Pro Thr Asn Val Gly Ser Lys Ala Phe
1               5                   10

<210> SEQ ID NO 27
<211> LENGTH: 13
<212> TYPE: PRT
<213> ORGANISM: Homo sapiens

<400> SEQUENCE: 27

Asn Asn Phe Ala Pro Thr Asn Val Gly Ser Lys Ala Phe
1               5                   10

<210> SEQ ID NO 28
<211> LENGTH: 13
<212> TYPE: PRT
<213> ORGANISM: Homo sapiens

<400> SEQUENCE: 28

Asn Asn Phe Val Ala Thr Asn Val Gly Ser Lys Ala Phe
1               5                   10

<210> SEQ ID NO 29
<211> LENGTH: 13
<212> TYPE: PRT
<213> ORGANISM: Homo sapiens

<400> SEQUENCE: 29

Asn Asn Phe Val Pro Ala Asn Val Gly Ser Lys Ala Phe
1               5                   10

<210> SEQ ID NO 30
<211> LENGTH: 13
<212> TYPE: PRT
<213> ORGANISM: Homo sapiens

<400> SEQUENCE: 30

Asn Asn Phe Val Pro Thr Ala Val Gly Ser Lys Ala Phe
1               5                   10

<210> SEQ ID NO 31
<211> LENGTH: 13
<212> TYPE: PRT
<213> ORGANISM: Homo sapiens

<400> SEQUENCE: 31

Asn Asn Phe Val Pro Thr Asn Ala Gly Ser Lys Ala Phe
1               5                   10

<210> SEQ ID NO 32
<211> LENGTH: 13
<212> TYPE: PRT
<213> ORGANISM: Homo sapiens

<400> SEQUENCE: 32

Asn Asn Phe Val Pro Thr Asn Val Ala Ser Lys Ala Phe
1               5                   10

<210> SEQ ID NO 33
<211> LENGTH: 13
<212> TYPE: PRT
<213> ORGANISM: Homo sapiens

<400> SEQUENCE: 33

Asn Asn Phe Val Pro Thr Asn Val Gly Ala Lys Ala Phe
1               5                   10

<210> SEQ ID NO 34
<211> LENGTH: 13
<212> TYPE: PRT
<213> ORGANISM: Homo sapiens

<400> SEQUENCE: 34

Asn Asn Phe Val Pro Thr Asn Val Gly Ser Lys Ala Ala
1               5                   10

<210> SEQ ID NO 35
<211> LENGTH: 12
<212> TYPE: PRT
<213> ORGANISM: Homo sapiens

<400> SEQUENCE: 35

Asn Phe Val Pro Thr Asn Val Gly Ser Lys Ala Phe

```
<210> SEQ ID NO 36
<211> LENGTH: 19
<212> TYPE: PRT
<213> ORGANISM: Homo sapiens

<400> SEQUENCE: 36

Ser Gly Gly Val Val Lys Asn Asn Phe Val Pro Thr Asn Val Gly Ser
  1               5                   10                  15

Lys Ala Phe

<210> SEQ ID NO 37
<211> LENGTH: 18
<212> TYPE: PRT
<213> ORGANISM: Homo sapiens

<400> SEQUENCE: 37

Ser Gly Gly Val Val Lys Asn Asn Phe Val Pro Thr Asn Val Gly Ser
  1               5                   10                  15

Lys Ala

<210> SEQ ID NO 38
<211> LENGTH: 36
<212> TYPE: PRT
<213> ORGANISM: Homo sapiens

<400> SEQUENCE: 38

Ala Cys Asp Thr Ala Thr Cys Val Thr His Arg Leu Ala Gly Leu Leu
  1               5                   10                  15

Ser Arg Ser Gly Gly Val Val Lys Asn Asn Phe Val Pro Thr Asn Val
             20                  25                  30

Gly Ser Lys Ala
              35

<210> SEQ ID NO 39
<211> LENGTH: 19
<212> TYPE: PRT
<213> ORGANISM: Homo sapiens

<400> SEQUENCE: 39

Ala Cys Asp Thr Ala Thr Cys Val Thr His Arg Leu Ala Gly Leu Leu
  1               5                   10                  15

Ser Arg Ser

<210> SEQ ID NO 40
<211> LENGTH: 13
<212> TYPE: PRT
<213> ORGANISM: Homo sapiens

<400> SEQUENCE: 40

Ala Cys Asp Thr Ala Thr Cys Val Thr His Arg Leu Ala
  1               5                   10

<210> SEQ ID NO 41
<211> LENGTH: 37
<212> TYPE: PRT
<213> ORGANISM: Rattus sp.

<400> SEQUENCE: 41

Ser Cys Asn Thr Ala Thr Cys Val Thr His Arg Leu Ala Gly Leu Leu
  1               5                   10                  15
```

Ser Arg Ser Gly Gly Val Val Lys Asp Asn Phe Val Pro Thr Asn Val
            20                  25                  30

Gly Ser Glu Ala Phe
            35

<210> SEQ ID NO 42
<211> LENGTH: 19
<212> TYPE: PRT
<213> ORGANISM: Rattus sp.

<400> SEQUENCE: 42

Ser Gly Gly Val Val Lys Asp Asn Phe Val Pro Thr Asn Val Gly Ser
1               5                   10                  15

Glu Ala Phe

<210> SEQ ID NO 43
<211> LENGTH: 37
<212> TYPE: PRT
<213> ORGANISM: Homo sapiens

<400> SEQUENCE: 43

Ala Cys Asn Thr Ala Thr Cys Val Thr His Arg Leu Ala Gly Leu Leu
1               5                   10                  15

Ser Arg Ser Gly Gly Met Val Lys Ser Asn Phe Val Pro Thr Asn Val
            20                  25                  30

Gly Ser Lys Ala Phe
            35

<210> SEQ ID NO 44
<211> LENGTH: 37
<212> TYPE: PRT
<213> ORGANISM: Rattus sp.

<400> SEQUENCE: 44

Ser Cys Asn Thr Ala Thr Cys Val Thr His Arg Leu Ala Gly Leu Leu
1               5                   10                  15

Ser Arg Ser Gly Gly Val Val Lys Asp Asn Phe Val Pro Thr Asn Val
            20                  25                  30

Gly Ser Lys Ala Phe
            35

<210> SEQ ID NO 45
<211> LENGTH: 32
<212> TYPE: PRT
<213> ORGANISM: Homo sapiens

<400> SEQUENCE: 45

Cys Gly Asn Leu Ser Thr Cys Met Leu Gly Thr Tyr Thr Gln Asp Phe
1               5                   10                  15

Asn Lys Phe His Thr Phe Pro Gln Thr Ala Ile Gly Val Gly Ala Pro
            20                  25                  30

<210> SEQ ID NO 46
<211> LENGTH: 37
<212> TYPE: PRT
<213> ORGANISM: Homo sapiens

<400> SEQUENCE: 46

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Thr Asn Val
            20                  25                  30

Gly Ser Asn Thr Tyr
        35

<210> SEQ ID NO 47
<211> LENGTH: 52
<212> TYPE: PRT
<213> ORGANISM: Homo sapiens

<400> SEQUENCE: 47

Tyr Arg Gln Ser Met Asn Asn Phe Gln Gly Leu Arg Ser Phe Gly Cys
1               5                   10                  15

Arg Phe Gly Thr Cys Thr Val Gln Lys Leu Ala His Gln Ile Tyr Gln
            20                  25                  30

Phe Thr Asp Lys Asp Lys Asp Asn Val Ala Pro Arg Ser Lys Ile Ser
        35                  40                  45

Pro Gln Gly Tyr
    50

<210> SEQ ID NO 48
<211> LENGTH: 4
<212> TYPE: PRT
<213> ORGANISM: Homo sapiens

<400> SEQUENCE: 48

Glu Leu Leu Gly
1

<210> SEQ ID NO 49
<211> LENGTH: 7
<212> TYPE: PRT
<213> ORGANISM: Homo sapiens

<400> SEQUENCE: 49

Glu Leu Leu Gly Ala Ala Pro
1               5

<210> SEQ ID NO 50
<211> LENGTH: 6
<212> TYPE: PRT
<213> ORGANISM: Homo sapiens

<400> SEQUENCE: 50

Pro Val Ala Gly Ser Ser
1               5

<210> SEQ ID NO 51
<211> LENGTH: 6
<212> TYPE: PRT
<213> ORGANISM: Homo sapiens

<400> SEQUENCE: 51

Glu Leu Leu Ala Ala Pro
1               5

<210> SEQ ID NO 52
<211> LENGTH: 4
<212> TYPE: PRT
<213> ORGANISM: Homo sapiens

<400> SEQUENCE: 52

Glu Phe Leu Gly
1

```
<210> SEQ ID NO 53
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Arg, Trp, Gly, Leu or Asn
<220> FEATURE:
<221> NAME/KEY: MOD_RES
<222> LOCATION: (7)..(7)
<223> OTHER INFORMATION: Thr, Ala, Asp, Gly, Arg, Ser, Trp or Val

<400> SEQUENCE: 53

Lys Ala Ser Lys Xaa Val Xaa Thr Tyr Val Ser
1               5                   10

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gly or Ala
<220> FEATURE:
<221> NAME/KEY: MOD_RES
<222> LOCATION: (2)..(2)
<223> OTHER INFORMATION: Ala or His
<220> FEATURE:
<221> NAME/KEY: MOD_RES
<222> LOCATION: (7)..(7)
<223> OTHER INFORMATION: Leu, Thr, Ile or Ser

<400> SEQUENCE: 54

Xaa Xaa Ser Asn Arg Tyr Xaa
1               5

<210> SEQ ID NO 55
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Glu, Arg, Lys, Gln or Asn
<220> FEATURE:
<221> NAME/KEY: MOD_RES
<222> LOCATION: (8)..(8)
<223> OTHER INFORMATION: Ala, Gly, Asn, Glu, His, Ser, Leu, Arg, Cys,
      Phe, Tyr, Val, Asp or Pro
<220> FEATURE:
<221> NAME/KEY: MOD_RES
<222> LOCATION: (9)..(9)
<223> OTHER INFORMATION: Ser, Gly, Thr, Tyr, Cys, Glu, Leu, Ala, Pro,
      Ile, Asn, Arg, Val, Asp or Met
<220> FEATURE:
<221> NAME/KEY: MOD_RES
<222> LOCATION: (12)..(12)
<223> OTHER INFORMATION: His or Phe
<220> FEATURE:
<221> NAME/KEY: MOD_RES
<222> LOCATION: (15)..(15)
```

```
<223> OTHER INFORMATION: Glu or Asp

<400> SEQUENCE: 55

Glu Ile Arg Ser Xaa Ser Asp Xaa Xaa Ala Thr Xaa Tyr Ala Xaa Ala
1               5                   10                  15

Val Lys Gly

<210> SEQ ID NO 56
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 56

His His His His His His
1               5

<210> SEQ ID NO 57
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gly Gly Gly Gly Ser Gly Gly Gly Gly Ser Gly Gly Gly Gly Ser
1               5                   10                  15
```